US011752189B2

(12) United States Patent
Noelle et al.

(10) Patent No.: US 11,752,189 B2
(45) Date of Patent: *Sep. 12, 2023

(54) VISTA ANTAGONIST AND METHODS OF USE

(71) Applicants: THE TRUSTEES OF DARTMOUTH COLLEGE, Hanover, NH (US); KING'S COLLEGE LONDON, London (GB)

(72) Inventors: Randolph J. Noelle, Plainfield, NH (US); Sabrina Ceeraz, Lebanon, NH (US); Isabelle LeMercier, Enfield, NH (US); Elizabeth Nowak, West Lebanon, NH (US); Janet Lines, London (GB); Li Wang, Norwich, VT (US); Mark Spaller, Lebanon, NH (US)

(73) Assignees: THE TRUSTEES OF DARTMOUTH COLLEGE, Hanover, NH (US); KING'S COLLEGE LONDON, London (GB)

( * ) Notice: Subject to any disclaimer, the term of this patent is extended or adjusted under 35 U.S.C. 154(b) by 777 days.

This patent is subject to a terminal disclaimer.

(21) Appl. No.: 16/669,552

(22) Filed: Oct. 31, 2019

(65) Prior Publication Data

US 2020/0093902 A1 Mar. 26, 2020

Related U.S. Application Data

(63) Continuation of application No. 14/534,793, filed on Nov. 6, 2014, now abandoned.

(51) Int. Cl.
| | |
|---|---|
| *C07K 7/08* | (2006.01) |
| *A61K 38/10* | (2006.01) |
| *A61K 45/06* | (2006.01) |
| *A61K 9/00* | (2006.01) |
| *A61K 39/00* | (2006.01) |
| *C07K 16/28* | (2006.01) |
| *G01N 33/566* | (2006.01) |
| *A61K 38/00* | (2006.01) |

(52) U.S. Cl.
CPC ............ *A61K 38/10* (2013.01); *A61K 9/0019* (2013.01); *A61K 39/0005* (2013.01); *A61K 45/06* (2013.01); *C07K 7/08* (2013.01); *C07K 16/2827* (2013.01); *G01N 33/566* (2013.01); *A61K 38/00* (2013.01); *C07K 2317/74* (2013.01); *C07K 2317/76* (2013.01); *C07K 2319/30* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,517,288 | A | 5/1985 | Giegel et al. |
| 4,522,811 | A | 6/1985 | Eppstein et al. |
| 4,596,556 | A | 6/1986 | Morrow et al. |
| 4,676,980 | A | 6/1987 | Segal et al. |
| 4,683,195 | A | 7/1987 | Mullis et al. |
| 4,683,202 | A | 7/1987 | Mullis |
| 4,699,880 | A | 10/1987 | Goldstein |
| 4,736,866 | A | 4/1988 | Leder et al. |
| 4,790,824 | A | 12/1988 | Morrow et al. |
| 4,816,567 | A | 3/1989 | Cabilly et al. |
| 4,837,168 | A | 6/1989 | de Jaeger et al. |
| 4,870,009 | A | 9/1989 | Evans et al. |
| 4,873,191 | A | 10/1989 | Wagner et al. |
| 4,873,316 | A | 10/1989 | Meade et al. |
| 4,881,175 | A | 11/1989 | Ladner |
| 4,941,880 | A | 7/1990 | Burns |
| 4,946,778 | A | 8/1990 | Ladner et al. |
| 4,954,617 | A | 9/1990 | Fanger et al. |
| 4,987,071 | A | 1/1991 | Cech et al. |
| 5,013,653 | A | 5/1991 | Huston et al. |
| 5,064,413 | A | 11/1991 | McKinnon et al. |

(Continued)

FOREIGN PATENT DOCUMENTS

| | | |
|---|---|---|
| CA | 2383456 | 3/2001 |
| CN | 1753912 | 3/2006 |

(Continued)

OTHER PUBLICATIONS

This application is a Continuation of, U.S. Appl. No. 14/534,793, filed Nov. 6, 2014, Abandoned.
Cancer Prevention Overview (PDQ®), PDQ Cancer Information Summaries [Internet].2017, 14 pages.
Antonarakis ES. "Combining active immunotherapy with immune checkpoint blockade for the treatment of advanced prostate cancer," Asian J Androl. Jul. 2012;14(4):520-1.
Brahmer JR, et al. "Safety and activity of anti-PD-L1 antibody in patients with advanced cancer," N Engl J Med. Jun. 28, 2012;366(26):2455-65.
Brahmer, et al. Supplementary Appendix, Jun. 28, 2012, 26 pages.
Brahmer, et al. Supplementary Protocol, Jun. 28, 2012, 700 pages.

(Continued)

*Primary Examiner* — Ilia I Ouspenski
(74) *Attorney, Agent, or Firm* — Robin L. Teskin; Baker, Donelson, Bearman, Caldwell & Berkowitz PC

(57) ABSTRACT

The present invention is directed to a peptide, multimer, conjugate, analog, derivative or mimetic thereof that inhibits the activity of VISTA. The invention further contemplates therapeutic use of the VISTA antagonist peptide, multimer, conjugate, derivative or mimetic thereof, including treating or preventing cancer, bacterial infections, viral infections, parasitic infections and fungal infections, as well as research uses of the antagonist.

17 Claims, 2 Drawing Sheets

Specification includes a Sequence Listing.

(56) References Cited

U.S. PATENT DOCUMENTS

| | | | |
|---|---|---|---|
| 5,091,513 | A | 2/1992 | Huston et al. |
| 5,116,742 | A | 5/1992 | Cech et al. |
| 5,116,964 | A | 5/1992 | Capon et al. |
| 5,132,405 | A | 7/1992 | Huston et al. |
| 5,139,941 | A | 8/1992 | Muzyczka et al. |
| 5,190,878 | A | 3/1993 | Wilhelm |
| 5,223,409 | A | 6/1993 | Ladner et al. |
| 5,225,539 | A | 7/1993 | Winter et al. |
| 5,258,498 | A | 11/1993 | Huston et al. |
| 5,260,203 | A | 11/1993 | Ladner et al. |
| 5,272,071 | A | 12/1993 | Chappel |
| 5,283,173 | A | 2/1994 | Fields et al. |
| 5,283,317 | A | 2/1994 | Saifer et al. |
| 5,288,641 | A | 2/1994 | Roizman |
| 5,312,335 | A | 5/1994 | McKinnon et al. |
| 5,328,470 | A | 7/1994 | Nabel et al. |
| 5,374,548 | A | 12/1994 | Caras |
| 5,383,851 | A | 1/1995 | McKinnon, Jr. et al. |
| 5,399,163 | A | 3/1995 | Peterson et al. |
| 5,399,331 | A | 3/1995 | Loughrey et al. |
| 5,403,484 | A | 4/1995 | Ladner et al. |
| 5,416,016 | A | 5/1995 | Low et al. |
| 5,427,908 | A | 6/1995 | Dower et al. |
| 5,455,030 | A | 10/1995 | Ladner et al. |
| 5,476,786 | A | 12/1995 | Huston |
| 5,476,996 | A | 12/1995 | Wilson et al. |
| 5,478,925 | A | 12/1995 | Wallach et al. |
| 5,482,858 | A | 1/1996 | Huston et al. |
| 5,530,101 | A | 6/1996 | Queen et al. |
| 5,545,806 | A | 8/1996 | Lonberg et al. |
| 5,545,807 | A | 8/1996 | Surani et al. |
| 5,547,853 | A | 8/1996 | Wallner et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,580,756 | A | 12/1996 | Linsley et al. |
| 5,585,089 | A | 12/1996 | Queen et al. |
| 5,624,659 | A | 4/1997 | Bigner et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,648,260 | A | 7/1997 | Winter et al. |
| 5,661,016 | A | 8/1997 | Lonberg et al. |
| 5,677,425 | A | 10/1997 | Bodmer et al. |
| 5,693,762 | A | 12/1997 | Queen et al. |
| 5,698,767 | A | 12/1997 | Wilson et al. |
| 5,714,350 | A | 2/1998 | Co et al. |
| 5,723,125 | A | 3/1998 | Chang et al. |
| 5,731,168 | A | 3/1998 | Carter et al. |
| 5,770,429 | A | 6/1998 | Lonberg et al. |
| 5,776,427 | A | 7/1998 | Thorpe et al. |
| 5,789,650 | A | 8/1998 | Lonberg et al. |
| 5,811,097 | A | 9/1998 | Allison et al. |
| 5,814,318 | A | 9/1998 | Lonberg et al. |
| 5,821,333 | A | 10/1998 | Carter et al. |
| 5,837,243 | A | 11/1998 | Deo et al. |
| 5,844,095 | A | 12/1998 | Linsley et al. |
| 5,851,795 | A | 12/1998 | Linsley et al. |
| 5,869,046 | A | 2/1999 | Presta et al. |
| 5,874,299 | A | 2/1999 | Lonberg et al. |
| 5,877,397 | A | 3/1999 | Lonberg et al. |
| 5,885,793 | A | 3/1999 | Griffiths et al. |
| 5,888,807 | A | 3/1999 | Palsson et al. |
| 5,922,845 | A | 7/1999 | Deo et al. |
| 5,932,448 | A | 8/1999 | Tso et al. |
| 5,939,598 | A | 8/1999 | Kucherlapati et al. |
| 5,969,108 | A | 10/1999 | McCafferty et al. |
| 5,985,653 | A | 11/1999 | Armstrong et al. |
| 6,054,297 | A | 4/2000 | Carter et al. |
| 6,069,134 | A | 5/2000 | Roth et al. |
| 6,075,181 | A | 6/2000 | Kucherlapati et al. |
| 6,096,532 | A | 8/2000 | Armstrong et al. |
| 6,114,598 | A | 9/2000 | Kucherlapati et al. |
| 6,121,022 | A | 9/2000 | Presta et al. |
| 6,150,584 | A | 11/2000 | Kucherlapati et al. |
| 6,153,737 | A | 11/2000 | Manoharan et al. |
| 6,162,963 | A | 12/2000 | Kucherlapati et al. |
| 6,165,745 | A | 12/2000 | Ward et al. |
| 6,172,197 | B1 | 1/2001 | McCafferty et al. |
| 6,172,208 | B1 | 1/2001 | Cook |
| 6,180,370 | B1 | 1/2001 | Queen et al. |
| 6,187,287 | B1 | 2/2001 | Leung et al. |
| 6,194,551 | B1 | 2/2001 | Idusogie et al. |
| 6,277,375 | B1 | 8/2001 | Ward |
| 6,300,319 | B1 | 10/2001 | Manoharan |
| 6,335,434 | B1 | 1/2002 | Guzaev et al. |
| 6,335,437 | B1 | 1/2002 | Manoharan |
| 6,350,861 | B1 | 2/2002 | Co et al. |
| 6,395,437 | B1 | 5/2002 | Wollesen |
| 6,407,213 | B1 | 6/2002 | Carter et al. |
| 6,444,806 | B1 | 9/2002 | Veerapanani et al. |
| 6,486,308 | B2 | 11/2002 | Kutyavin et al. |
| 6,492,123 | B1 | 12/2002 | Holliger et al. |
| 6,521,404 | B1 | 2/2003 | Griffiths et al. |
| 6,525,031 | B2 | 2/2003 | Manoharan |
| 6,528,631 | B1 | 3/2003 | Cook et al. |
| 6,544,731 | B1 | 4/2003 | Griffiths et al. |
| 6,545,170 | B2 | 4/2003 | Pitzele et al. |
| 6,548,640 | B1 | 4/2003 | Winter |
| 6,555,313 | B1 | 4/2003 | Griffiths et al. |
| 6,559,279 | B1 | 5/2003 | Manoharan et al. |
| 6,562,576 | B2 | 5/2003 | Manfredi |
| 6,582,915 | B1 | 6/2003 | Griffiths et al. |
| 6,586,474 | B2 | 7/2003 | Webber et al. |
| 6,591,889 | B2 | 7/2003 | Bettio et al. |
| 6,593,081 | B1 | 7/2003 | Griffiths et al. |
| 6,593,372 | B2 | 7/2003 | Enikolopov et al. |
| 6,632,927 | B2 | 10/2003 | Adair et al. |
| 6,639,055 | B1 | 10/2003 | Carter et al. |
| 6,653,104 | B2 | 11/2003 | Goldenberg |
| 6,696,686 | B1 | 2/2004 | Wainer et al. |
| 6,790,624 | B2 | 9/2004 | Mayer |
| 6,809,117 | B2 | 10/2004 | Enikolopov et al. |
| 6,818,418 | B1 | 11/2004 | Lipovsek et al. |
| 6,924,355 | B2 | 8/2005 | Baker et al. |
| 6,936,436 | B2 | 8/2005 | Baker et al. |
| 6,936,697 | B2 | 8/2005 | Desnoyers et al. |
| 6,982,323 | B1 | 1/2006 | Wang et al. |
| 7,026,448 | B2 | 4/2006 | Baker et al. |
| 7,049,058 | B2 | 5/2006 | Singh |
| 7,196,118 | B2 | 3/2007 | Webber et al. |
| 7,226,759 | B2 | 6/2007 | Sun |
| 7,250,297 | B1 | 7/2007 | Beste et al. |
| 7,488,802 | B2 | 2/2009 | Collins et al. |
| 7,595,048 | B2 | 9/2009 | Honjo et al. |
| 7,655,778 | B2 | 2/2010 | Yang |
| 7,919,585 | B2 | 4/2011 | Chen |
| 8,119,117 | B2 | 2/2012 | Deisseroth et al. |
| 8,231,872 | B2 | 7/2012 | Noelle et al. |
| 8,236,304 | B2 | 8/2012 | Noelle et al. |
| 8,465,740 | B2 | 6/2013 | Noelle et al. |
| 8,501,915 | B2 | 8/2013 | Noelle et al. |
| 8,652,465 | B2 | 2/2014 | Freeman et al. |
| 9,217,035 | B2 | 12/2015 | Noelle et al. |
| 9,381,244 | B2 | 7/2016 | Noelle et al. |
| 9,631,018 | B2 | 4/2017 | Noelle et al. |
| 9,879,092 | B2 | 1/2018 | Laury-Kleintop et al. |
| 9,890,215 | B2 | 2/2018 | Noelle et al. |
| 10,035,857 | B2 | 7/2018 | Noelle et al. |
| 10,370,455 | B2 | 8/2019 | Molloy et al. |
| 10,933,115 | B2 * | 3/2021 | Noelle ................. A61K 38/10 |
| 11,180,557 | B2 | 11/2021 | Noelle et al. |
| 2003/0031671 | A1 | 2/2003 | Welt et al. |
| 2003/0054406 | A1 | 3/2003 | Baker et al. |
| 2004/0110704 | A1 | 6/2004 | Yamane et al. |
| 2004/0132028 | A1 | 7/2004 | Stumpp et al. |
| 2004/0132101 | A1 | 7/2004 | Lazar et al. |
| 2004/0259209 | A1 | 12/2004 | Sun et al. |
| 2005/0043519 | A1 | 2/2005 | Dooley et al. |
| 2005/0063948 | A1 | 3/2005 | Dickerson et al. |
| 2006/0025576 | A1 | 2/2006 | Miller et al. |
| 2006/0034852 | A1 | 2/2006 | Rixon et al. |
| 2006/0084082 | A1 | 4/2006 | Ruben et al. |
| 2007/0092512 | A1 | 4/2007 | Daaka et al. |

(56) References Cited

U.S. PATENT DOCUMENTS

| | | | |
|---|---|---|---|
| 2007/0122378 A1 | 5/2007 | Freeman et al. | |
| 2007/0148167 A1 | 6/2007 | Stohl | |
| 2007/0224633 A1 | 9/2007 | Skerra et al. | |
| 2008/0069820 A1 | 3/2008 | Fuh et al. | |
| 2008/0139791 A1 | 6/2008 | Lipovsek et al. | |
| 2008/0166353 A1 | 7/2008 | Cherwinski | |
| 2008/0248007 A1 | 10/2008 | Chen | |
| 2008/0287358 A1 | 11/2008 | Noelle et al. | |
| 2009/0215991 A1 | 8/2009 | Lazar et al. | |
| 2010/0316639 A1 | 12/2010 | Lackner | |
| 2010/0317834 A1 | 12/2010 | Lazar et al. | |
| 2011/0027278 A1 | 2/2011 | Noelle et al. | |
| 2011/0158995 A1 | 6/2011 | Tan et al. | |
| 2011/0206699 A1 | 8/2011 | Hossain et al. | |
| 2011/0223188 A1 | 9/2011 | Langermann et al. | |
| 2011/0243942 A1 | 10/2011 | Wang | |
| 2012/0195894 A1 | 8/2012 | Noelle et al. | |
| 2013/0177557 A1 | 7/2013 | Noelle et al. | |
| 2014/0037634 A1 | 2/2014 | Noelle et al. | |
| 2014/0056890 A1 | 2/2014 | Gurney et al. | |
| 2014/0056892 A1 | 2/2014 | Noelle et al. | |
| 2014/0105912 A1 | 4/2014 | Noelle | |
| 2014/0220012 A1 | 8/2014 | Noelle et al. | |
| 2014/0227279 A1 | 8/2014 | Laury-Kleintop et al. | |
| 2014/0341920 A1 | 11/2014 | Noelle | |
| 2015/0231215 A1 | 8/2015 | Noelle et al. | |
| 2016/0008316 A1 | 1/2016 | Bacha et al. | |
| 2016/0083472 A1 | 3/2016 | Noelle et al. | |
| 2016/0096891 A1 | 4/2016 | Chen et al. | |
| 2016/0159927 A1 | 6/2016 | Molloy et al. | |
| 2016/0168248 A1 | 6/2016 | Noelle et al. | |
| 2016/0318999 A9 | 11/2016 | Noelle et al. | |
| 2016/0331803 A1 | 11/2016 | Noelle et al. | |
| 2016/0369005 A1 | 12/2016 | Lippincott et al. | |
| 2017/0051061 A1 | 2/2017 | Snyder et al. | |
| 2017/0119877 A1 | 5/2017 | Green et al. | |
| 2017/0233479 A1 | 8/2017 | Snyder et al. | |
| 2017/0320950 A1 | 11/2017 | Snyder et al. | |
| 2017/0334990 A1 | 11/2017 | Noelle et al. | |
| 2018/0051070 A1 | 2/2018 | Noelle et al. | |
| 2018/0079811 A1 | 3/2018 | Molloy et al. | |
| 2018/0215826 A1 | 8/2018 | Noelle et al. | |
| 2020/0017589 A1 | 1/2020 | Snyder et al. | |
| 2021/0017281 A1 | 1/2021 | Molloy et al. | |
| 2021/0253708 A1* | 8/2021 | Noelle | A61K 39/00 |
| 2021/0317206 A1 | 10/2021 | Molloy et al. | |
| 2021/0317207 A1 | 10/2021 | Noelle et al. | |
| 2021/0361736 A1* | 11/2021 | Noelle | A61K 38/10 |

FOREIGN PATENT DOCUMENTS

| | | |
|---|---|---|
| EP | 0 045 665 | 2/1982 |
| EP | 0045665 | 2/1982 |
| EP | 0 125 023 | 11/1984 |
| EP | 0125023 | 11/1984 |
| EP | 0 154 316 | 9/1985 |
| EP | 0 171496 | 2/1986 |
| EP | 0171496 | 2/1986 |
| EP | 0 173 494 | 3/1986 |
| EP | 0173494 | 3/1986 |
| EP | 0 184 187 | 6/1986 |
| EP | 0184187 | 6/1986 |
| EP | 0 264 166 | 4/1988 |
| EP | 264166 | 4/1988 |
| EP | 0 401 384 | 12/1990 |
| EP | 1 176 195 | 1/2002 |
| EP | 1 641 818 | 4/2006 |
| JP | 08-506635 | 3/2008 |
| WO | WO 00/045665 | 2/1982 |
| WO | WO 1986001533 | 3/1986 |
| WO | WO 87/002671 | 5/1987 |
| WO | WO 87/005330 | 9/1987 |
| WO | WO 88/000052 | 1/1988 |
| WO | WO 1988009810 | 12/1988 |
| WO | WO 1989010134 | 11/1989 |
| WO | WO 1991006667 | 5/1991 |
| WO | WO 92/003918 | 3/1992 |
| WO | WO 93/008829 | 5/1993 |
| WO | WO 93/012227 | 6/1993 |
| WO | WO 94/010332 | 5/1994 |
| WO | WO 1994010300 | 5/1994 |
| WO | WO 94/025585 | 11/1994 |
| WO | WO 94/029351 | 12/1994 |
| WO | WO 1994029436 | 12/1994 |
| WO | WO 1997007668 | 3/1997 |
| WO | WO 1997007669 | 3/1997 |
| WO | WO 97/013852 | 4/1997 |
| WO | WO 97/28267 | 8/1997 |
| WO | WO 98/024884 | 6/1998 |
| WO | WO 99/045962 | 9/1999 |
| WO | WO 99/054342 | 10/1999 |
| WO | WO 00/006593 | 2/2000 |
| WO | WO 00/029004 | 5/2000 |
| WO | WO 00/031113 | 6/2000 |
| WO | WO 00/042072 | 7/2000 |
| WO | WO 01/000814 | 1/2001 |
| WO | WO 2001003737 | 1/2001 |
| WO | WO 01/014424 | 3/2001 |
| WO | WO 2002029072 | 4/2002 |
| WO | WO 02/043478 | 6/2002 |
| WO | WO 2002/079449 | 10/2002 |
| WO | WO 02/092780 | 11/2002 |
| WO | WO 03/035835 | 5/2003 |
| WO | WO 03/074679 | 9/2003 |
| WO | WO 2004018520 | 3/2004 |
| WO | WO 04/037999 | 5/2004 |
| WO | WO 2004/037999 | 5/2004 |
| WO | WO 05/056764 | 6/2005 |
| WO | WO 2005/112834 | 12/2005 |
| WO | WO 2005113606 | 12/2005 |
| WO | 2006/012232 | 2/2006 |
| WO | WO 06/050247 | 5/2006 |
| WO | WO 06/050262 | 5/2006 |
| WO | WO 06/116181 | 11/2006 |
| WO | WO 2006116181 | 11/2006 |
| WO | WO 2007030198 | 3/2007 |
| WO | WO 08/098796 | 8/2008 |
| WO | WO 09/089004 | 7/2009 |
| WO | 2010/027827 | 3/2010 |
| WO | 2011/120013 | 9/2011 |
| WO | WO 13/184912 | 12/2013 |
| WO | WO 2013/184912 | 12/2013 |
| WO | WO 2013192504 | 12/2013 |
| WO | WO 2014039983 | 3/2014 |
| WO | WO 14/190356 | 11/2014 |
| WO | 2014197849 | 12/2014 |
| WO | WO 2015097536 | 7/2015 |
| WO | WO 2015109340 | 7/2015 |
| WO | WO 2015191881 | 12/2015 |
| WO | WO 2016090347 | 6/2016 |
| WO | 2016207717 | 12/2016 |
| WO | WO 2017181109 | 10/2017 |
| WO | WO 2017181139 | 10/2017 |
| WO | WO 18/027042 | 2/2018 |
| WO | WO 2018/027042 | 2/2018 |

OTHER PUBLICATIONS

Curran MA, et al. "PD-1 and CTLA-4 combination blockade expands infiltrating T cells and reduces regulatory T and myeloid cells within B16 melanoma tumors," Proc Natl Acad Sci U S A. Mar. 2, 2010;107(9):4275-80.

Wang, Li PhD—Dartmouth Medical School Presentation at the SITC (Society for Immunotherapy of Cancer) 26th Annual Meeting Dec. 2011.

Martinez Forero I, et al. "Workshop on immunotherapy combinations. Society for Immunotherapy of Cancer annual meeting Bethesda, Novembers, 2011," J Transl Med. May 28, 2012;10:108.

Pilon-Thomas S, et al. "Blockade of programmed death ligand 1 enhances the therapeutic efficacy of combination immunotherapy against melanoma," J Immunol. Apr. 1, 2010;184(7):3442-9.

Program of the SITC (Society for Immunotherapy of Cancer) 26th Annual Meeting Nov. 2011.

(56) References Cited

OTHER PUBLICATIONS

Quah BJ, et al. "The use of carboxyfluorescein diacetate succinimidyl ester (CFSE) to monitor lymphocyte proliferation," J Vis Exp. Oct. 12, 2010;(44). pii: 2259.
Topalian SL, et al. "Targeting the PD-1/B7-H1(PD-L1) pathway to activate anti-tumor immunity," Curr Opin Immunol. Apr. 2012;24(2):207-12.
Wang, L. et al. "Immune Checkpoint Protein Vista as a Novel Target for Cancer Immunotherapy," Abstracts for the 27th Annual Scientific Meeting of the Society for Immunotherapy of Cancer (SITC), J Immunother. Nov.-Dec. 2012;35(9):721,781.
Yu P, et al. "Simultaneous blockade of multiple immune system inhibitory checkpoints enhances antitumor activity mediated by interleukin-15 in a murine metastatic colon carcinoma model," Clin Cancer Res. Dec. 15, 2010;16(24):6019-28.
Yu P, et al. "Simultaneous inhibition of two regulatory T-cell subsets enhanced Interleukin-15 efficacy in a prostate tumor model," Proc Natl Acad Sci U S A. Apr. 17, 2012;109(16):6187-92.
Zitvogel L, et al. "Targeting PD-1/PD-L1 interactions for cancer immunotherapy," Oncoimmunology. Nov. 1, 2012;1(8):1223-1225.
Abdiche, Yasmina Noubia et al. "Assessing kinetic and epitopic diversity across orthogonal monoclonal antibody generation platforms." mAbs vol. 8,2 (2016): 264-77. doi: 10.1080/19420862.2015.1118596.
Balducci, Lodovico. "Cancer Prevention in the Older Individual." Seminars in oncology nursing vol. 32,3 (2016): 314-24. doi:10.1016/j.soncn.2016.05.011.
Boyd, Scott D, and James E Crowe Jr. "Deep sequencing and human antibody repertoire analysis." Current opinion in immunology vol. 40 (2016): 103-9. doi:10.1016/j.coi.2016.03.008.
Conroy, Paul J et al. "Antibodies: From novel repertoires to defining and refining the structure of biologically important targets." Methods (San Diego, Calif.) vol. 116 (2017): 12-22. doi:10.1016/j.ymeth.2017.01.003.
Damschroder, Melissa M et al. "Analysis of human and primate CD2 molecules by protein sequence and epitope mapping with anti-human CD2 antibodies." Molecular immunology vol. 41,10 (2004): 985-1000. doi:10.1016/j.molimm.2004.05.004.
Ferrara, Fortunato et al. "Recombinant renewable polyclonal antibodies." mAbs vol. 7,1 (2015): 32-41. doi:10.4161/19420862.2015.989047.
Kanyavuz, Alexia et al. "Breaking the law: unconventional strategies for antibody diversification." Nature reviews. Immunology vol. 19,6 (2019): 355-368. doi:10.1038/s41577-019-0126-7.
Khan, Lubina et al. "Cross-neutralizing anti-HIV-1 human single chain variable fragments(scFvs) against CD4 binding site and N332 glycan identified from a recombinant phage library." Scientific reports vol. 7 45163. Mar. 23, 2017, doi:10.1038/srep45163.
Konitzer, Jennifer D et al. "Generation of a highly diverse panel of antagonistic chicken monoclonal antibodies against the GIP receptor." mAbs vol. 9,3 (2017): 536-549. doi: 10.1080/19420862.2016.1276683.
Lee, Jiwon et al. "Molecular-level analysis of the serum antibody repertoire in young adults before and after seasonal influenza vaccination." Nature medicine vol. 22,12 (2016): 1456-1464. doi:10.1038/nm.4224.
Linsley PS, et al. "The clinical utility of inhibiting CD28-mediated costimulation," Immunol Rev. May 2009;229(1):307-21.
Parola, Cristina et al. "Integrating high-throughput screening and sequencing for monoclonal antibody discovery and engineering." Immunology vol. 153,1 (2018): 31-41. doi:10.1111/imm.12838.
Pettinello, Rita, and Helen Dooley. "The immunoglobulins of cold-blooded vertebrates." Biomolecules vol. 4,4 1045-69. Nov. 24, 2014, doi:10.3390/biom4041045.
Rizvi, N.A., et al., "Mutational landscape determines sensitivity to PD-1 blockade in non-small cell lung cancer," Science, vol. 348; No. 6230; 124-148 (2015).
Shashidharamurthy, Rangaiah et al. "Analysis of cross-species IgG binding to human and mouse Fcgamma receptors (FcγRs) (138.29)." Journal of Immunology 184 (2010): n. pag. Abstract only.

Shashidharamurthy, Rangaiah et al. "Dynamics of the interaction of human IgG subtype immune complexes with cells expressing R and H allelic forms of a low-affinity Fc gamma receptor CD32A." Journal of immunology (Baltimore, Md. : 1950) vol. 183,12 (2009): 8216-24. doi:10.4049/jimmunol.0902550.
Sheehan, Jared, and Wayne A Marasco. "Phage and Yeast Display." Microbiology spectrum vol. 3,1 (2015): AID-0028-2014. doi:10.1128/microbiolspec.AID-0028-2014.
Van Regenmortel, Marc H V. "Development of a Preventive HIV Vaccine Requires Solving Inverse Problems Which Is Unattainable by Rational Vaccine Design." Frontiers in immunology vol. 8 2009. Jan. 12, 2018, doi:10.3389/fimmu.2017.02009.
UniProtKB/Swiss-Prot Q9H7M9.3 V-type immunoglobulin domain-containing suppressor of T-cell activation, 2019, 6 pages.
Vafa, Omid et al. "An engineered Fc variant of an IgG eliminates all immune effector functions via structural perturbations." Methods (San Diego, Calif.) vol. 65,1 (2014): 114-26. doi:10.1016/j.ymeth.2013.06.035.
Wang, L. et al., "Vista, a novel mouse Ig superfamily ligand that negatively regulates T cell response," J. Exp. Med. Mar. 7, 2011, vol. 208. No. 3, pp. 577-592.
Wolff, A.C., et al., "American Society of Clinical Oncology/College of American Pathologists Guideline Recommendations for Human Epidermal Growth Factor Receptor 2 Testing in Breast Cancer," Arch Pathol Lab Med, vol. 131; 18-43 (2007).
Allen, Martin J et al. "Interchain disulfide bonding in human IgG2 antibodies probed by site-directed mutagenesis." Biochemistry vol. 48,17 (2009): 3755-66. doi:10.1021/bi8022174.
Lightle, Sandra et al. "Mutations within a human IgG2 antibody form distinct and homogeneous disulfide isomers but do not affect Fc gamma receptor or C1q binding." Protein science : a publication of the Protein Society vol. 19,4 (2w010): 753-62. doi:10.1002/pro.352.
Nowak, Elizabeth C et al. "Immunoregulatory functions of VISTA." Immunological reviews vol. 276,1 (2017): 66-79. doi:10.1111/imr.12525.
Papaconstantinou, Harry T, and J Scott Thomas. "Bacterial colitis." Clinics in colon and rectal surgery vol. 20,1 (2007): 18-27. doi:10.1055/s-2007-970196.
Tecklenborg, J et al. "The role of the immune system in kidney disease." Clinical and experimental immunology vol. 192,2 (2018): 142-150. doi:10.1111/cei.13119.
Wang, Xinhua et al. "IgG Fc engineering to modulate antibody effector functions." Protein & cell vol. 9,1 (2018): 63-73. doi:10.1007/s13238-017-0473-8.
White, Ann L et al. "Conformation of the human immunoglobulin G2 hinge imparts superagonistic properties to immunostimulatory anticancer antibodies." Cancer cell vol. 27,1 (2015): 138-48. doi:10.1016/j.ccell.2014.11.001.
Ben-Zvi, Lior et al. "Diagnosis and Management of Infectious Arthritis in Children." Current infectious disease reports vol. 21,7 23. May 29, 2019, doi:10.1007/s11908-019-0678-5.
Hid Cadena, Rebeca et al. "Decreased Expression of Negative Immune Checkpoint VISTA by CD4+ T Cells Facilitates T Helper 1, T Helper 17, and T Follicular Helper Lineage Differentiation in GCA." Frontiers in immunology vol. 10 1638. Jul. 16, 2019, doi:10.3389/fimmu.2019.01638.
Xu, Wenwen et al. "Immune-Checkpoint Protein VISTA Regulates Antitumor Immunity by Controlling Myeloid Cell-Mediated Inflammation and Immunosuppression." Cancer immunology research vol. 7,9 (2019): 1497-1510. 1oi:10.1158/2326-6066.CIR-18-0489.
Konishi J, et al. "B7-H1 expression on non-small cell lung cancer cells and its relationship with tumor-infiltrating lymphocytes and their PD-1 expression," Clin Cancer Res. Aug. 1, 2004;10(15):5094-100.
Topalian SL, et al. "Safety, activity, and immune correlates of anti-PD-1 antibody in cancer," N Engl J Med. Jun. 28, 2012;366(26):2443-54.
Ladjemi MZ, et al. "Anti-HER2 vaccines: new prospects for breast cancer therapy," Cancer Immunol Immunother. Sep. 2010;59(9):1295-312.

(56) References Cited

OTHER PUBLICATIONS

Gupta S, et al. "Systemic Immunotherapy for Urothelial Cancer: Current Trends and Future Directions," Cancers (Basel). Jan. 27, 2017;9(2).
Lawrence MS, et al. "Mutational heterogeneity in cancer and the search for new cancer-associated genes," Nature. Jul. 11, 2013;499(7457):214-218.
Beers SA, et al. "Influence of immunoglobulin isotype on therapeutic antibody function," Blood. Mar. 3, 2016;127(9):1097-101.
Overdijk MB, et al. "Crosstalk between human IgG isotypes and murine effector cells," J Immunol. Oct. 1, 2012;189(7):3430-8.
Mor F, et al. "Identification of aldolase as a target antigen in Alzheimer's disease," J Immunol. Sep. 1, 2005; 175(5):3439-45.
Burgers WA, et al. "The challenges of HIV vaccine development and testing," Best Pract Res Clin Obstet Gynaecol. Apr. 2005;19(2):277-91.
Chevalier MF, et al. "The split personality of regulatory T cells in HIV infection," Blood. Jan. 3, 2013;121(1):29-37.
Quinn MA, et al. "How do you diagnose rheumatoid arthritis early?" Best Pract Res Clin Rheumatol. Mar. 2001;15(1):49-66.
"Progress in Autoimmune Diseases Research," U.S. Department of Health and Human Services, National Institutes of Health, National Institute of Allergy and Infectious Diseases, Mar. 2005. 146 pages.
"MS the Disease," National Multiple Sclerosis Society, https://www.nationalmssociety.org/About-the-Society/Press-Room/MS-the-Disease, 2019. 5 pages.
Lapierre P, et al. "Regulatory T Cells in Autoimmune and Viral Chronic Hepatitis," J Immunol Res. 2015;2015:479703.
Amancha PK, et al. "In vivo blockade of the programmed cell death-1 pathway using soluble recombinant PD-1-Fc enhances CD4+ and CD8+ T cell responses but has limited clinical benefit," J Immunol. Dec. 15, 2013;191(12):6060-70.
Bagley RG, et al. "sFLT01: a novel fusion protein with antiangiogenic activity," Mol Cancer Ther. Mar. 2011;10(3):404-15.
Colman PM. "Effects of amino acid sequence changes on antibody-antigen interactions," Res Immunol. Jan. 1994;145(1):33-6.
Curis, Inc. "A Study of CA-170 (Oral PD-L1, PD-L2 and VISTA Checkpoint Antagonist) in Patients With Advanced Tumors and Lymphomas," U.S. National Library of Medicine, ClinicalTrials.gov; (https://clinicaltrials.gov) 2018. 8 pages.
Deng J, et al. "A New VISTA on combination therapy for negative checkpoint regulator blockade," J Immunother Cancer. Dec. 20, 2016;4:86.
Flies DB, et al. "Cutting edge: A monoclonal antibody specific for the programmed death-1 homolog prevents graft-versus-host disease in mouse models," J Immunol. Aug. 15, 2011;187(4):1537-41.
Gao J, et al. "VISTA is an inhibitory immune checkpoint that is increased after ipilimumab therapy in patients with prostate cancer," Nat Med. May 2017;23(5):551-555.
Janssen Clinical Trials "A Study of Safety, Pharmacokinetics, Pharmacodynamics of JNJ-61610588 in Participants With Advanced Cancer," U.S. National Library of Medicine, ClinicalTrials.gov; (https://clinicaltrials.gov) 2017. 9 pages.
Jones TD, et al. "The development of a modified human IFN-alpha2b linked to the Fc portion of human IgG1 as a novel potential therapeutic for the treatment of hepatitis C virus infection," J Interferon Cytokine Res. Sep. 2004;24(9):560-72.
Le Mercier I, et al. "Beyond CTLA-4 and PD-1, the Generation Z of Negative Checkpoint Regulators," Front Immunol. Aug. 21, 2015;6:418.
Li CH, et al. "beta-Endorphin omission analogs: dissociation of immunoreactivity from other biological activities," Proc Natl Acad Sci U S A. Jun. 1980;77(6):3211-4.
Iliopoulos, D, et al. "The negative costimulatory molecule PD-1 modulates the balance between immunity and tolerance via miR-21," Eur J Immunol 2011. 41: 1754-1763.
Mezo AR, et al. "Atrial natriuretic peptide-Fc, ANP-Fc, fusion proteins: semisynthesis, in vitro activity and pharmacokinetics in rats," Bioconjug Chem. Mar. 21, 2012;23(3):518-26.
Nielsen MB, et al. "Melanoma vaccines: the paradox of T cell activation without clinical Yesponse," Cancer Chemother Pharmacol. 2000;46 Suppl:S62-6.
Nowak EC, et al. "Immunoregulatory functions of VISTA," Immunol Rev. Mar. 2017;276(1):66-79.
Qin W, et al. "Fusion protein of CDR mimetic peptide with Fc inhibit TNF-alpha induced cytotoxicity," Mol Immunol. Feb. 2006;43(6):660-6.
Rathore R, et al. "Current State of Tolerance: The Holy Grail," Arch Clin Nephrol 3(2): 057-063.
Sasikumar P, et al. "Abstact B006: Functional antagonism of VISG8-mediated immune suppression by oral VISTA agents," Abstacts AACR-NCI-EORTC International Conference: Molecular Targets and Cancer Therapeutics; Oct. 2017. 5 pages.
Sequence Alignment, 2010, 1 page.
Sequence alignment, 2015, 3 pages.
Transmembrane Region Prediction, 2018, 16 pages.
Wang G, et al. "The effects of PDL-Ig on collagen-induced arthritis," Rheumatol Int. Apr. 2011;31(4):513-9.
Altschul SF, et al. "Basic local alignment search tool," J Mol Biol. Oct. 5, 1990;215(3):403-10.
Altschul SF, et al. "Gapped BLAST and PSI-BLAST: a new generation of protein database search programs," Nucleic Acids Res. Sep. 1, 1997;25(17):3389-402.
Beilharz MW, et al. "Timed ablation of regulatory CD4+ T cells can prevent murine AIDS progression," J Immunol. Apr. 15, 2004;172(8):4917-25.
Bowen JL, et al. "Innate immune CD11b+Gr-1+ cells, suppressor cells, affect the immune response during Theiler's virus-induced demyelinating disease," J Immunol. Dec. 1, 2009;183(11):6971-80.
Brys L, et al. "Reactive oxygen species and 12/15-lipoxygenase contribute to the antiproliferative capacity of alternatively activated myeloid cells elicited during helminth infection," J Immunol. May 15, 2005;174(10):6095-104.
Chen S, et al. "Immunosuppressive functions of hepatic myeloid-derived suppressor cells of normal mice and in a murine model of chronic hepatitis B virus," Clin Exp Immunol. Oct. 2011;166(1):134-42.
Flicek P, et al. "Ensembl 2008," Nucleic Acids Res. Jan. 2008;36(Database issue):D707-14.
Garg A, et al. "HIV type 1 gp120-induced expansion of myeloid derived suppressor cells is dependent on interleukin 6 and suppresses immunity," J Infect Dis. Feb. 1, 2014;209(3):441-51.
Green KA, et al. "Antibody to the ligand for CD40 (gp39) inhibits murine AIDS-associated splenomegaly, hypergammaglobulinemia, and immunodeficiency in disease-susceptible C57BL/6 mice," J Virol. Apr. 1996;70(4):2569-75.
Green KA, et al. "Myeloid-derived suppressor cells in murine retrovirus-induced AIDS inhibit T- and B-cell responses in vitro that are used to define the immunodeficiency," J Virol. Feb. 2013;87(4):2058-71.
Hauser N, et al. "Native cartilage matrix protein (CMP). A compact trimer of subunits assembled via a coiled-coil alpha-helix," J Biol Chem. Oct. 14, 1994;269(41):25747-53.
Iliopoulos D, et al. "The negative costimulatory molecule PD-1 modulates the balance between immunity and tolerance via miR-21," Eur J Immunol. Jun. 2011;41(6):1754-63.
Jeisy-Scott V, et al. "Increased MDSC accumulation and Th2 biased response to influenza A virus infection in the absence of TLR7 in mice," PLoS One. 2011;6(9):e25242.
Klinken SP, et al. "Evolution of B cell lineage lymphomas in mice with a retrovirus-induced immunodeficiency syndrome, MAIDS," J Immunol. Feb. 15, 1988;140(4):1123-31.
LaFace D, et al. "Meeting report: regulatory myeloid cells," Int Immunopharmacol. Jul. 2011;11(7):780-2.
Laubach VE, et al. "Mice lacking inducible nitric oxide synthase are not resistant to Tipopolysaccharide-induced death," Proc Natl Acad Sci U S A. Nov. 7, 1995;92(23):10688-92.
Lerner EA. "How to make a hybridoma," Yale J Biol Med. Sep.-Oct. 1981;54(5):387-402.
Li W, et al. "Immunotherapy of murine retrovirus-induced acquired immunodeficiency by CD4 T regulatory cell depletion and PD-1 blockade," J Virol. Dec. 2011;85(24):13342-53.

(56) References Cited

OTHER PUBLICATIONS

Li W, et al. "The role of CD4 T cells in the pathogenesis of murine AIDS," J Virol. Jun. 2006;80(12):5777-89.
Macatangay BJ, et al. "MDSC: a new player in HIV immunopathogenesis," AIDS. Jul. 31, 2012;26(12):1567-9.
Melief CJ. "Cancer immunotherapy by dendritic cells," Immunity. Sep. 19, 2008;29(3):372-83.
Mencacci A, et al. "CD80+Gr-1+ myeloid cells inhibit development of antifungal Th1 immunity in mice with candidiasis," J Immunol. Sep. 15, 2002;169(6):3180-90.
Merrifield B. "Concept and early development of solid-phase peptide synthesis," Methods Enzymol. 1997;289:3-13.
Milstein C, et al. "Hybrid hybridomas and their use in immunohistochemistry," Nature. Oct. 6-12, 1983;305(5934):537-40.
Mingozzi F, et al. "Immune responses to AAV vectors: overcoming barriers to successful gene therapy," Blood. Jul. 4, 2013;122(1):23-36.
Monteiro RC, et al. "Molecular heterogeneity of Fc alpha receptors detected by receptor-specific monoclonal antibodies," J Immunol. Mar. 15, 1992;148(6):1764-70.
Moore GJ. "Designing peptide mimetics," Trends Pharmacol Sci. Apr. 1994;15(4):124-9.
Muller PY, et al. "Safety assessment and dose selection for first-in-human clinical trials with immunomodulatory monoclonal antibodies," Clin Pharmacol Ther. Mar. 2009;85(3):247-58.
Nakano H, et al. "Blood-derived inflammatory dendritic cells in lymph nodes stimulate acute T helper type 1 immune responses," Nat Immunol. Apr. 2009;10(4):394-402.
Nalbandian A, et al. "Interleukin-17 and systemic lupus erythematosus: current concepts," Clin Exp Immunol. Aug. 2009;157(2):209-15.
Nathwani AC, et al. "Adenovirus-associated virus vector-mediated gene transfer in hemophilia B," N Engl J Med. Dec. 22, 2011;365(25):2357-65.
Nesbeth YC, et al. "CD4+ T cells elicit host immune responses to MHC class II-negative ovarian cancer through CCL5 secretion and CD40-mediated licensing of dendritic cells," J Immunol. May 15, 2010;184(10):5654-62.
Neuberger MS, et al. "A hapten-specific chimaeric IgE antibody with human physiological effector function," Nature. Mar. 21-27, 1985;314(6008):268-70.
Niklinski J, et al. "Molecular genetic abnormalities in premalignant lung lesions: biological and clinical implications," Eur J Cancer Prev. Jun. 2001;10(3):213-26.
Nishikawa H, et al. "Regulatory T cells in tumor immunity," Int J Cancer. Aug. 15, 2010;127(4):759-67.
Nygren H. "Conjugation of horseradish peroxidase to Fab fragments with different homobifunctional and heterobifunctional cross-linking reagents. A comparative study," J Histochem Cytochem. May 1982;30(5):407-12.
Ohtsuka E, et al. "An alternative approach to deoxyoligonucleotides as hybridization probes by insertion of deoxyinosine at ambiguous codon positions," J Biol Chem. Mar. 10, 1985;260(5):2605-8.
Okazaki T, et al. "The PD-1-PD-L pathway in immunological tolerance," Trends Immunol. Apr. 2006;27(4):195-201.
Ortler S, et al. "B7-H1 restricts neuroantigen-specific T cell responses and confines inflammatory CNS damage: implications for the lesion pathogenesis of multiple sclerosis," Eur J Immunol. Jun. 2008;38(6):1734-44.
Ostrand-Rosenberg S, et al. "Myeloid-derived suppressor cells: linking inflammation and cancer," J Immunol. Apr. 15, 2009;182(8):4499-506.
Ostrand-Rosenberg S. "Myeloid-derived suppressor cells: more mechanisms for inhibiting antitumor immunity," Cancer Immunol Immunother. Oct. 2010;59(10):1593-600.
Ottavi A, et al. "An improved method to obtain a single recombinant vasoactive intestinal peptide (VIP) analog," Biochimie. Apr. 1998;80(4):289-93.

Peranzoni E, et al. "Myeloid-derived suppressor cell heterogeneity and subset definition," Curr Opin Immunol. Apr. 2010;22(2):238-44.
Piccirillo CA, et al. "Naturally-occurring CD4+CD25+ immunoregulatory T cells: central players in the arena of peripheral tolerance," Semin Immunol. Apr. 2004;16(2):81-8.
Piccotti JR, et al. "T-cell-dependent antibody response: assay development in cynomolgus monkeys," J Immunotoxicol. Oct. 1, 2005;2(4):191-6.
Pilat N, et al. "Costimulatory pathways in transplantation," Semin Immunol. Aug. 2011;23(4):293-303.
Podojil JR, et al. "B7-H4Ig inhibits mouse and human T-cell function and treats EAE via IL-10/Treg-dependent mechanisms," J Autoimmun. Aug. 2013;44:71-81.
Polyak SW, et al. "Introduction of spacer peptides N-terminal to a cleavage recognition motif in recombinant fusion proteins can improve site-specific cleavage," Protein Eng. Jun. 1997;10(6):615-9.
Ponten J. "Cell biology of precancer," Eur J Cancer. Oct. 2001;37 Suppl 8:S97-113.
Qin A, et al. "Expansion of monocytic myeloid-derived suppressor cells dampens T cell function in HIV-1-seropositive individuals," J Virol. Feb. 2013;87(3):1477-90.
Rowe WP, et al. "Plaque assay techniques for murine leukemia viruses," Virology. Dec. 1970;42(4):1136-9.
Sakaguchi S, et al. "Immunologic tolerance maintained by CD25+ CD4+ regulatory T cells their common role in controlling autoimmunity, tumor immunity, and transplantation tolerance," Immunol Rev. Aug. 2001;182:18-32.
Simard C, et al. "Studies of the susceptibility of nude, CD4 knockout, and SCID mutant mice to the disease induced by the murine AIDS defective virus," J Virol. Apr. 1997;71(4):3013-22.
Smith JH, et al. "Detection of *Mycobacterium tuberculosis* directly from sputum by using a prototype automated Q-beta replicase assay," J Clin Microbiol. Jun. 1997;35(6):1477-83.
Takamura S, et al. "Premature terminal exhaustion of Friend virus-specific effector CD8+ T cells by rapid induction of multiple inhibitory receptors," J Immunol. May 1, 2010;184(9):4696-707.
Velu V, et al. "Enhancing SIV-specific immunity in vivo by PD-1 blockade," Nature. Mar. 12, 2009;458(7235):206-10.
Walker JD, et al. "Oncolytic herpes simplex virus 1 encoding 15-prostaglandin dehydrogenase mitigates immune suppression and reduces ectopic primary and metastatic breast cancer in mice," J Virol. Jul. 2011;85(14):7363-71.
Weintraub H., et al. "Anti-sense RNA as a molecular tool for] genetic analysis," Trends in Genetics, 1985, pp. 22-25.
Willmon C, et al. "Vesicular stomatitis virus-induced immune suppressor cells generate antagonism between intratumoral oncolytic virus and cyclophosphamide," Mol Ther. Jan. 2011;19(1):140-9.
Wolchok JD, et al. "Nivolumab plus ipilimumab in advanced melanoma," N Engl J Med. Jul. 11, 2013;369(2):122-33.
Yetter RA, et al. "CD4+ T cells are required for development of a murine retrovirus-induced immunodeficiency syndrome (MAIDS)," J Exp Med. Aug. 1, 1988;168(2):623-35.
Youn JI, et al. "The biology of myeloid-derived suppressor cells: the blessing and the curse of morphological and functional heterogeneity," Eur J Immunol. Nov. 2010;40(11):2969-75.
Zelinskyy G, et al. "The regulatory T-cell response during acute retroviral infection is locally defined and controls the magnitude and duration of the virus-specific cytotoxic T-cell response," Blood. Oct. 8, 2009;114(15):3199-207.
Sheehan, K, et al. "The relationship between cyclooxygenase-2 expression and colorectal cancer," JAMA, 1999. 282: p. 1254-7.
Shevach EM. "Regulatory T cells in autoimmmunity," Annu Rev Immunol. 2000;18:423-49.
Shevach, E. M., CD4+ CD25+ suppressor T cells: more questions than answers. Nat Rev Immunol, 2002. 2(6): p. 389-400.
Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.

(56) References Cited

OTHER PUBLICATIONS

Shields RL, et al. "Lack of fucose on human IgG1 N-linked oligosaccharide improves binding to human Fcgamma RIII and antibody-dependent cellular toxicity," J Biol Chem. Jul. 26, 2002;277(30):26733-40.
Shimizu J, et al. "Stimulation of CD25(+)CD4(+) regulatory T cells through GITR breaks immunological self-tolerance," Nat Immunol. Feb. 2002;3(2):135-42.
Shortman, K. et al. "Steady-state and inflammatory dendritic-cell development," Nat Rev Immunol, 2007. 7(1): p. 19-30.
Shulman M, et al. "A better cell line for making hybridomas secreting specific antibodies," Nature. Nov. 16, 1978;276(5685):269-70.
Sica GL, et al. "B7-H4, a molecule of the B7 family, negatively regulates T cell immunity," Immunity. Jun. 2003;18(6):849-61.
Sizemore DR, et al. "Attenuated Shigella as a DNA delivery vehicle for DNA-mediated immunization," Science. Oct. 13, 1995;270(5234):299-302.
Skehel JJ, et al. "Coiled coils in both intracellular vesicle and viral membrane fusion," Cell. Dec. 23, 1998;95(7):871-4.
Smith DB, et al. "Single-step purification of polypeptides expressed in *Escherichia coli* as fusions with glutathione S-transferase," Gene. Jul. 15, 1988;67(1):31-40.
Smith GE, et al. "Production of human beta interferon in insect cells infected with a baculovirus expression vector," Mol Cell Biol. Dec. 1983;3(12):2156-65.
Smith JH, et al. "Performance of an automated Q-beta replicase amplification assay for *Mycobacterium tuberculosis* in a clinical trial," J Clin Microbiol. Jun. 1997;35(6):1484-91.
Smith LJ, et al. "Human interleukin 4. The solution structure of a four-helix bundle protein," J Mol Biol. Apr. 20, 1992;224(4):899-904.
Son YI, et al. "A novel bulk-culture method for generating mature dendritic cells from mouse bone marrow cells," J Immunol Methods. Apr. 1, 2002;262(1-2):145-57.
Spatola AF, et al. "Structure-activity relationships of enkephalins containing serially replaced thiomethylene amide bond surrogates," Life Sci. Apr. 7, 1986;38(14):1243-9.
Steinman, R. M. et al. "Tolerogenic dendritic cells," Annu Rev Immunol, 2003. 21: p. 685-711.
Stewart MJ, et al. "Gene transfer in vivo with DNA-liposome complexes: safety and acute toxicity in mice," Hum Gene Ther. Jun. 1992;3(3):267-75.
Studier FW, et al. "Use of T7 RNA polymerase to direct expression of cloned genes," Methods Enzymol. 1990;185:60-89.
Su AI, et al. "Large-scale analysis of the human and mouse transcriptomes," Proc Natl Acad Sci U S A. Apr. 2, 2002;99(7):4465-70.
Suh, W. K., et al. "The B7 family member B7-H3 preferentially down-regulates T helper type 1-mediated immune responses," Nat Immunol 2003. 4: 899-906.
Sun LK, et al. "Chimeric antibody with human constant regions and mouse variable regions directed against carcinoma-associated antigen 17-1A," Proc Natl Acad Sci USA. Jan. 1987;84(1):214-8.
Sunderkotter, C., et al., "Subpopulations of mouse blood monocytes differ in maturation stage and inflammatory response," J Immunol, 2004. 172(7): p. 4410-7.
Tacke, F. et al. "Migratory fate and differentiation of blood monocyte subsets," Immunobiology, 2006. 211(6-8): p. 609-18.
Tafuri A, et al. "ICOS is essential for effective T-helper-cell responses," Nature. Jan. 4, 2001;409(6816):105-9.
Takamatsu N, et al. "Expression of bacterial chloramphenicol acetyltransferase gene in tobacco plants mediated by TMV-RNA," EMBO J. Feb. 1987;6(2):307-11.
Takeda S, et al. "Construction of chimaeric processed immunoglobulin genes containing mouse variable and human constant region sequences," Nature. Apr. 4-10, 1985;314(6010):452-4.
Tarhini, A., E. Lo, and D. R. Minor, Releasing the brake on the immune system: ipilimumab in melanoma and other tumors. Cancer Biother Radiopharm, 2010. 25(6): p. 601-13.

Taylor LD, et al. "A transgenic mouse that expresses a diversity of human sequence heavy and light chain immunoglobulins," Nucleic Acids Res. Dec. 11, 1992;20(23):6287-95.
Taylor LD, et al. "Human immunoglobulin transgenes undergo rearrangement, somatic mutation and class switching in mice that lack endogenous IgM," Int Immunol. Apr. 1994;6(4):579-91.
Taylor WR. "The classification of amino acid conservation," J Theor Biol. Mar. 21, 1986;119(2):205-18.
Teft WA, et al. "A molecular perspective of CTLA-4 function," Annu Rev Immunol. 2006;24:65-97.
Terawaki, S., "Specific and high-affinity binding of tetramerized PD-LI extracellular domain to PD-I-expressing cells: possible application to enhance T cell function," Int Immunol 2007. 19: 881-890.
Thompson JA, et al. "A phase 1 trial of CD3/CD28-activated T cells (Xcellerated T cells) and interleukin-2 in patients with metastatic renal cell carcinoma," Clin Cancer Res. Sep. 1, 2003;9(10 Pt 1):3562-70.
Thompson JD, et al. "Clustal W: improving the sensitivity of progressive multiple sequence alignment through sequence weighting, position-specific gap penalties and weight matrix choice," Nucleic Acids Res. Nov. 11, 1994;22(22):4673-80.
Thorpe et al., "The Preparation And Cytotoxic Properties Of Antibody-Toxin Conjugates", Immunol. Rev., 62: 119-58 (1982).
Tivol EA, et al. "Loss of CTLA-4 leads to massive lymphoproliferation and fatal multiorgan tissue destruction, revealing a critical negative regulatory role of CTLA-4," Immunity. Nov. 1995;3(5):541-7.
Tomizuka K, et al. "Double trans-chromosomic mice: maintenance of two individual human chromosome fragments containing Ig heavy and kappa loci and expression of fully human antibodies," Proc Natl Acad Sci U S A. Jan. 18, 2000;97(2):722-7.
Tomlinson, et al. (1992) "The Repertoire of Human Germline VH Sequences Reveals about Fifty Groups of VH Segments with Different Hypervariable Loops" J. Mol. Biol. 227: 776-798.
Townsend SE, et al. "Tumor rejection after direct costimulation of CD8+ T cells by B7-transfected melanoma cells," Science. Jan. 15, 1993;259(5093):368-70.
Trail PA, et al. "Monoclonal antibody drug immunoconjugates for targeted treatment of cancer," Cancer Immunol Immunother. May 2003;52(5):328-37.
Traunecker A, et al. "Bispecific single chain molecules (Janusins) target cytotoxic Tymphocytes on HIV infected cells," EMBO J. Dec. 1991;10(12):3655-9.
Tuaillon N, et al. "Human immunoglobulin heavy-chain minilocus recombination in transgenic mice: gene-segment use in mu and gamma transcripts," Proc Natl Acad Sci U S A. Apr. 15, 1993;90(8):3720-4.
Tuaillon N, et al. "Biased utilization of DHQ52 and JH4 gene segments in a human Ig transgenic minilocus is independent of antigenic selection," J Immunol. Mar. 15, 1994;152(6):2912-20.
Tutt A, et al. "Trispecific F(ab')3 derivatives that use cooperative signaling via the TCR/CD3 complex and CD2 to activate and redirect resting cytotoxic T cells," J Immunol. Jul. 1, 1991;147(1):60-9.
Umaña P, et al. "Engineered glycoforms of an antineuroblastoma IgG1 with optimized antibody-dependent cellular cytotoxic activity," Nat Biotechnol. Feb. 1999;17(2):176-80.
Umezawa F, et al. "Liposome targeting to mouse brain: mannose as a recognition marker," Biochem Biophys Res Commun. Jun. 30, 19880;153(3):1038-44.
Uy R, et al. "Posttranslational covalent modification of proteins," Science. Dec. 2, 1977;198(4320):890-6.
Vaccaro C, et al. "Engineering the Fc region of immunoglobulin G to modulate in vivo antibody levels," Nature Biotechnology. 2005;23(10):1283-8.
Van Elsas A, et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," J Exp Med. Aug. 2, 1999;190(3):355-66.

(56) References Cited

OTHER PUBLICATIONS

Van Wauwe JP, et al. "OKT3: a monoclonal anti-human T lymphocyte antibody with potent mitogenic properties," The Journal of Immunology. 1980;124(6):2708-13.
Verhoeyen M, et al. "Reshaping human antibodies: grafting an antilysozyme activity," Science. Mar. 25, 1988;239(4847):1534-6.
Via CS. "Advances in lupus stemming from the parent-into-Fl model". Trends Immunol., Jun. 2010.31(6):236-45).
Wada K, et al. "Codon usage tabulated from the GenBank genetic sequence data," Nucleic Acids Res. May 11, 1992;20 Suppl:2111-8.
Wadia JS, et al. "Protein transduction technology," Curr Opin Biotechnol. Feb. 2002;13(1):52-6.
Walch A, et al. "Microdissection of tissue sections: application to the molecular genetic characterisation of premalignant lesions," Pathobiology. Jan.-Feb. 2000;68(1):9-17.
Wallace DJ, et al. "Long-Term Safety and Efficacy of Epratuzumab in the Treatment of Moderate-to-Severe Systemic Lupus Erythematosus: Results From an Open-Label Extension Study," Arthritis Care Res (Hoboken). Apr. 2016;68(4):534-43.
Wang HC, et al. "Maximum immunobioactivity of murine small intestinal intraepithelial Tymphocytes resides in a subpopulation of CD43+ T cells," J Immunol. Nov. 15, 2004;173(10):6294-302.
Wang H-X, "Immune mechanisms of Concanavalin A model of autoimmune hepatitis," World Journal of Gastroenterology: WJG. 2012;18(2):119-25.
Wang L, et al. "Disruption of the immune-checkpoint VISTA gene imparts a proinflammatory phenotype with predisposition to the development of autoimmunity," Proc Natl Acad Sci U S A. Oct. 14, 2014;111(41):14846-51.
Wang, L., et al., "Programmed death 1 ligand signaling regulates the generation of adaptive Foxp3+CD4+ regulatory T cells," Proc Natl Acad Sci USA, 2008. 105(27): p. 9331-6.
Wang, X., "B7-H4 induces donor-specific tolerance in mouse islet allografts," Cell Transplant 2012. 21: 99-111.
Wang, X., "B7-H4 Treatment of T Cells Inhibits ERK, JN K, p38, and AKT Activation," PLoS One 2012. 7: e28232.
Ward ES, et al. "Binding activities of a repertoire of single immunoglobulin variable domains secreted from *Escherichia coli*," Nature. Oct. 12, 1989;341(6242):544-6.
Waterhouse P, et al. "Lymphoproliferative disorders with early lethality in mice deficient in Ctla-4," Science. Nov. 10, 1995;270(5238):985-8.
Weber, J., "Immune checkpoint proteins: a new therapeutic paradigm for cancer—preclinical background: CTLA-4 and PD-1 blockade," Semin Oncol, 2010. 37(5): p. 430-9.
Weiner GJ. "Building better monoclonal antibody-based therapeutics," Nat Rev Cancer. 2015;15(6):361-70.
Weissmuller S, "TGN1412 Induces Lymphopenia and Human Cytokine Release in a Humanized Mouse Model," PloS One. 2016;II(3):e0149093.
Welling GW, et al. "Prediction of sequential antigenic regions in proteins," FEBS Lett. Sep. 2, 1985;188(2):215-8.
Wetmur JG. "DNA probes: applications of the principles of nucleic acid hybridization," Crit Rev Biochem Mol Biol. 1991;26(3-4):227-59.
White et al., (2015), "Conformation of the human immunoglobulin G2 hinge imparts superagonistic properties to immunostimulatory anticancer antibodies", Cancer Cell, 27(1), 138-148.
Wilcox, R. A., "Cancer-associated myeloproliferation: old association, new therapeutic target," Mayo Clin Proc, 2010. 85(7): p. 656-63.
Wiley RA, et al. "Peptidomimetics derived from natural products," Med Res Rev. May 1993;13(3):327-84.
Williams G, et al. "Dissection of the extracellular human interferon gamma receptor alpha-chain into two immunoglobulin-like domains. Production in an *Escherichia coli* thioredoxin gene fusion expression system and recognition by neutralizing antibodies," Biochemistry. Feb. 7, 1995;34(5):1787-97.
Wilmut I, et al. "Viable offspring derived from fetal and adult mammalian cells," Nature. Feb. 24, 1997;385(6619):810-3.

Wing, K., et al., "CTLA-4 control over Foxp3+ regulatory T cell function," Science, 2008. 322(5899): p. 271-5.
Winoto A, et al. "A novel, inducible and T cell-specific enhancer located at the 3' end of the T cell receptor alpha locus," Embo J. Mar. 1989;8(3):729-33.
Winter G, et al. "Man-made antibodies," Nature. Jan. 24, 1991;349(6307):293-9.
Wojcik J, et al. "Prediction, assessment and validation of protein interaction maps in bacteria," J Mol Biol. Nov. 1, 2002;323(4):763-70.
Wood CR, et al. "The synthesis and in vivo assembly of functional antibodies in yeast," Nature. Apr. 4-10, 1985;314(6010):446-9.
Wood KJ, et al. "Regulatory T cells in transplantation tolerance," Nat Rev Immunol. Mar. 2003;3(3):199-210.
Wu DY, et al. "The ligation amplification reaction (LAR)— amplification of specific DNA sequences using sequential rounds of template-dependent ligation," Genomics. May 1989;4(4):560-9.
Wu S, et al. "Development and application of 'phosphoflow' as a tool for immunomonitoring," Expert Rev Vaccines. 2010;9(6):631-43.
Yamaguchi, T. et al. "Regulatory T cells in immune surveillance and treatment of cancer," Semin Cancer Biol, 2006. 16(2): p. 115-23.
Yamane-Ohnuki N, et al. "Establishment of FUT8 knockout Chinese hamster ovary cells: an ideal host cell line for producing completely defucosylated antibodies with enhanced antibody-dependent cellular cytotoxicity," Biotechnol Bioeng. Sep. 5, 2004;87(5):614-22.
Yamaura, K., "In vivo function of immune inhibitory molecule B7-H4 in alloimmune Yesponses," Am J Transplant 2010. 10: 2355-2362.
Yeh MY, et al. "A cell-surface antigen which is present in the ganglioside fraction and shared by human melanomas," Int J Cancer. Mar. 15, 1982;29(3):269-75.
Yeh MY, et al. "Cell surface antigens of human melanoma identified by monoclonal antibody," Proc Natl Acad Sci U S A. Jun. 1979;76(6):2927-31.
M, K. H., et al. "Fine tuning the immune response through B7-H3 and B7-H4," Immunol Rev, 2009. 229(1): p. 145-51.
Yoon KW, et al. "Control of signaling-mediated clearance of apoptotic cells by the tumor suppressor p53," Science. 2015;349(6247):1261669.
Yoshinaga SK, et al. "T-cell co-stimulation through B7RP-1 and ICOS," Nature. Dec. 16, 1999;402(6763):827-32.
Youle RJ, et al. "Anti-Thy 1.2 monoclonal antibody linked to ricin is a potent cell-type-specific toxin," Proc Natl Acad Sci U S A. Sep. 1980;77(9):5483-6.
Youngnak, P., "Differential binding properties of B7-H1 and B7-DC to programmed death-1," Biochem Biophys Res Commun 2003. 307: 672-677.
Zenewicz, et al. "CD4 T-cell differentiation and inflammatory bowel disease," Trends Mol Med. May 2009;15(5):199-207.
Zervos AS, et al. "Mxi1, a protein that specifically interacts with Max to bind Myc-Max recognition sites," Cell. Jan. 29, 1993;72(2):223-32.
Zhang X, et al. "Bcr-Abl efficiently induces a myeloproliferative disease and production of excess interleukin-3 and granulocyte-macrophage colony-stimulating factor in mice: a novel model for chronic myelogenous leukemia," Blood. Nov. 15, 1998;92(10):3829-40.
Zhang, A., (2015), "Conformational difference in human IgG2 disulfide isoforms revealed by hydrogen/deuterium exchange mass spectrometry", Biochemistry, 54(10), 1956-1962.
Zheng, S. G., et al., "TGF-beta requires CTLA-4 early after T cell activation to induce FoxP3 and generate adaptive CD4+CD25+ regulatory cells," J Immunol, 2006. 176(6): p. 3321-9.
Zhu N, et al. "Systemic gene expression after intravenous DNA delivery into adult mice," Science. Jul. 9, 1993;261(5118):209-11.
Zhu Y, et al. "B7-H5 costimulates human T cells via CD28H," Nat Commun. 2013;4:2043.
Zhu Z, et al. "High level secretion of a humanized bispecific diabody from *Escherichia coli*," Biotechnology (N Y). Feb. 1996;14(2):192-6.

(56) References Cited

OTHER PUBLICATIONS

Zhu, G., "B7-H4-deficient mice display augmented neutrophil-mediated innate immunity," Blood 2009. 113: 1759-1767.
Zon G. "Oligonucleotide analogues as potential chemotherapeutic agents," Pharm Res. Sep. 1988;5(9):539-49.
Zou, W, et al. "Inhibitory B7-family molecules in the tumour microenvironment," Nat Rev Immunol, 2008. 8(6): p. 467-77.
Zou, W., "Regulatory T cells, tumour immunity and immunotherapy," Nat Rev Immunol, 2006. 6(4): p. 295-307.
Zuckermann RN, et al. "Discovery of nanomolar ligands for 7-transmembrane G-protein-coupled receptors from a diverse N-(substituted)glycine peptoid library," J Med Chem. Aug. 19, 1994;37(17):2678-85.
Kiss I, et al. "Structure of the gene for cartilage matrix protein, a modular protein of the extracellular matrix. Exon/intron organization, unusual splice sites, and relation to alpha chains of beta 2 integrins, von Willebrand factor, complement factors B and C2, and epidermal growth factor," J Biol Chem. May 15, 1989;264(14):8126-34.
Kohl S, et al. "Human antibody-dependent cellular cytotoxicity and natural killer cytotoxicity to herpes simplex virus-infected autologous and allogeneic cells," Immunology. Jan. 1983;48(1):187-93.
Köhler G, et al. "Continuous cultures of fused cells secreting antibody of predefined specificity," Nature. Aug. 7, 1975;256(5517):495-7.
Kolaskar AS, et al. "A semi-empirical method for prediction of antigenic determinants on protein antigens," FEBS Lett. Dec. 10, 1990;276(1-2):172-4.
Kostelny SA, et al. "Formation of a bispecific antibody by the use of leucine zippers," J Immunol. Mar. 1, 1992;148(5):1547-53.
Kozbor D, et al. "Specific immunoglobulin production and enhanced tumorigenicity following ascites growth of human hybridomas," J Immunol Methods. Jul. 16, 1985;81(1):31-42.
Kozbor D, et al. "The production of monoclonal antibodies from human lymphocytes," Immunol Today. Mar. 1983;4(3):72-9.
Krishnamurthy S, et al. "Molecular and biologic markers of pre-malignant lesions of human breast," Adv Anat Pathol. May 2002;9(3):185-97.
Krolick KA, et al. "Selective killing of normal or neoplastic B cells by antibodies coupled to the A chain of ricin," Proc Natl Acad Sci U S A. Sep. 1980;77(9):5419-23.
Kroll DJ, et al. "A multifunctional prokaryotic protein expression system: overproduction, affinity purification, and selective detection," DNA Cell Biol. Jun. 1993;12(5):441-53.
Krutzik, S. R., et al., "TLR activation triggers the rapid differentiation of monocytes into macrophages and dendritic cells," Nat Med, 2005. 11(6): p. 653-60.
Kryczek, I., et al., "B7-H4 expression identifies a novel suppressive macrophage population in human ovarian carcinoma," J Exp Med, 2006. 203(4): p. 871-81.
Kryczek, I., et al., "Cutting edge: induction of B7-H4 on APCs through IL-10: novel suppressive mode for regulatory T cells," J Immunol, 2006. 177(1): p. 40-4.
Kurjan J, et al. "Structure of a yeast pheromone gene (MF alpha): a putative alpha-factor precursor contains four tandem copies of mature alpha-factor," Cell. Oct. 1982;30(3):933-43.
Kuroiwa Y, et al. "Cloned transchromosomic calves producing human immunoglobulin," Nat Biotechnol. Sep. 2002;20(9):889-94.
Kwoh DY, et al. "Transcription-based amplification system and detection of amplified human immunodeficiency virus type 1 with a bead-based sandwich hybridization format," Proc Natl Acad Sci U S A. Feb. 1989;86(4):1173-7.
Labrijn AF, et al. "Efficient generation of stable bispecific IgG1 by controlled Fab-arm exchange," Proc Natl Acad Sci U S A. Mar. 26, 2013;110(13):5145-50.
Lakso M, et al. "Targeted oncogene activation by site-specific recombination in transgenic mice," Proc Natl Acad Sci U S A. Jul. 15, 1992;89(14):6232-6.

Lam KS, et al. "A new type of synthetic peptide library for identifying ligand-binding activity," Nature. Nov. 7, 1991;354(6348):82-4.
Lam KS. "Application of combinatorial library methods in cancer research and drug discovery," Anticancer Drug Des. Apr. 1997;12(3):145-67. Abstract Only.
Landegren U, et al. "A ligase-mediated gene detection technique," Science. Aug. 26, 1988;241(4869):1077-80.
Landt O, et al. "A general method for rapid site-directed mutagenesis using the polymerase chain reaction," Gene. Nov. 30, 1990;96(1):125-8.
Latchman Y, et al. "PD-L2 is a second ligand for PD-1 and inhibits T cell activation," Nat Immunol. Mar. 2001;2(3):261-8.
Latchman YE, et al. "PD-L1-deficient mice show that PD-L1 on T cells, antigen-presenting cells, and host tissues negatively regulates T cells," Proc Natl Acad Sci U S A. Jul. 20, 2004;101(29):10691-6.
Lathe R. "Synthetic oligonucleotide probes deduced from amino acid sequence data. Theoretical and practical considerations," J Mol Biol. May 5, 1985;183(1):1-12.
Lázár-Molnár E, et al. "Crystal structure of the complex between programmed death-1 (PD-1) and its ligand PD-L2," Proc Natl Acad Sci U S A. Jul. 29, 2008;105(30):10483-8.
Le Borgne, M., et al., "Dendritic cells rapidly recruited into epithelial tissues via CCR6/CCL20 are responsible for CD8+ T cell crosspriming in vivo," Immunity, 2006. 24(2): p. 191-201.
Le Mercier I, et al. "VISTA Regulates the Development of Protective Antitumor Immunity," Cancer Res. Apr. 1, 2014;74(7):1933-44.
Lemaitre M, et al. "Specific antiviral activity of a poly(L-lysine)-conjugated oligodeoxyribonucleotide sequence complementary to vesicular stomatitis virus N protein mRNA initiation site," Proc Natl Acad Sci U S A. Feb. 1987;84(3):648-52.
Leng et al., "Potential roles of IL-9 in the pathogenesis of systemic lupus erythematosus", American Journal of Clinical and Experimental Immunology 2012;I(I):28-32.
León B, et al. "Monocyte-derived dendritic cells formed at the infection site control the induction of protective T helper 1 responses against Leishmania," Immunity. Apr. 2007;26(4):519-31.
León B, et al. "Monocyte-derived dendritic cells in innate and adaptive immunity," Immunol Cell Biol. May-Jun. 2008;86(4):320-4.
Letsinger RL, et al. "Cholesteryl-conjugated oligonucleotides: synthesis, properties, and activity as inhibitors of replication of human immunodeficiency virus in cell culture," Proc Natl Acad Sci U S A. Sep. 1989;86(17):6553-6.
Li F, et al. "Inhibitory Fcγ receptor is required for the maintenance of tolerance through distinct mechanisms," J Immunol. Apr. 1, 2014;192(7):3021-8.
Lin DY, et al. "The PD-1/PD-L1 complex resembles the antigen-binding Fv domains of antibodies and T cell receptors," Proc Natl Acad Sci U S A. Feb. 26, 2008;105(8):3011-6.
Lines JL, et al. "VISTA is a novel broad-spectrum negative checkpoint regulator for cancer immunotherapy," Cancer Immunol Res. Jun. 2014;2(6):510-7.
Lines JL, et al. "VISTA is an immune checkpoint molecule for human T cells," Cancer Res. Apr. 1, 2014;74(7):1924-32.
Liu AY, et al. "Chimeric mouse-human IgG1 antibody that can mediate lysis of cancer cells," Proc Natl Acad Sci U S A. May 1987;84(10):3439-43.
Liu J, et al. "Immune-checkpoint proteins VISTA and PD-1 nonredundantly regulate murine T-cell responses," Proc Natl Acad Sci U S A. May 26, 2015;112(21):6682-7.
Liu MA, et al. "Heteroantibody duplexes target cells for lysis by cytotoxic T lymphocytes," Proc Natl Acad Sci U S A. Dec. 1985;82(24):8648-52.
Lobley A, et al. "pGenTHREADER and pDomTHREADER: new methods for improved protein fold recognition and superfamily discrimination," Bioinformatics. Jul. 15, 2009;25(14):1761-7.
Lonberg N, et al. "Antigen-specific human antibodies from mice comprising four distinct genetic modifications," Nature. Apr. 28, 1994;368(6474):856-9.
Lonberg N, et al. "Human antibodies from transgenic mice," Int Rev Immunol. 1995;13(1):65-93.

(56) References Cited

OTHER PUBLICATIONS

Lopez-Pedrera et al., "Accelerated atherosclerosis in systemic lupus erythematosus: role of proinflammatory cytokines and therapeutic approaches", Journal of Biomedicine & Biotechnology, 2010 Article ID 607084.
Lorain S, et al. "Transient immunomodulation allows repeated injections of AAV1 and correction of muscular dystrophy in multiple muscles," Mol Ther. Mar. 2008;16(3):541-7.
Luckow VA, et al. "High level expression of nonfused foreign genes with Autographa californica nuclear polyhedrosis virus expression vectors," Virology. May 1989;170(1):31-9.
Lutz MB, et al. "An advanced culture method for generating large quantities of highly pure dendritic cells from mouse bone marrow," J Immunol Methods. Feb. 1, 1999;223(1):77-92.
Maher LJ. "Dna triple-helix formation: an approach to artificial gene repressors?" Bioessays. Dec. 1992;14(12):807-15.
Mahnke K, et al. "The dendritic cell receptor for endocytosis, DEC-205, can recycle and enhance antigen presentation via major histocompatibility complex class II-positive lysosomal compartments," J Cell Biol. Oct. 30, 2000;151(3):673-84.
Malashkevich VN, et al. "The crystal structure of a five-stranded coiled coil in COMP: a prototype ion channel?" Science. Nov. 1, 1996;274(5288):761-5.
Marigo, I., et al. "Tumor-induced tolerance and immune suppression by myeloid derived suppressor cells," Immunol Rev, 2008. 222: p. 162-79.
Martinez T, et al. "Disulfide connectivity of human immunoglobulin G2 structural isoforms," Biochemistry. Jul. 15, 2008;47(28):7496-508.
McCafferty J, et al. "Phage antibodies: filamentous phage displaying antibody variable domains," Nature. Dec. 6, 1990;348(6301):552-4.
McConnell HM, et al. "The cytosensor microphysiometer: biological applications of silicon technology," Science. Sep. 25, 1992;257(5078):1906-12.
McHugh RS, et al. "CD4(+)CD25(+) immunoregulatory T cells: gene expression analysis Yeveals a functional role for the glucocorticoid-induced TNF receptor," Immunity. Feb. 2002;16(2):311-23.
McIvor RS, et al. "Isolation and characterization of a variant dihydrofolate reductase cDNA from methotrexate-resistant murine L5178Y cells," Nucleic Acids Res. Dec. 11, 1990;18(23):7025-32.
Medina D. "The preneoplastic phenotype in murine mammary tumorigenesis," J Mammary Gland Biol Neoplasia. Oct. 2000;5(4):393-407.
Morrison SL, et al. "Chimeric human antibody molecules: mouse antigen-binding domains with human constant region domains," Proc Natl Acad Sci U S A. Nov. 1984;81(21):6851-5.
Morrison SL. "Transfectomas provide novel chimeric antibodies," Science. Sep. 20, 1985;229(4719):1202-7.
Neuberger MS, et al. "Recombinant antibodies possessing novel effector functions," Nature. Dec. 13-19, 1984;312(5995):604-8.
Nishimura H, et al. "Autoimmune dilated cardiomyopathy in PD-1 receptor-deficient mice," Science. Jan. 12, 2001;291(5502):319-22.
Nishimura H, et al. "Development of lupus-like autoimmune diseases by disruption of the PD-1 gene encoding an ITIM motif-carrying immunoreceptor," Immunity. Aug. 1999;11(2):141-51.
O'Gorman S, et al. "Recombinase-mediated gene activation and site-specific integration in mammalian cells," Science. Mar. 15, 1991;251(4999):1351-5.
Orlandi R, et al. "Cloning immunoglobulin variable domains for expression by the polymerase chain reaction," Proc Natl Acad Sci U S A. May 1989;86(10):3833-7.
Ostergaard S, et al. "Peptomers: a versatile approach for the preparation of diverse combinatorial peptidomimetic bead libraries," Mol Divers. 1997;3(1):17-27.
Ostresh JM, et al. "Generation and use of nonsupport-bound peptide and peptidomimetic combinatorial libraries," Methods Enzymol. 1996;267:220-34.
Owais M, et al. "Chloroquine encapsulated in malaria-infected erythrocyte-specific antibody-bearing liposomes effectively controls chloroquine-resistant Plasmodium berghei infections in mice," Antimicrob Agents Chemother. Jan. 1995;39(1):180-4.
Oyarzun P, et al. "A bioinformatics tool for epitope-based vaccine design that accounts for human ethnic diversity: Application to emerging infectious diseases," Vaccine. 2015;33(10):1267-73.
Ozkaynak, E., et al. "Programmed death-1 targeting can promote al lograft survival," J Immunol 2002. 169: 6546-6553.
Pain D, et al. "Preparation of protein A-peroxidase monoconjugate using a heterobifunctional reagent, and its use in enzyme immunoassays," J Immunol Methods. 1981;40(2):219-30.
Parisi, S., et al. "A regulatory loop involving Dies1 and miR-125a controls BMP4 signaling in mouse embryonic stem cells," FASEB J 2012. 26: 3957-3968.
Paulsson M, et al. "Purification and structural characterization of a cartilage matrix protein," Biochem J. Aug. 1, 1981;197(2):367-75.
Payne G. "Progress in immunoconjugate cancer therapeutics," Cancer Cell. Mar. 2003;3(3):207-12.
Perry-O'Keefe H, et al. "Peptide nucleic acid pre-gel hybridization: an alternative to southern hybridization," Proc Natl Acad Sci U S A. Dec. 10, 1996;93(25):14670-5.
Pinkert CA, et al. "An albumin enhancer located 10 kb upstream functions along with its promoter to direct efficient, liver-specific expression in transgenic mice," Genes Dev. May 1987;1(3):268-76.
Powell MF, et al. "Peptide stability in drug development. II. Effect of single amino acid substitution and glycosylation on peptide reactivity in human serum," Pharm Res. Sep. 1993;10(9):1268-73.
Prasad, D. V., et al., B7S1, a novel B7 family member that negatively regulates T cell activation. Immunity, 2003. 18(6): p. 863-73.
Prokunina, L., A regulatory polymorphism in PDCD1 is associated with susceptibility to systemic lupus erythematosus in humans. Nat Genet 2002. 32: 666-669.
Qu, C., et al., Role of CCR8 and other chemokine pathways in the migration of monocyte-derived dendritic cells to lymph nodes. J Exp Med, 2004. 200(10): p. 1231-41.
Queen C, et al. "Immunoglobulin gene transcription is activated by downstream sequence elements," Cell. Jul. 1983;33(3):741-8.
Queen C, et al. "A humanized antibody that binds to the interleukin 2 receptor," Proc Natl Acad Sci USA. Dec. 1989;86(24):10029-33.
Rabinovich, G. A., D. Gabrilovich, and E. M. Sotomayor, Immunosuppressive strategies that are mediated by tumor cells. Annu Rev Immunol, 2007. 25: p. 267-96.
Rai BK, et al. "MMM: a sequence-to-structure alignment protocol," Bioinformatics. Nov. 1, 2006;22(21):2691-2.
Rain JC, et al. "The protein-protein interaction map of Helicobacter pylori," Nature. Jan. 11, 2001;409(6817):211-5.
Ranade VV. "Drug delivery systems. 1. site-specific drug delivery using liposomes as carriers," J Clin Pharmacol. Aug. 1989;29(8):685-94.
Randolph, G. J., et al., Differentiation of phagocytic monocytes into lymph node dendritic cells in vivo Immunity, 1999. 11(6): p. 753-61.
Rattan SI, et al. "Protein synthesis, posttranslational modifications, and aging," Ann N Y Acad Sci. Nov. 21, 1992;663:48-62.
Ravetch JV, et al. "IgG Fc receptors," Annu Rev Immunol. 2001;19:275-90.
Rizo J, et al. "Constrained peptides: models of bioactive peptides and protein substructures," Annu Rev Biochem. 1992;61:387-418.
Robben, P. M., et al., Recruitment of Gr-1+ monocytes is essential for control of acute toxoplasmosis. J Exp Med, 2005. 201(11): p. 1761-9.
Roberge JY, et al. "A strategy for a convergent synthesis of N-linked glycopeptides on a solid support," Science. Jul. 14, 1995;269(5221):202-4.
Robertson JM, Jensen PE, Evavold BD. DO11.10 and OT-II T Cells Recognize a C-Terminal Ovalbumin 323-339 Epitope. The Journal of Immunology. 2000;164(9):4706-12. doi 10.4049/jimmunol.164. 9.4706.
Roda G, Jharap B, Neeraj N, Colombel J-F. Loss of Response to Anti-TNFs: Definition, Epidemiology, and Ma nagement. Clin Trans Gastroenterol. 2016;7:e135. doi: 10.1038/ctg.2015.63.

(56) References Cited

OTHER PUBLICATIONS

Rose TM, et al. "Consensus-degenerate hybrid oligonucleotide primers for amplification of distantly related sequences," Nucleic Acids Res. Apr. 1, 1998;26(7):1628-35.
Rossolini GM, et al. "Use of deoxyinosine-containing primers vs degenerate primers for polymerase chain reaction based on ambiguous sequence information," Mol Cell Probes. Apr. 1994;8(2):91-8.
Saito G, et al. "Drug delivery strategy utilizing conjugation via reversible disulfide linkages: role and site of cellular reducing activities," Adv Drug Deliv Rev. Feb. 10, 2003;55(2):199-215.
Sakaguchi S, et al. "Immunologic self-tolerance maintained by activated T cells expressing IL-2 receptor alpha-chains (CD25). Breakdown of a single mechanism of self-tolerance causes various autoimmune diseases," J Immunol. Aug. 1, 1995 l;155(3):1151-64.
Sakaguchi S, et al. "Organ-specific autoimmune diseases induced in mice by elimination of T cell subset. 1. Evidence for the active participation of T cells in natural self-tolerance; deficit of a T cell subset as a possible cause of autoimmune disease," J Exp Med. Jan. 1, 1985;161(1):72-87.
Sakaguchi S, et al. "Regulatory T cells: key controllers of immunologic self-tolerance," Cell. May 26, 2000;101(5):455-8.
Salama AD, et al. "Critical role of the programmed death-1 (PD-1) pathway in regulation of experimental autoimmune encephalomyelitis," J Exp Med. Jul. 7, 2003;198(1):71-8.
Scaria A, et al. "Antibody to CD40 ligand inhibits both humoral and cellular immune Yesponses to adenoviral vectors and facilitates repeated administration to mouse airway," Gene Ther. Jun. 1997;4(6):611-7.
Scarlett, U. K., et al., In situ stimulation of CD40 and Toll-like receptor 3 transforms ovarian cancerinfiltrating dendritic cells from immunosuppressive to immunostimulatory cells. Cancer Res, 2009. 69(18): p. 7329-37.
Schreier H, et al. "Targeting of liposomes to cells expressing CD4 using glycosylphosphatidylinositol-anchored gp120. Influence of liposome composition on intracellular trafficking," J Biol Chem. Mar. 25, 1994;269(12):9090-8.
Schubbert R, et al. "Foreign (M13) DNA ingested by mice reaches peripheral leukocytes, spleen, and liver via the intestinal wall mucosa and can be covalently linked to mouse DNA," Proc Natl Acad Sci U S A. Feb. 4, 1997;94(3):961-6.
Schultz LD, et al. "Expression and secretion in yeast of a 400-kDa envelope glycoprotein derived from Epstein-Barr virus," Gene. 1987;54(1):113-23.
Scott JK, et al. "Searching for peptide ligands with an epitope library," Science. Jul. 27, 1990;249(4967):386-90.
Sedy, J. R., B and T lymphocyte attenuator regulates T cell activation through interaction with herpesvirus entry mediator. Nat Immunol 2005. 6: 90-98.
Seed B. "An LFA-3 cDNA encodes a phospholipid-linked membrane protein homologous to its receptor CD2," Nature. Oct. 29-Nov. 4;329(6142):840-2.
Seifter S, et al. "Analysis for protein modifications and nonprotein cofactors," Methods Enzymol. 1990;182:626-46.
Senter PD, et al. "Selective activation of anticancer prodrugs by monoclonal antibody-enzyme conjugates," Adv Drug Deliv Rev. Dec. 31, 2001;53(3):247-64.
Serbina, N. V., et al., TNF/iNOS-producing dendritic cells mediate innate immune defense against bacterial infection. Immunity, 2003. 19(1): p. 59-70.
Seregin SS, et al. "Improving adenovirus based gene transfer: strategies to accomplish immune evasion," Viruses. Sep. 2010;2(9):2013-36.
Sharma, M. D., et al., "Plasmacytoid dendritic cells from mouse tumor-draining lymph nodes directly activate mature Tregs via indoleamine 2,3-dioxygenase," J Clin Invest, 2007. 117(9) p. 2570-82.
Shaw DR, et al. "Mouse/human chimeric antibodies to a tumor-associated antigen: biologic activity of the four human IgG subclasses," J Natl Cancer Inst. Dec. 7, 1988;80(19):1553-9.
Fallarino F, et al. "B7-1 engagement of cytotoxic T lymphocyte antigen 4 inhibits T cell activation in the absence of CD28," J Exp Med. Jul. 6, 1998;188(1):205-10.
Fan YS, et al. "Mapping small DNA sequences by fluorescence in situ hybridization directly on banded metaphase chromosomes," Proc Natl Acad Sci U S A. Aug. 1990;87(16):6223-7.
Felici F, et al. "Selection of antibody ligands from a large library of oligopeptides expressed on a multivalent exposition vector," J Mol Biol. Nov. 20, 1991;222(2):301-10.
Finn PJ, et al. "Synthesis and properties of DNA-PNA chimeric oligomers," Nucleic Acids Res. Sep. 1, 1996;24(17):3357-63.
Fishwild DM, et al. "High-avidity human IgG kappa monoclonal antibodies from a novel strain of minilocus transgenic mice," Nat Biotechnol. Jul. 1996;14(7):845-51.
Flies DB, et al. "Coinhibitory receptor PD-1H preferentially suppresses CD4$^+$ T cell-mediated immunity," J Clin Invest. May 2014;124(5):1966-75.
Flies DB, et al. "Mechanistic Assessment of PD-1H Coinhibitory Receptor-Induced T Cell Tolerance to Allogeneic Antigens," J Immunol. Jun. 1, 2015;194(11):5294-304.
Fodor SP, et al. "Multiplexed biochemical assays with biological chips," Nature. Aug. 5, 1993;364(6437):555-6.
Fontenot JD, et al. "Regulatory T cell lineage specification by the forkhead transcription factor foxp3," Immunity. Mar. 2005;22(3):329-41.
Formstecher E, et al. "Protein interaction mapping: a *Drosophila* case study," Genome Res. Mar. 2005;15(3):376-84.
Franklin, et al. "Immunologic differences between the 19 S and 7 S components of normal human gamma-globulin," J Immunol. Jan. 1957;78(1):11-8.
Freeman GJ, et al. "Engagement of the PD-1 immunoinhibitory receptor by a novel B7 family member leads to negative regulation of lymphocyte activation," J Exp Med. Oct. 2, 2000;192(7):1027-34.
Freeman GJ, et al. "Uncovering of functional alternative CTLA-4 counter-receptor in B7-deficient mice," Science. Nov. 5, 1993;262(5135):907-9.
Freeman GJ. "Structures of PD-1 with its ligands: sideways and dancing cheek to cheek," Proc Natl Acad Sci U S A. Jul. 29, 2008;105(30):10275-6.
Freier SM, et al. "Improved free-energy parameters for predictions of RNA duplex stability," Proc Natl Acad Sci U S A. Dec. 1986;83(24):9373-7.
Frenkel K, et al. "7,12-dimethylbenz[a]anthracene induces oxidative DNA modification in vivo," Free Radic Biol Med. Sep. 1995;19(3):373-80.
Fromont-Racine M, et al. "Toward a functional analysis of the yeast genome through exhaustive two-hybrid screens," Nat Genet. Jul. 1997;16(3):277-82.
Futaki S. "Arginine-rich peptides: potential for intracellular delivery of macromolecules and the mystery of the translocation mechanisms," Int J Pharm. Oct. 1, 2002;245(1-2):1-7.
Gabrilovich D. "Mechanisms and functional significance of tumour-induced dendritic-cell defects," Nat Rev Immunol. Dec. 2004;4(12):941-52.
Gabrilovich DI, et al. "Myeloid-derived suppressor cells as regulators of the immune system," Nat Rev Immunol. Mar. 2009;9(3):162-74.
Galfre, G. et al. "Antibodies to major histocompatibility anitigens produced by hybrid cell Tines," Nature, vol. 266, Apr. 1977, 550-52.
Gallop MA, et al. "Applications of combinatorial technologies to drug discovery. 1. Background and peptide combinatorial libraries," J Med Chem. Apr. 29, 1994;37(9):1233-51.
Gao, Q., et al., "Overexpression of PD-LI significantly associates with tumor aggressiveness and postoperative recurrence in human hepatocellular carcinoma," Clin Cancer Res, 2009. 15(3): p. 971-9.
Gautier C, et al. "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids Res. Aug. 25, 1987;15(16):6625-41.
Gavin MA, et al. "Homeostasis and anergy of CD4(+)CD25(+) suppressor T cells in vivo," Nat Immunol. Jan. 2002;3(1):33-41.

(56) References Cited

OTHER PUBLICATIONS

Gefter ML, et al. "A simple method for polyethylene glycol-promoted hybridization of mouse myeloma cells," Somatic Cell Genet. Mar. 1977;3(2):231-6.
Geissmann, F., et al. "Blood monocytes consist of two principal subsets with distinct migratory properties," Immunity, 2003. 19(1): p. 71-82.
Geissmann, F., et al., "Blood monocytes: distinct subsets, how they relate to dendritic cells, and their possible roles in the regulation of T-cell responses," Immunol Cell Biol, 2008. 86(5): p. 398-408.
Geissmann, F., et al., "Development of monocytes, macrophages, and dendritic cells," Science, 2010. 327(5966): p. 656-61.
Geng H, et al. "HSP70 vaccine in combination with gene therapy with plasmid DNA encoding sPD-1 overcomes immune resistance and suppresses the progression of pulmonary metastatic melanoma," Int J Cancer. Jun. 1, 2006;118(11):2657-64.
Ghiringhelli, F., et al., Tumor cells convert immature myeloid dendritic cells into TGF-beta-secreting cells inducing CD4+CD25+ regulatory T cell proliferation. J Exp Med, 2005. 202(7): p. 919-29.
Gilliland DG, et al. "Antibody-directed cytotoxic agents: use of monoclonal antibody to direct the action of toxin A chains to colorectal carcinoma cells," Proc Natl Acad Sci U S A. Aug. 1980;77(8):4539-43.
Glennie MJ, et al. "Preparation and performance of bispecific F(ab' gamma)2 antibody containing thioether-linked Fab' gamma fragments," J Immunol. Oct. 1, 1987;139(7):2367-75.
Gluzman Y, et al. "SV40 early mutants that are defective for viral DNA synthesis but competent for transformation of cultured rat and simian cells," Virology. Nov. 1982;123(1):78-92.
Goeddel DV. "Systems for heterologous gene expression," Methods Enzymol. 1990;185:3-7.
Grabie N, et al. "Endothelial programmed death-1 ligand 1 (PD-L1) regulates CD8+ T-cell mediated injury in the heart," Circulation. Oct. 30, 2007;116(18):2062-71.
Graziano RF, et al. "Construction and characterization of a humanized anti-gamma-Ig Yeceptor type 1 (Fc gamma RI) monoclonal antibody," J Immunol. Nov. 15, 1995;155(10):4996-5002.
Greenwald RJ, et al. " The B7 family revisited," Annu Rev Immunol. 2005;23:515-48.
Groux H, et al. "A CD4+ T-cell subset inhibits antigen-specific T-cell responses and prevents colitis," Nature. Oct. 16, 1997;389(6652):737-42.
Gruber M, et al. "Efficient tumor cell lysis mediated by a bispecific single chain antibody expressed in *Escherichia coli*," J Immunol. Jun. 1, 1994;152(11):5368-74.
Guatelli JC, et al. "Isothermal, in vitro amplification of nucleic acids by a multienzyme reaction modeled after retroviral replication," Proc Natl Acad Sci U S A. Mar. 1990;87(5):1874-8.
Guindon S, et al. "A simple, fast, and accurate algorithm to estimate large phylogenies by maximum likelihood," Syst Biol. Oct. 2003;52(5):696-704.
Guleria I, et al. "A critical role for the programmed death ligand 1 in fetomaternal tolerance," J Exp Med. Jul. 18, 2005;202(2):231-7.
Gurley WB, et al. "Upstream sequences required for efficient expression of a soybean heat shock gene," Mol Cell Biol. Feb. 1986;6(2):559-65.
Hamilton AJ, et al. "A species of small antisense RNA in post-transcriptional gene silencing in plants," Science. Oct. 29, 1999;286(5441):950-2.
Hann M "On the Double Bond Isostere of the Peptide Bond: Preparation of an Enkephalin Analogue," Journal of the Chemical Society, Perkin Transactions 1982 (1), 307-14.
Hara M, et al. "IL-10 is required for regulatory T cells to mediate tolerance to alloantigens in vivo," J Immunol. Mar. 15, 2001;166(6):3789-96.
Harding FA, et al. "Class switching in human immunoglobulin transgenic mice," nn N Y Acad Sci. Sep. 29, 1995;764:536-46.
Haseloff J, et al. "Simple RNA enzymes with new and highly specific endoribonuclease activities," Nature. Aug. 18, 1988;334(6183):585-91.

Hashida H, et al. "Fusion of HIV-1 Tat protein transduction domain to poly-lysine as a new DNA delivery tool," Br J Cancer. Mar. 22, 2004;90(6):1252-8.
Haskins K, et al. "The major histocompatibility complex-restricted antigen receptor on T cells. I. Isolation with a monoclonal antibody," The Journal of Experimental Medicine. 1983;157(4):1149-69.
Hauser N, et al. "Interaction of cartilage matrix protein with aggrecan. Increased covalent cross-linking with tissue maturation," J Biol Chem. Dec. 13, 1996;271(50):32247-52.
Haynes JR, et al. "Particle-mediated nucleic acid immunization," J Biotechnol. Jan. 26, 1996;44(1-3):37-42.
Hedbom E, et al. "Cartilage matrix proteins. An acidic oligomeric protein (COMP) detected only in cartilage," J Biol Chem. Mar. 25, 1992;267(9):6132-6.
Helene C, et al. "Control of gene expression by triple helix-forming oligonucleotides. The antigene strategy," Ann N Y Acad Sci. Oct. 28, 1992;660:27-36.
Hellstrom I, et al. "CD3-mediated activation of tumor-reactive lymphocytes from patients with advanced cancer," Proc Natl Acad Sci U S A. Jun. 5, 2001;98(12):6783-8.
Hinton PR, et al. "Engineered human IgG antibodies with longer serum half-lives in primates," J Biol Chern. Feb. 20, 2004;279(8):6213-6.
Hirano, F., et al., Blockade of B7-H1 and PD-1 by monoclonal antibodies potentiates cancer therapeutic immunity Cancer Res, 2005. 65(3): p. 1089-96.
Ho SN, et al. "Site-directed mutagenesis by overlap extension using the polymerase chain Yeaction," Gene. Apr. 15, 1989;77(1):51-9.
Ho VT, et al. "The history and future of T-cell depletion as graft-versus-host disease prophylaxis for allogeneic hematopoietic stem cell transplantation," Blood. Dec. 1, 2001;98(12):3192-204.
Hodi, F. S., Overcoming immunological tolerance to melanoma: Targeting CTLA-4. Asia Pac J Clin Oncol, 2010. 6 Suppl 1: p. S16-23.
Hogg N. "The structure and function of Fc receptors," Immunol Today. Jul.-Aug. 1988;9(7-8):185-7.
Holladay, M. W., et al. (1983). "Synthesis of hydroxyethylene and ketomethylene dipeptide isosteres," Tetrahedron Letters 1983 24(41), 4401-4404.
Hollenbaugh D, et al. "Cleavable CD40Ig fusion proteins and the binding to sgp39," J Immunol Methods. Dec. 15, 1995;188(1):1-7.
Holliger P, et al. ""Diabodies": small bivalent and bispecific antibody fragments," Proc Natl Acad Sci USA. Jul. 15, 1993;90(14):6444-8.
Holm L, et al. "DaliLite workbench for protein structure comparison," Bioinformatics. Jun. 2000;16(6):566-7.
Hoos, A., et al., "Development of ipilimumab: contribution to a new paradigm for cancer immunotherapy," Semin Oncol, 2010. 37(5): p. 533-46.
Hopp TP, et al. "Prediction of protein antigenic determinants from amino acid sequences," Proc Natl Acad Sci U S A. Jun. 1981;78(6):3824-8.
Horn JR, et al. "The role of protein dynamics in increasing binding affinity for an engineered protein-protein interaction established by H/D exchange mass spectrometry," Biochemistry. Jul. 18, 2006;45(28):8488-98.
Hotchkiss RS, et al. "Immunosuppression in sepsis: a novel understanding of the disorder and a new therapeutic approach," Lancet Infect Dis. Mar. 2013;13(3):260-8.
Houghten RA, et al. "The use of synthetic peptide combinatorial libraries for the identification of bioactive peptides," Bioorganic & Medicianl Chemistry Letters, vol. 3, No. 3, 1993. pp. 405-412.
Hruby VJ, et al. "Conformational and topographical considerations in the design of biologically active peptides," Biopolymers. Jul. 1993;33(7):1073-82.
Hruby VJ, et al. "Synthesis of oligopeptide and peptidomimetic libraries," Curr Opin Chern Biol. Jun. 1997;1(1):114-9.
Hruby VJ. "Conformational restrictions of biologically active peptides via amino acid side chain groups," Life Sci. Jul. 19, 1982;31(3):189-99.

(56) References Cited

OTHER PUBLICATIONS

Huarte, E., et al., "Depletion of dendritic cells delays ovarian cancer progression by boosting antitumor immunity," Cancer Res, 2008. 68(18): p. 7684-91.
Hudson D, et al. "Methionine enkephalin and isosteric analogues. 1. Synthesis on a phenolic Yesin support," Int J Pept Protein Res. 1979;14(3):177-85.
Huston JS, et al. "Protein engineering of antibody binding sites: recovery of specific activity in an anti-digoxin single-chain Fv analogue produced in *Escherichia coli*," Proc Natl Acad Sci USA. Aug. 1988;85(16):5879-83.
Hutloff A, et al. "ICOS is an inducible T-cell co-stimulator structurally and functionally Yelated to CD28," Nature. Jan. 21, 1999;397(6716):263-6.
Hyrup B, e al. "Peptide nucleic acids (PNA): synthesis, properties and potential applications," Bioorg Med Chem. Jan. 1996;4(1):5-23.
Ike Y, et al. "Solid phase synthesis of polynucleotides. VIII. Synthesis of mixed oligodeoxyribonucleotides by the phosphotriester solid phase method," Nucleic Acids Res. Jan. 25, 1983;11(2):477-88.
Inoue H, et al. "Sequence-dependent hydrolysis of RNA using modified oligonucleotide splints and RNase H," FEBS Lett. May 11, 1987;215(2):327-30.
Inoue H, et al. "Synthesis and hybridization studies on two complementary nona(2'-O-methyl)ribonucleotides," Nucleic Acids Res. Aug. 11, 1987;15(15):6131-48.
Invitrogen (2002) "Guide to Baculovirus Expression Vector Systems (BEVs) and Insect Culture Techniques" Instruction Manual.
Itakura K, et al. "Expression in *Escherichia coli* of a chemically synthesized gene for the hormone somatostatin," Science. Dec. 9, 1977;198(4321):1056-63.
Itakura K, et al. "Synthesis and use of synthetic oligonucleotides," Annu Rev Biochem. 1984;53:323-56.
Iwai, Y., et al., "Involvement of PD-L1 on tumor cells in the escape from host immune system and tumor immunotherapy by PD-L1 blockade," Proc Natl Acad Sci USA, 2002. 99(19): p. 12293-7.
Jarvinen LZ, et al. "CD154 on the surface of CD4+CD25+ regulatory T cells contributes to skin transplant tolerance," Transplantation. Nov. 15, 2003;76(9):1375-9.
Jennings-White, C. et al. (1982). "Synthesis of ketomethylene analogs of dipeptides," Tetrahedron Letters 1982 23(25), 2533-2534.
Jones E, et al. "Depletion of CD25+ regulatory cells results in suppression of melanoma growth and induction of autoreactivity in mice," Cancer Immun. Feb. 22, 2002;2:1.
Jones PT, et al. "Replacing the complementarity-determining regions in a human antibody with those from a mouse," Nature. May 29-Jun. 4, 1986;321(6069):522-5.
Kaehler, K. C., et al., "Update on immunologic therapy with anti-CTLA-4 antibodies in melanoma: identification of clinical and biological response patterns, immune-related adverse events, and their management," Semin Oncol, 2010. 37(5): p. 485-98.
Kang SM, et al. "Transactivation by AP-1 is a molecular target of T cell clonal anergy," Science. Aug. 21, 1992;257(5073):1134-8.
Karpovsky B, et al. "Production of target-specific effector cells using hetero-cross-linked aggregates containing anti-target cell and anti-Fc gamma receptor antibodies," J Exp Med. Dec. 1, 1984;160(6):1686-701.
Kashmiri SV, et al. "SDR grafting—a new approach to antibody humanization," Methods. May 2005;36(1):25-34.
Kaufman RJ, et al. "Translational efficiency of polycistronic mRNAs and their utilization to express heterologous genes in mammalian cells," EMBO J. Jan. 1987;6(1):187-93.
Kay MA, et al. "Transient immunomodulation with anti-CD40 ligand antibody and CTLA4Ig enhances persistence and secondary adenovirus-mediated gene transfer into mouse liver," Proc Natl Acad Sci U S A. Apr. 29, 1997;94(9):4686-91.
Keinänen K, et al. "Biosynthetic lipid-tagging of antibodies," FEBS Lett. Jun. 6, 1994;346(1):123-6.

Keir ME, et al. "PD-1 and its ligands in tolerance and immunity," Annu Rev Immunol. 2008;26:677-704.
Keir ME, et al. "PD-1 regulates self-reactive CD8+ T cell responses to antigen in lymph nodes and tissues," mmunol. Oct. 15, 2007;179(8):5064-70.
Kessel M, et al. "Murine developmental control genes," Science. Jul. 27, 1990;249(4967):374-9.
Killion JJ, et al. "Systemic targeting of liposome-encapsulated immunomodulators to macrophages for treatment of cancer metastasis," Immunomethods. Jun. 1994;4(3):273-9.
Kimmel AR, et al. "Preparation of cDNA and the generation of cDNA libraries: overview," Methods Enzymol. 1987;152:307-16.
Kipriyanov SM, et al. "Recombinant single-chain Fv fragments carrying C-terminal cysteine Yesidues: production of bivalent and biotinylated miniantibodies," Mol Immunol. Oct. 1994;31(14):1047-58.
Kipriyanov SM, et al. "Single-chain antibody streptavidin fusions: tetrameric bifunctional scFv-complexes with biotin binding activity and enhanced affinity to antigen," Hum Antibodies Hybridomas. 1995;6(3):93-101.
Aalberse RC, et al. "IgG4 breaking the rules," Immunology. Jan. 2002;105(1):9-19.
Adriouch S, et al. "Improved Immunological Tolerance Following Combination Therapy with CTLA-4/Ig and AAV-Mediated PD-L1/2 Muscle Gene Transfer," Front Microbiol. Sep. 29, 2011;2:199.
Allen, et al., (2009), "Interchain disulfide bonding in human lgG2 antibodies probed by site-directed mutagenesis", Biochemistry, 48(17), 3755-3766.
Allen, T. M. "Ligand-targeted therapeutics in anticancer therapy," Nat Rev Cancer. Oct. 2002;2(10):750-63.
Almquist RG, et al. "Synthesis and biological activity of a ketomethylene analogue of a tripeptide inhibitor of angiotensin converting enzyme," J Med Chem. Dec. 1980;23(12):1392-8.
Al-Obeidi F, et al. "Peptide and peptidomimetic libraries. Molecular diversity and drug design," Mol Biotechnol. Jun. 1998;9(3):205-23.
Altman JD, et al. "Phenotypic analysis of antigen-specific T lymphocytes," Science. Oct. 4, 1996;274(5284):94-6.
Ansari MJ, et al. "The programmed death-1 (PD-1) pathway regulates autoimmune diabetes in nonobese diabetic (NOD) mice," J Exp Med. Jul. 7, 2003;198(1):63-9.
Arkin AP, et al. "An algorithm for protein engineering: simulations of recursive ensemble mutagenesis," Proc Natl Acad Sci U S A. Aug. 15, 1992;89(16):7811-5.
Attia, P., et al., Autoimmunity correlates with tumor regression in patients with metastatic melanoma treated with anti-cytotoxic T-lymphocyte antigen-4. J Clin Oncol, 2005. 23(25): p. 6043-53.
Auffray, C et al. "Blood monocytes: development, heterogeneity, and relationship with dendritic cells," Annu Rev Immunol, 2009. 27: p. 669-92.
Bak, S. P., et al., Murine ovarian cancer vascular leukocytes require arginase-1 activity for T cell suppression. Mol Immunol, 2008. 46(2): p. 258-68.
Baldari C, et al. "A novel leader peptide which allows efficient secretion of a fragment of human interleukin 1 beta in *Saccharomyces cerevisiae*," EMBO J. Jan. 1987;6(1):229-34.
Banerji J, et al. "A lymphocyte-specific cellular enhancer is located downstream of the joining region in immunoglobulin heavy chain genes," Cell. Jul. 1983;33(3):729-40.
Barringer KJ, et al. "Blunt-end and single-strand ligations by *Escherichia coli* ligase: influence on an in vitro amplification scheme," Gene. Apr. 30, 1990;89(1):117-22.
Bartel DP, et al. "Isolation of new ribozymes from a large pool of random sequences," Science. Sep. 10, 1993;261(5127):1411-8.
Baskar S, et al. "Constitutive expression of B7 restores immunogenicity of tumor cells expressing truncated major histocompatibility complex class II molecules," Proc Natl Acad Sci U S A. Jun. 18, 1993;90(12):5687-90.
Batzer MA, et al. "Enhanced evolutionary PCR using oligonucleotides with inosine at the 3'-terminus," Nucleic Acids Res. Sep. 25, 1991;19(18):5081.
Bauer S, et al. "Immunotherapy of human tumors with T-cell-activating bispecific antibodies: stimulation of cytotoxic pathways in vivo," Cancer Res. Apr. 15, 1999;59(8):1961-5.

(56) References Cited

OTHER PUBLICATIONS

Beidler CB, et al. "Cloning and high level expression of a chimeric antibody with specificity for human carcinoembryonic antigen," J Immunol. Dec. 1, 1988;141(11):4053-60.
Belousov ES, et al. "Sequence-specific targeting and covalent modification of human genomic DNA," Nucleic Acids Res. Sep. 1, 1997;25(17):3440-4.
Béranger F, et al. "Getting more from the two-hybrid system: N-terminal fusions to LexA are efficient and sensitive baits for two-hybrid studies," Nucleic Acids Res. May 15, 1997;25(10):2035-6.
Berge SM, et al. "Pharmaceutical salts," J Pharm Sci. Jan. 1977;66(1):1-19.
Berney C, et al. "A member of the dendritic cell family that enters B cell follicles and stimulates primary antibody responses identified by a mannose receptor fusion protein," J Exp Med. Sep. 20, 1999;190(6):851-60.
Better M, et al. "*Escherichia coli* secretion of an active chimeric antibody fragment," Science. May 20, 1988;240(4855):1041-3.
Bird RE, et al. "Single-chain antigen-binding proteins," Science. Oct. 21, 1988;242(4877):423-6.
Blank C, et al. "Interaction of PD-L1 on tumor cells with PD-1 on tumor-specific T cells as a mechanism of immune evasion: implications for tumor immunotherapy," Cancer Immunol Immunother. Apr. 2005;54(4):307-14.
Blank, C., et al., "PD-L1/B7H-1 inhibits the effector phase of tumor rejection by T cell Yeceptor (TCR) transgenic CD8+T cells," Cancer Res, 2004. 64(3): p. 1140-5.
Bloemen PG, et al. "Adhesion molecules: a new target for immunoliposome-mediated drug delivery," FEBS Lett. Jan. 3, 1995;357(2):140-4.
Blommers MJ, et al. "Effects of the introduction of L-nucleotides into DNA. Solution structure of the heterochiral duplex d(G-C-G-(L)T-G-C-G).d(C-G-C-A-C-G-C) studied by NMR spectroscopy," Biochemistry. Jun. 28, 1994;33(25):7886-96.
Bluestone JA, et al. "Natural versus adaptive regulatory T cells," Nat Rev Immunol. Mar. 2003;3(3):253-7.
Borriello F, et al. "B7-1 and B7-2 have overlapping, critical roles in immunoglobulin class switching and germinal center formation," Immunity. Mar. 1997;6(3):303-13.
Borrok MJ, "pH-dependent Binding Engineering Reveals an FcRn Affinity Threshold That Governs IgG Recycling," The Journal of Biological Chemistry. 2015;290(7):4282-90.
Boulianne GL, et al. "Production of functional chimaeric mouse/human antibody," Nature. Dec. 13-19, 1984;312(5995):643-6.
Brahmer, J. R., et al., Phase 1 study of single-agent anti-programmed death-1 (MDX-1106) in refractory solid tumors: safety, clinical activity, pharmacodynamics, and immunologic correlates. J Clin Oncol, 2010. 28(19): p. 3167-75.
Brandt C, et al. "The B7 family member B7-H6 is a tumor cell ligand for the activating natural killer cell receptor NKp30 in humans," J Exp Med. Jul. 6, 2009;206(7):1495-503.
Brennan M, et al. "Preparation of bispecific antibodies by chemical recombination of monoclonal immunoglobulin G1 fragments," Science. Jul. 5, 1985;229(4708):81-3.
Briscoe P, et al. "Delivery of superoxide dismutase to pulmonary epithelium via pH-sensitive liposomes," Am J Physiol. Mar. 1995;268(3 Pt 1):L374-80.
Brisson, et al. "Expression of a bacterial gene in plants by using a viral vector," Nature vol. 310 Aug. 1984, 511-14.
Broglie R, et al. "Light-regulated expression of a pea ribulose-1,5-bisphosphate carboxylase small subunit gene in transformed plant cells," Science. May 25, 1984;224(4651):838-43.
Brown JP, et al. "Protein antigens of normal and malignant human cells identified by immunoprecipitation with monoclonal antibodies," J Biol Chem. Jun. 10, 1980;255(11):4980-3.
Brown JP, et al. "Structural characterization of human melanoma-associated antigen p97 with monoclonal antibodies," J Immunol. Aug. 1981;127(2):539-46.

Burg JL, et al. "Single molecule detection of RNA reporter probes by amplification with Q beta replicase," Mol Cell Probes. Aug. 1996;10(4):257-71.
Butte MJ, et al. "Programmed death-1 ligand 1 interacts specifically with the B7-1 costimulatory molecule to inhibit T cell responses," Immunity. Jul. 2007;27(1):111-22.
Byrne GW, et al. "Multiplex gene regulation: a two-tiered approach to transgene regulation in transgenic mice," Proc Natl Acad Sci U S A. Jul. 1989;86(14):5473-7.
Cabilly S, et al. "Generation of antibody activity from immunoglobulin polypeptide chains produced in *Escherichia coli*," Proc Natl Acad Sci U S A. Jun. 1984;81(11):3273-7.
Cabilly S, et al. "Immunoglobulin transcripts and molecular history of a hybridoma that produces antibody to carcinoembryonic antigen," Gene. 1985;40(1):157-61.
Calabro, L., et al., "Clinical studies with anti-CTLA-4 antibodies in non-melanoma indications," Semin Oncol, 2010. 37(5): p. 460-7.
Calame K, et al. "Transcriptional controlling elements in the immunoglobulin and T cell Yeceptor loci," Adv Immunol. 1988;43:235-75.
Camper SA, et al. "Postnatal repression of the alpha-fetoprotein gene is enhancer independent," Genes Dev. Apr. 1989;3(4):537-46.
Carell, et al. "A Solution-Phase Screening Procedure for the Isolation of Active Compounds from a Library of Molecules," Angew. Chem. Int. Ed. Engl. 1994, 33. No. 20, 2061-64.
Carter L, et al. "PD-1:PD-L inhibitory pathway affects both CD4(+) and CD8(+) T cells and is overcome by IL-2," Eur J Immunol. Mar. 2002;32(3):634-43.
Ceeraz S, et al. "VISTA Deficiency Accelerates the Development of Fatal Murine Lupus Nephritis," Arthritis Rheumatol. Apr. 2017;69(4):814-825.
Chambers CA, et al. "Lymphoproliferation in CTLA-4-deficient mice is mediated by costimulation-dependent activation of CD4+T cells," Immunity. Dec. 1997;7(6):885-95.
Chan AC, et al. "Therapeutic antibodies for autoimmunity and inflammation," Nat Rev Immunol. May 2010;10(5):301-16.
Chen J, et al. "B cell development in mice that lack one or both immunoglobulin kappa light chain genes," EMBO J. Mar. 1993;12(3):821-30.
Chen J, et al. "Immunoglobulin gene rearrangement in B cell deficient mice generated by targeted deletion of the JH locus," Int Immunol. Jun. 1993;5(6):647-56.
Chen L, et al. "Costimulation of antitumor immunity by the B7 counterreceptor for the T Tymphocyte molecules CD28 and CTLA-4," Cell. Dec. 24, 1992;71(7):1093-102.
Chen SH, et al. "Gene therapy for brain tumors: regression of experimental gliomas by adenovirus-mediated gene transfer in vivo," Proc Natl Acad Sci U S A. Apr. 12, 1994;91(8):3054-7.
Chen, Y., Development of a sandwich ELISA for evaluating soluble PD-LI (CD274) in human sera of different ages as well as supernatants of PD-L1(+) cell lines. Cytokine 2011.
Cho CY, et al. "An unnatural biopolymer," Science. Sep. 3, 1993;261(5126):1303-5.
Choi TK, et al. "Transgenic mice containing a human heavy chain immunoglobulin gene fragment cloned in a yeast artificial chromosome," Nat Genet. Jun. 1993;4(2):117-23.
Chothia C, et al. "Canonical structures for the hypervariable regions of immunoglobulins," J Mol Biol. Aug. 20, 1987;196(4):901-17.
Church GM, et al. "Genomic sequencing," Proc Natl Acad Sci U S A. Apr. 1984;81(7):1991-5.
Clark KL, et al. "Association of the Arabidopsis CTR1 Raf-like kinase with the ETR1 and ERS ethylene receptors," Proc Natl Acad Sci U S A. Apr. 28, 1998;95(9):5401-6.
Cohen AA, et al. "Structure design: an artificial intelligence-based method for the design of molecules under geometrical constraints," J Mol Graph. Sep. 1993;11(3):166-73.
Cole SP, et al. "Human monoclonal antibodies," Mol Cell Biochem. Jun. 1984;62(2):109-20.
Conejo-Garcia, J. R., et al., "Tumor-infiltrating dendritic cell precursors recruited by a beta-defensin contribute to vasculogenesis under the influence of Vegf-A," Nat Med, 2004. 10(9): p. 950-8.

(56) References Cited

OTHER PUBLICATIONS

Copin, R., et al., "MyD88-dependent activation of B220-CD11b+ LY-6C+ dendritic cells during Brucella melitensis infection," J Immunol, 2007. 178(8): p. 5182-91.
Coruzzi G, et al. "Tissue-specific and light-regulated expression of a pea nuclear gene encoding the small subunit of ribulose-1,5-bisphosphate carboxylase," EMBO J. Aug. 1984;3(8):1671-9.
Corzo, C. A., et al., "HIF-1alpha regulates function and differentiation of myeloid-derived suppressor cells in the tumor microenvironment," J Exp Med, 2010. 207(11): p. 2439-53.
Cote RJ, et al. "Generation of human monoclonal antibodies reactive with cellular antigens," Proc Natl Acad Sci U S A. Apr. 1983;80(7):2026-30.
Cox JP, et al. "A directory of human germ-line V kappa segments reveals a strong bias in their usage," Eur J Immunol. Apr. 1994;24(4):827-36.
Cubillos-Ruiz, J. R., et al., "Polyethylenimine-based siRNA nanocomplexes reprogram tumor-associated dendritic cells via TLR5 to elicit therapeutic antitumor immunity," J Clin Invest, 2009. 119(8): p. 2231-44.
Cull MG, et al. "Screening for receptor ligands using large libraries of peptides linked to the C terminus of the lac repressor," Proc Natl Acad Sci U S A. Mar. 1, 1992;89(5):1865-9.
Cunningham BC, et al. "High-resolution epitope mapping of hGH-receptor interactions by alanine-scanning mutagenesis," Science. Jun. 2, 1989;244(4908):1081-5.
Curiel, T. J., et al., "Blockade of B7-H1 improves myeloid dendritic cell-mediated antitumor immunity," Nat Med, 2003. 9(5): p. 562-7.
Curiel, T. J., et al., "Specific recruitment of regulatory T cells in ovarian carcinoma fosters immune privilege and predicts reduced survival," Nat Med, 2004. 10(9): p. 942-9.
Cwirla SE, et al. "Peptides on phage: a vast library of peptides for identifying ligands," Proc Natl Acad Sci U S A. Aug. 1990;87(16):6378-82.
Dal Porto J, et al. "A soluble divalent class 1 major histocompatibility complex molecule inhibits alloreactive T cells at nanomolar concentrations," Proc Natl Acad Sci U S A. Jul. 15, 1993;90(14):6671-5.
David GS, et al. "Protein iodination with solid state lactoperoxidase," Biochemistry. Feb. 26, 1974;13(5):1014-21.
De Vos AM, et al. "Human growth hormone and extracellular domain of its receptor: crystal structure of the complex," Science. Jan. 17, 1992;255(5042):306-12.
Dean PM. "Recent advances in drug design methods: where will they lead?" Bioessays. Sep. 1994;16(9):683-7.
Delagrave S, et al. "Recursive ensemble mutagenesis," Protein Eng. Apr. 1993;6(3):327-31.
Dellinger et al. "International Guidelines for Management of Severe Sepsis and Septic Shock" K2013 Intensive Care Med 39: 165-228).
Deshayes S, et al. "Insight into the mechanism of internalization of the cell-penetrating carrier peptide Pep-1 through conformational analysis," Biochemistry. Feb. 17, 2004;43(6):1449-57.
D'Eustachio P, et al. "Somatic cell genetics and gene families," Science. May 27, 1983;220(4600):919-24.
Devlin JJ, et al. "Random peptide libraries: a source of specific protein binding molecules," Science. Jul. 27, 1990;249(4967):404-6.
DeWitt SH, et al. "'Diversomers': an approach to nonpeptide, nonoligomeric chemical diversity," Proc Natl Acad Sci U S A. Aug. 1, 1993;90(15):6909-13.
DiLillo DJ, et al. "Fc-Receptor Interactions Regulate Both Cytotoxic and Immunomodulatory Therapeutic Antibody Effector Functions," Cancer Immunology Research. 2015;3(7):704-13.
Dillon et al., Optimization of a reversed-phase high-performance liquid chromatography/mass spectrometry method.
Dong C, et al. "ICOS co-stimulatory receptor is essential for T-cell activation and function," Nature. Jan. 4, 2001;409(6816):97-101.
Dong H, et al. "B7-H1 pathway and its role in the evasion of tumor immunity," J Mol Med KBerl). May 2003;81(5):281-7.

Dong H, et al. "Tumor-associated B7-H1 promotes T-cell apoptosis: a potential mechanism of immune evasion," Nat Med. Aug. 2002;8(8):793-800.
Dubey AK, et al. "Belimumab: First targeted biological treatment for systemic lupus erythematosus," J Pharmacol Pharmacother. 2011;2(4):317-9.
Edlund T, et al. "Cell-specific expression of the rat insulin gene: evidence for role of two distinct 5' flanking elements," Science. Nov. 22, 1985;230(4728):912-6.
Ehst BD, et al. "Development of a novel transgenic mouse for the study of interactions between CD4 and CD8 T cells during graft rejection," American Journal of Transplantation: 2003;3(11):1355-62.
Elbashir SM, et al. "Duplexes of 21-nucleotide RNAs mediate RNA interference in cultured mammalian cells," Nature. May 24, 2001;411(6836):494-8.
Ellenberger TE, et al. "The GCN4 basic region leucine zipper binds DNA as a dimer of uninterrupted alpha helices: crystal structure of the protein-DNA complex," Cell. Dec. 24, 1992;71(7):1223-37.
Erb E, et al. "Recursive deconvolution of combinatorial chemical libraries," Proc Natl Acad Sci U S A. Nov. 22, 1994;91(24):11422-6.
Evans BE, et al. "Design of nonpeptidal ligands for a peptide receptor: cholecystokinin antagonists," J Med Chem. Jul. 1987;30(7):1229-39.
Gorczynski RM, et al. "Checkpoint blockade in solid tumors and B-cell malignancies, with special consideration of the role of CD200," Cancer Manag Res. Nov. 13, 2017;9:601-609.
Rice RH, et al. "Localization of hair shaft protein VSIG8 in the hair follicle, nail unit, and oral cavity," J Invest Dermatol. Sep. 2011;131(9):1936-8.
Blazar BR, Sharpe AH, Taylor PA, Panoskaltsis-Mortari A, Gray GS, Komgold R, Vallera DA. Infusion of anti-B7. 1 (CD80) and anti-B7. 2 (CD86) monoclonal antibodies inhibits murine graft-versus-host disease lethality in part via direct effects on CD4+ and CD8+ T cells. The Journal of Immunology. Oct. 15, 1996;157(8):3250-9.
Bogdan C. Nitric oxide and the immune response. Nature immunology. Oct. 2001;2(10):907.
Boon T, Coulie PG, Eynde BJ, Bruggen PV. Human T cell responses against melanoma. Annu. Rev. Immunol.. Apr. 23, 2006;24:175-208.
Di Maro et al., Planta 1999; 208: 125-131.
Duttagupta PA, Boesteanu AC, Katsikis PD. Costimulation signals for memory CD8+ T cells during viral infections. Critical Reviews™ in Immunology. 2009;29(6).
Flies DB, Han X, Higuchi T, Zheng L, Sun J, Ye JJ, Chen L. Coinhibitory receptor PD-1H preferentially suppresses CD4+ T cell-mediated immunity. The Journal of clinical investigation. May 1, 2014;124(5):1966-75.
Guindon S, Gascuel O. A simple, fast, and accurate algorithm to estimate large phylogenies by maximum likelihood. Systematic biology. Oct. 1, 2003;52(5):696-704.
Le Mercier I, Chen W, Lines JL, Day M, Li J, Sergent P, Noelle RJ, Wang L. VISTA regulates the development of protective antitumor immunity. Cancer research. Apr. 1, 2014;74(7):1933-44.
Lederman et al.: Molecular Immunology,1991, 28: 1171-1181.
Lee KH, Wang E, Nielsen MB, Wunderlich J, Migueles S, Connors M, Steinberg SM, Rosenberg SA, Marincola FM. Increased vaccine-specific T cell frequency after peptide-based vaccination correlates with increased susceptibility to in vitro stimulation but does not lead to tumor regression. The Journal of Immunology. Dec. 1, 1999;163(11):6292-300.
Lines et al., Cancer Immunology Research, 2(6):510-517 (Jun. 2014).
Lines JL, Pantazi E, Mak J, Sempere LF, Wang L, O'Connell S, Ceeraz S, Suriawinata AA, Yan S, Ernstoff MS, Noelle R. VISTA is an immune checkpoint molecule for human T cells. Cancer research. Apr. 1, 2014;74(7):1924-32.
Liu J, Yuan Y, Chen W, Putra J, Suriawinata AA, Schenk AD, Miller HE, Guleria I, Barth RJ, Huang YH, Wang L. Immune-checkpoint proteins VISTA and PD-1 nonredundantly regulate murine T-cell responses. Proceedings of the National Academy of Sciences. May 26, 2015;112(21):6682-7.

(56) References Cited

OTHER PUBLICATIONS

Lutz MB, Kukutsch N, Ogilvie AL, Rößner S, Koch F, Romani N, Schuler G. An advanced culture method for generating large quantities of highly pure dendritic cells from mouse bone marrow. Journal of immunological methods. Feb. 1, 1999;223(1):77-92.

NCBI Accession No. AAH89443 [gi:59807841] with Revision History—Feb. 15, 2005-Jun. 6, 2006.

NCBI Accession No. AK004116 [gi:12835174] with Revision History—Feb. 8, 2011-Sep. 2, 2005.

NCBI Accession No. BC089443 [gi:59807840] with Revision History—Feb. 15, 2005-Jun. 6, 2006.

NCBI Accession No. NM_028732 [gi:31980769] with Revision History—Mar. 20, 2001-May 7, 2006. 143249860 which replaced 31980768 is provided.

NCBI Accession No. NM_022153 [gi: 62339431] with Revision History—Apr. 7, 2005-Jun. 26, 2007.

NCBI Accession No. NM_026125 [gi:13385631] with Revision History—Mar. 20, 2001-May 7, 2006. 142365660 which replaced 13385631 is provided.

NCBI Accession No. NM_138530 [gi:51491892] with Revision History—Apr. 4, 2002-Nov. 18, 2006.

NCBI Accession No. NP_071436 [gi: 62339432] with Revision History—Apr. 7, 2005-Aug. 13, 2006.

NCBI Accession No. NP_080401 [gi:13385632] with Revision History—Mar. 20, 2001-May 7, 2006.

NCBI Accession No. X1_233720 [gi:109475938] with Revision History—Jan. 13, 2003-Jun. 22, 2006.

Nielsen MB, Marincola FM. Melanoma vaccines: the paradox of T cell activation without clinical response. Cancer chemotherapy and pharmacology. Jul. 1, 2000;46(1):S62-6.

Platt et al., J Allergy Clin Immunol 2014, 134: 262-268.

Sharpe AH, Freeman GJ. The B7-CD28 superfamily. Nature Reviews Immunology. Feb. 2002;2(2):116.

Shulman M, Wilde CD, Köhler G. A better cell line for making hybridomas secreting specific antibodies. Nature. Nov. 1978;276(5685):269.

Sica GL, Choi IH, Zhu G, Tamada K, Wang SD, Tamura H, Chapoval AI, Flies DB, Bajorath J, Chen L. B7-H4, a molecule of the B7 family, negatively regulates T cell immunity. Immunity. Jun. 1, 2003;18(6):849-61.

Son YI, Egawa SI, Tatsumi T, Redlinger Jr RE, Kalinski P, Kanto T. A novel bulk-culture method for generating mature dendritic cells from mouse bone marrow cells. Journal of immunological methods. Apr. 1, 2002;262(1-2):145-57.

Tuladharr, Natarajan G, Satoskar AR. Role of Co-stimulation in Leishmaniasis. International journal of biological sciences. 2011;7(9):1382.

Wang L, Le Mercier I, Putra J, Chen W, Liu J, Schenk AD, Nowak EC, Suriawinata AA, Li J, Noelle RJ. Disruption of the immune-checkpoint VISTA gene imparts a proinflammatory phenotype with predisposition to the development of autoimmunity. Proceedings of the National Academy of Sciences. Oct. 14, 2014;111(41):14846-51.

Warrington et al. Allergy, Asthma & Clinical Immunology 2011, 7 (Suppl 1):S1, 8 pages.

GenBank entry EGW09616.1 (Mar. 14, 2015) Online, [retrieved on Jun. 22, 2015 from http://www.ncbi.nih.gov/protein/EGW09616.1].

Wang et al., "Immune checkpoint protein VISTA regulate autoimmunity and anti-tumor immunity", J. Immunol. (May 2013) Meeting Abstract Supplement 190(53.35).

Xu et al., "The genomic sequence of the Chinese hamster ovary (CHO)-K1 cell line", Nature Biotechnology Aug. 2011, 29(8): 735-741.

Nomi, et al. "Clinical significance and therapeutic potential of the programmed death-1 ligand/programmed death-1 pathway in human pancreatic cancer," Clin Cancer Res. Apr. 1, 2007;13(7):2151-7.

Sequence alignment, 2014 2 pages (in U.S. Appl. No. 13/637,381).

Wang, et al. "VISTA, a novel mouse Ig superfamily ligand that negatively regulates T cell responses," J Exp Med. Mar. 14, 2011;208(3):577-92.

Norde, et al., "Coinhibitory molecules in hematologic malignancies: targets for therapeutic intervention," Blood. Jul. 26, 2012;120(4):728-36.

Sharma, et al., "Novel cancer immunotherapy agents with survival benefit: recent successes and next steps," Nat Rev Cancer. Oct. 24, 2011;11(11):805-12.

Bolhassani, et al. "Improvement of different vaccine delivery systems for cancer therapy," Mol Cancer. Jan. 7, 2011;10:3.

Picha, et al. "Protein engineering strategies for sustained glucagon-like peptide-1 receptor-dependent control of glucose homeostasis," Diabetes. Jul. 2008;57(7):1926-34.

Chan, et al. "Therapeutic antibodies for autoimmunity and inflammation," Nat Rev Immunol. May 2010;10(5):301-16.

GenBank Accession No. NP_083008 (Mar. 3, 2010).

GenBank Accession No. NP_071436 (Sep. 3, 2009).

\* cited by examiner

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: AP1049

<400> SEQUENCE: 1

Ser Ser Ala Cys Asp Trp Ile Lys Arg Ser Cys His
1               5                   10

VISTA ANTAGONIST AND METHODS OF USE

CROSS-REFERENCE TO RELATED APPLICATIONS

This application is a continuation of U.S. Ser. No. 14/534,793, filed Apr. 14, 2015, and also claims priority to PCT/US15/12752, filed Jan. 23, 2015 which PCT application claims priority to U.S. Provisional Ser. No. 61/927,061 filed Jan. 14, 2014, the contents of each, including the sequence listing, are incorporated herein by reference in their entireties.

This application includes as part of its disclosure a biological sequence listing which is being concurrently submitted through EFS-Web. Said biological sequence listing is contained in a file named "1143260o001005" which was created Oct. 29, 2019, and has a size of 616 bytes, and is hereby incorporated by reference in its entirety.

BACKGROUND

The immune system is tightly controlled by co-stimulatory and co-inhibitory ligands and receptors. These molecules provide not only a second signal for T cell activation but also a balanced network of positive and negative signals to maximize immune responses against infection while limiting immunity to self.

Induction of an immune response requires T cell expansion, differentiation, contraction and establishment of T cell memory. T cells must encounter antigen presenting cells (APCs) and communicate via T cell receptor (TCR)/major histocompatibility complex (MHC) interactions on APCs. Once the TCR/MHC interaction is established, other sets of receptor-ligand contacts between the T cell and the APC are required, i.e. co-stimulation via CD154/CD40 and CD28/B7.1-B7.2. The synergy between these contacts results in a productive immune response capable of clearing pathogens and tumors, and may be capable of inducing autoimmunity.

Another level of control has been identified, namely regulatory T cells ($T_{reg}$). This specific subset of T cells is generated in the thymus, delivered into the periphery, and is capable of constant and inducible control of T cells responses. Sakaguchi (2000) Cell 101(5):455-8; Shevach (2000) Annu. Rev. Immunol. 18:423-49; Bluestone and Abbas (2003) Nat. Rev. Immunol. 3(3):253-7. $T_{reg}$ are represented by a CD4+CD25+ phenotype and also express high levels of cytotoxic T lymphocyte-associated antigen-4 (CTLA-4), OX-40, 4-1BB and the glucocorticoid inducible TNF receptor-associated protein (GITR). McHugh, et al. (2002) Immunity 16(2):311-23; Shimizu, et al. (2002) Nat. Immun. 3(2):135-42. Elimination of $T_{reg}$ cells by 5 day neonatal thymectomy or antibody depletion using anti-CD25, results in the induction of autoimmune pathology and exacerbation of T cells responses to foreign and self-antigens, including heightened anti-tumor responses. Sakaguchi, et al. (1985) J. Exp. Med. 161(1):72-87; Sakaguchi, et al. (1995) J. Immunol. 155(3):1151-64; Jones, et al. (2002) Cancer Immun. 2:1. In addition, $T_{reg}$ have also been involved in the induction and maintenance of transplantation tolerance, since depletion of $T_{reg}$ with anti-CD25 monoclonal antibodies results in ablation of transplantation tolerance and rapid graft rejection. Jarvinen, et al. (2003) Transplantation 76:1375-9. Among the receptors expressed by $T_{reg}$ GITR seems to be an important component since ligation of GITR on the surface of Treg with an agonistic monoclonal antibody results in rapid termination of $T_{reg}$ activity, resulting in autoimmune pathology and ablation of transplantation tolerance.

Costimulatory and co-inhibitory ligands and receptors not only provide a "second signal" for T cell activation, but also a balanced network of positive and negative signal to maximize immune responses against infection while limiting immunity to self. The best characterized costimulatory ligands are B7.1 and B7.2, which are expressed by professional APCs, and whose receptors are CD28 and CTLA-4. Greenwald, et al. (2005) Annu Rev Immunol 23, 515-548; Sharpe and Freeman (2002) Nat Rev Immunol 2, 116-126. CD28 is expressed by naïve and activated T cells and is critical for optimal T cell activation. In contrast, CTLA-4 is induced upon T cell activation and inhibits T cell activation by binding to B7.1/B7.2, thus impairing CD28-mediated costimulation. CTLA-4 also transduces negative signaling through its cytoplasmic ITIM motif. Teft, et al. (2006). Annu Rev Immunol 24, 65-97. B7.1/B7.2 KO mice are impaired in adaptive immune response (Borriello, et al. (1997) Immunity 6, 303-313; Freeman, et al. (1993) Science 262, 907-909), whereas CTLA-4 KO mice can not adequately control inflammation and develop systemic autoimmune diseases. Chambers, et al. (1997) Immunity 7, 885-895; Tivol, et al. (1995) Immunity 3, 541-547; Waterhouse, et al. (1995) Science 270, 985-988. The B7 family ligands have expanded to include costimulatory B7-H2 (ICOS Ligand) and B7-H3, as well as co-inhibitory B7-H1 (PD-L1), B7-DC (PD-L2), B7-H4 (B7S1 or B7x), and B7-H6. See Brandt, et al. (2009) J Exp Med 206, 1495-1503; Greenwald, et al. (2005) Annu Rev Immunol 23: 515-548.

Inducible costimulatory (ICOS) molecule is expressed on activated T cells and binds to B7-H2. See Yoshinaga, et al. (1999) Nature 402, 827-832. ICOS is important for T cell activation, differentiation and function, as well as essential for T-helper-cell-induced B cell activation, Ig class switching, and germinal center (GC) formation. Dong, et al. (2001) Nature 409, 97-101; Tafuri, et al. (2001) Nature 409, 105-109; Yoshinaga, et al. (1999) Nature 402, 827-832. Programmed Death 1 (PD-1) on the other hand, negatively regulates T cell responses. PD-1 KO mice develop lupus-like autoimmune disease, or autoimmune dilated cardiomyopathy depending upon the genetic background. Nishimura, et al. (1999) Immunity 11, 141-151. Nishimura, et al. (2001) Science 291: 319-322. The autoimmunity most likely results from the loss of signaling by both ligands PD-L1 and PD-L2. Recently, CD80 was identified as a second receptor for PD-L1 that transduces inhibitory signals into T cells. Butte, et al. (2007) Immunity 27: 111-122. The receptor for B7-H3 and B7-H4 still remain unknown.

The best characterized co-stimulatory ligands are B7.1 and B7.2, which belong to the Ig superfamily and are expressed on professional APCs and whose receptors are CD28 and CTLA-4 (Greenwald, et al. (2005) Annu. Rev. Immunol. 23:515-548). CD28 is expressed by naïve and activated T cells and is critical for optimal T cell activation. In contrast, CTLA-4 is induced upon T cell activation and inhibits T cell activation by binding to B7.1/B7.2, impairing CD28-mediated co-stimulation. B7.1 and B7.2 KO mice are impaired in adaptive immune response (Borriello, et al. (1997) Immunity 6:303-313), whereas CTLA-4 knockout mice cannot adequately control inflammation and develop systemic autoimmune diseases (Tivol, et al. (1995) Immunity 3:541-547; Waterhouse, et al. (1995) Science 270:985-988; Chambers, et al. (1997) Immunity 7:885-895).

The B7 family ligands have expanded to include co-stimulatory B7-H2 (inducible T cell co-stimulator (ICOS)

ligand) and B7-H3, as well as co-inhibitory B7-H1 (PD-L1), B7-DC (PD-L2), B7-H4 (B7S1 or B7x), and B7-H6 (Greenwald, et al. (2005) supra; Brandt, et al. (2009) *J. Exp. Med.* 206:1495-1503). Accordingly, additional CD28 family receptors have been identified. ICOS is expressed on activated T cells and binds to B7-H2 (Yoshinaga, et al. (1999) *Nature* 402:827-832). ICOS is a positive coregulator, which is important for T cell activation, differentiation, and function (Yoshinaga, et al. (1999) supra; Dong, et al. (2001) *Nature* 409:97-101). In contrast, PD-1 (programmed death 1) negatively regulates T cell responses. PD-1 knockout mice develop lupus-like autoimmune disease or autoimmune dilated cardiomyopathy (Nishimura, et al. (1999) *Immunity* 11:141-151; Nishimura, et al. (2001) *Science* 291:319-322). The autoimmunity most likely results from the loss of signaling by both ligands PD-L1 and PD-L2. Recently, CD80 was identified as a second receptor for PD-L1 that transduces inhibitory signals into T cells (Butte, et al. (2007) *Immunity* 27:111-122).

The two inhibitory B7 family ligands, PD-L1 and PD-L2, have distinct expression patterns. PD-L2 is inducibly expressed on DCs and macrophages, whereas PD-L1 is broadly expressed on both hematopoietic cells and nonhematopoietic cell types (Okazaki & Honjo (2006) *Immunology* 27:195-201; Keir, et al. (2008) *Annu. Rev. Immunol.* 26:677-704). Consistent with the immune-suppressive role of PD-1 receptor, a study using PD-L1$^{-/-}$ and PD-L2$^{-/-}$ mice has shown that both ligands have overlapping roles in inhibiting T cell proliferation and cytokine production (Keir, et al. (2006) *J. Exp. Med.* 203:883-895). PD-L1 deficiency enhances disease progression in both the non-obese diabetic model of autoimmune diabetes and the mouse model of multiple sclerosis (experimental autoimmune encephalomyelitis (EAE); Anasari, et al. (2003) *J. Exp. Med.* 198:63-69; Salama, et al. (2003) *J. Exp. Med.* 198:71-78; Latchman, et al. (2004) *Proc. Natl. Acad. Sci. USA.* 101:10691-10696). PD-L1$^{-/-}$ T cells produce elevated levels of the proinflammatory cytokines in both disease models. In addition, bone marrow chimera experiments have demonstrated that the tissue expression of PD-L1 (i.e., within pancreas) uniquely contributes to its capacity of regionally controlling inflammation (Keir, et al. (2006) supra; Keir, et al. (2007) *J. Immunol.* 179:5064-5070; Grabie, et al. (2007) *Circulation.* 116:2062-2071). PD-L1 is also highly expressed on placental syncytiotrophoblasts, which critically control the maternal immune responses to allogeneic fetus (Guleria, et al. (2005) *J. Exp. Med.* 202:231-237).

Consistent with its immune-suppressive role, PD-L1 potently suppresses antitumor immune responses and helps tumors evade immune surveillance. PD-L1 can induce apoptosis of infiltrating cytotoxic CD8$^+$ T cells, which express a high level of PD-1 (Dong, et al. (2002) *Nature* 409:97-101; Dong & Chen (2003) *J. Mol. Med.* 81:281-287). Studies have shown that blocking the PD-L1-PD-1 signaling pathway, in conjunction with other immune therapies, prevents tumor progression by enhancing antitumor cytotoxic T lymphocyte activity and cytokine production (Iwai, et al. (2002) *Proc. Natl. Acad. Sci. USA* 99:12293-12297; Blank, et al. (2004) *Cancer Res.* 64:1140-1145; Blank, et al. (2005) *Cancer Immunol. Immunother.* 54:307-314; Geng, et al. (2006) *Int. J. Cancer.* 118:2657-2664). In addition, it has been shown that PD-L1 expression on dendritic cells promotes the induction of adaptive Foxp3$^+$CD4$^+$ regulatory T cells (aT$_{reg}$ cells), and PD-L1 is a potent inducer of aT$_{reg}$ cells within the tumor microenvironment (Wang, et al. (2008) *Proc. Natl. Acad. Sci. USA.* 105:9331-9336).

An additional immune regulatory ligand, referred to as V-domain Ig suppressor of T cell activation (VISTA) or PD-L3, has been recently identified as an upregulated molecule in a T cell transcriptional profiling screen. (Wang, et al. (2011) *J. Exp. Med.* 208:577; WO 2011/120013). It has been shown that the extracellular Ig domain of VISTA shares significant sequence homology with the B7 family ligands PD-L1 and PD-L2, albeit with unique structural features that distinguish it from the B7 family members.

VISTA is primarily expressed on hematopoietic cells, and VISTA expression is highly regulated on myeloid antigen-presenting cells (APCs) and T cells. Expression of VISTA on antigen presenting cells (APCs) suppresses T cell responses by engaging its counter-receptor on T cells during cognate interactions between T cells and APCs. VISTA blockade enhances T cell-mediated immunity in an autoimmune disease model, suggesting its unique and non-redundant role in controlling autoimmunity when compared with other inhibitory B7 family ligands such as PD-L1 and PD-L2. In addition, VISTA blockade enhances anti-tumor immunity and suppressed tumor growth in preclinical murine tumor models (WO 2011/120013). In this regard, therapeutic intervention of the VISTA inhibitory pathway represents a novel approach to modulate T cell-mediated immunity for treating diseases such as viral infection and cancer.

SUMMARY OF THE INVENTION

The present invention provides an isolated VISTA antagonist that comprises a peptide that is identical to the amino acid sequence of SEQ ID NO:1 (Ser-Ser-Ala-Cys-Asp-Trp-Ile-Lys-Arg-Ser-Cys-His), or a multimer, conjugate, analog, derivative or mimetic thereof.

In one embodiment, the isolated VISTA antagonist comprises a peptide which is identical to the amino acid sequence of SEQ ID NO:1 (Ser-Ser-Ala-Cys-Asp-Trp-Ile-Lys-Arg-Ser-Cys-His), or which comprises a peptide having an amino acid sequence that differs from SEQ ID NO:1 by at most 2 amino acid residues, or an multimer, conjugate, analog, derivative or mimetic thereof. In another embodiment, the isolated VISTA antagonist comprises a peptide having an amino acid sequence that differs from SEQ ID NO:1 by at most 1 amino acid residue, or an multimer, conjugate, analog, derivative or mimetic thereof. In yet another embodiment, the isolated VISTA antagonist comprises a peptide which is identical to the amino acid sequence of SEQ ID NO:1 (Ser-Ser-Ala-Cys-Asp-Trp-Ile-Lys-Arg-Ser-Cys-His), or a multimer, or conjugate thereof. In a specific embodiment, the isolated VISTA antagonist consists of the amino acid sequence of SEQ ID NO:1 (Ser-Ser-Ala-Cys-Asp-Trp-Ile-Lys-Arg-Ser-Cys-His).

In one embodiment, the cysteine residues at positions 4 and 11 of SEQ ID NO:1 (Ser-Ser-Ala-Cys-Asp-Trp-Ile-Lys-Arg-Ser-Cys-His), or their corresponding positions in a variant of said peptide, form a disulfide bridge.

In another embodiment, the isolated VISTA antagonist has been modified to improve binding affinity and/or stability. In a specific embodiment, the isolated VISTA antagonist has been modified by PEG, acetylation, XTEN, albumin and/or multimerization.

In another embodiment, the isolated VISTA antagonist is directly or indirectly attached to an immunoglobulin polypeptide or a fragment thereof. The immunoglobulin polypeptide may comprise a human IgG1, IgG2, IgG3 or IgG4 constant region or fragment thereof. Preferably, the immunoglobulin polypeptide comprises a human IgG1 constant region or fragment thereof.

In yet another embodiment, the isolated VISTA antagonist comprises multiple, i.e., 2, 3, 4, 5, 6, 7 or more, copies of said peptide.

In a further embodiment, the isolated VISTA antagonist comprises another moiety that targets said peptide to a target site. The targeting moiety may be selected from an antibody or ligand that binds to an antigen, a receptor expressed by the target cell or an infectious agent.

In yet a further embodiment, the isolated VISTA antagonist is attached to another moiety or another copy of said antagonist via a linker. The linker may be a peptide that permits the antagonist to interact with VISTA expressed on the surface of a target cell.

In a further embodiment, the isolated VISTA antagonist is directly or indirectly attached to a detectable label or therapeutic agent.

In several of the embodiments, the isolated VISTA antagonist binds to the extracellular domain of VISTA and disrupts its interaction with a VISTA receptor and/or reduces or inhibits VISTA-mediated T cell suppression.

In one embodiment, the isolated VISTA antagonist elicits anti-tumor and/or anti-viral activity.

Additionally, the invention contemplates a composition suitable for therapeutic, prophylactic or diagnostic use comprising a therapeutically, prophylactically or diagnostically effective amount of the isolated VISTA antagonist.

In one embodiment, the composition further comprises a pharmaceutically acceptable carrier, diluent, solubilizer, preservative or mixture thereof.

In another embodiment, the composition further comprises another therapeutic agent, e.g., an anti-cancer agent, an anti-viral agent, a cytokine or an immune agonist. In a particular embodiment, the other therapeutic agent is selected from CTLA-4-Ig, anti-PD-1, PD-L1 or PD-L2 fusion proteins, and EGFR antagonists.

In one embodiment, the composition is suitable for subcutaneous administration or intravenous administration.

Moreover, the present invention further contemplates an isolated nucleic acid sequence encoding a VISTA antagonist peptide, analog, derivative or mimetic thereof disclosed herein, a vector containing the isolated nucleic acid sequence, and a host cell comprising the isolated nucleic acid sequence or the vector.

In one embodiment, the host cell is a mammalian cell, a bacterial cell, a fungal cell, a yeast cell, an avian cell or an insect cell.

The present invention further contemplates a method of expressing a VISTA antagonist peptide, analog, derivative or mimetic thereof comprising culturing the host cell under conditions that provide for expression of said peptide, analog, derivative or mimetic thereof.

Furthermore, the present invention contemplates various uses of the isolated VISTA antagonist.

In one embodiment, the invention provides a method for blocking, inhibiting or neutralizing VISTA-mediated T cell suppression, comprising administering to a subject in need thereof an effective amount of an isolated VISTA antagonist disclosed herein or a composition containing said isolated VISTA antagonist.

In another embodiment, the invention provides a method for stimulating an immune response in a subject, comprising administering to the subject in need thereof an effective amount of an isolated VISTA antagonist disclosed herein or a composition containing said isolated VISTA antagonist. Such a method may be used for treating cancer in a subject.

The subject may have cancer and/or an infection selected from the group consisting of bacterial, viral, parasitic and fungal infections.

The bacterial infection may be caused by at least one bacterium selected from the group consisting of *Bordetella, Borrelia, Brucella, Burkholderia, Campylobacter, Chlamydia, Clostridium, Corynebacterium, Enterobacter, Enterococcus, Erwinia, Escherichia, Francisella, Haemophilus, Heliobacter, Legionella, Leptospira, Listeria, Mycobacterium, Mycoplasma, Neisseria, Pasteurella, Pelobacter, Pseudomonas, Rickettsia, Salmonella, Serratia, Shigella, Staphylococcus, Streptococcus, Treponema, Vibrio, Yersinia* and *Xanthomonas*.

The viral infection may be caused by at least one virus selected from the group consisting of Adenoviridae, Papillomaviridae, Polyomaviridae, Herpesviridae, Poxviridae, Hepadnaviridae, Parvoviridae, Astroviridae, Caliciviridae, Picornaviridae, Coronoviridae, Flaviviridae, Retroviridae, Togaviridae, Arenaviridae, Bunyaviridae, Filoviridae, Orthomyxoviridae, Paramyxoviridae, Rhabdoviridae, and Reoviridae. More specifically, the virus may be adenovirus, herpes simplex type 1, herpes simplex type 2, Varicella-zoster virus, Epstein-barr virus, cytomegalovirus, herpesvirus type 8, papillomavirus, BK virus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), influenza, guanarito virus, Junin virus, Lassa virus, Machupo virus, Sabia virus, Crimean-Congo hemorrhagic fever virus, ebola virus, Marburg virus, measles virus, mumps virus, parainfluenza, respiratory syncytial virus, human metapneumovirus, Hendra virus, Nipah virus, rabies, Hepatitis D, rotavirus, orbivirus, coltivirus or Banna virus.

The fungal infection may be selected from the group consisting of thrush, candidiasis, cryptococcosis, histoplasmosis, blastomycosis, aspergillosis, coccidioidomycosis, paracoccidiomycosis, sporotrichosis, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, or rhinosporidiosis.

The parasitic infection may be caused by at least one parasite selected from the group consisting of Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis, Histomonas meleagridis; Secementea; Trichuris trichiura, Ascaris lumbricoides, Enterobius vermicularis, Ancylostoma duodenale, Necator americanus, Strongyloides stercoralis, Wuchereria bancrofti, Dracunculus medinensis; blood flukes, liver flukes, intestinal flukes, lung flukes; Schistosoma mansoni, Schistosoma haematobium, Schistosoma japonicum, Fasciola hepatica, Fasciola gigantica, Heterophyes heterophyes, and Paragonimus westermani.

In another embodiment, the invention provides a method for enhancing anti-cancer or anti-tumor immunity, comprising administering to a subject in need thereof an effective amount of an isolated VISTA antagonist disclosed herein or a composition containing said isolated VISTA antagonist.

In another embodiment, the invention provides a method for treating or preventing cancer, inhibiting tumor invasion and/or cancer metastasis, comprising administering to a subject in need thereof an effective amount of an isolated VISTA antagonist disclosed herein or a composition containing said isolated VISTA antagonist.

The cancer may be selected from the group consisting of carcinoma, lymphoma, blastoma, sarcoma, leukemia, lymphoid malignancies, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma, head and neck cancer, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; post-transplant lymphoproliferative disorder (PTLD), abnormal vascular proliferation associated with phakomatoses, edema (such as that associated with brain tumors), and Meigs' syndrome.

In yet another embodiment, the invention provides a method for treating or preventing a viral infection, comprising administering to a subject in need thereof an effective amount of an isolated VISTA antagonist disclosed herein or a composition containing said isolated VISTA antagonist.

These methods may further comprise the administration of another therapeutic agent, wherein said peptide and therapeutic may be separately or jointly administered, at the same or different times.

In one embodiment, the other therapeutic agent is an anti-cancer agent, an anti-viral or other anti-infectious agent, a cytokine or an immune agonist. Preferably, the other therapeutic agent is selected from CTLA-4-Ig, anti-PD-1, PD-L1 or PD-L2 fusion proteins, and EGFR antagonists.

Finally, the present invention also contemplates a method for mapping the active site of VISTA, comprising: (a) incubating an isolated VISTA fusion protein with an isolated VISTA antagonist comprising a peptide that is identical to the amino acid sequence of SEQ ID NO:1 (Ser-Ser-Ala-Cys-Asp-Trp-Ile-Lys-Arg-Ser-Cys-His), or which comprises a peptide having an amino acid sequence which differs from SEQ ID NO:1 by at most 2 amino acid residues or an multimer, conjugate, analog, derivative or mimetic thereof; and (b) determining the binding site of the isolated VISTA antagonist.

In one embodiment, the active site of VISTA binds to a VISTA receptor and mediates immune suppression. In another embodiment, step (b) comprises domain deletion, domain swapping, amino acid mutagenesis, foot printing, NMR, X-ray crystallography or homology modeling.

DETAILED DESCRIPTION OF THE INVENTION

Figure 1:
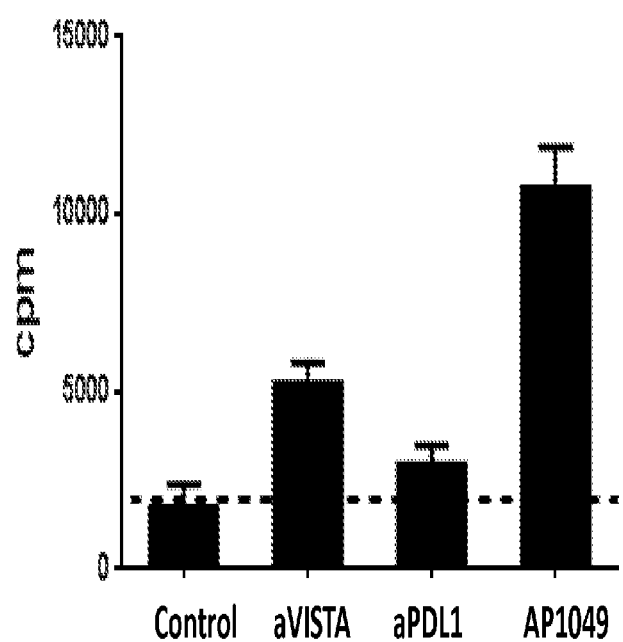
FIG. 1 shows that a VISTA antagonist peptide (SEQ ID NO:1) significantly enhances the proliferation of T cells as compared to an anti-VISTA antibody (aVISTA) and an anti-PD-L1 antibody (aPDL1). Myeloid CD11B+ APCs were incubated with OT2 CD4+ T cells, antigen, and a monoclonal antibody (aVISTA or aPDL1) or AP1049. Proliferation of T cells was measured by tritium incorporation at 72 hours.

In order that the invention herein described may be fully understood, the following detailed description is set forth. Various embodiments of the invention are described in detail and may be further illustrated by the provided examples.

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

Definitions

As used in the description herein and throughout the claims that follow, the meaning of "a," "an," and "the" includes plural reference unless the context clearly dictates otherwise.

"Antagonist," as used herein, refers to a compound (preferably a peptide) that opposed the physiological effects of another compound. For example, at the receptor level, an antagonist is a compound that opposes the receptor-associated response normally induced by another agent that binds to and activates the biological activity the receptor. Likewise, at the ligand level, an antagonist is a compound that opposes the ligand-associated response normally induced when the ligand binds to its target receptor and/or accessory factors. In a specific embodiment, a VISTA antagonist is a compound, e.g., a peptide or analog, derivative or mimetic thereof, that binds to VISTA and opposes one or more of its biological activities, e.g., VISTA-mediated T cell suppression and/or VISTA-mediated suppression of anti-tumor immunity, thereby enhancing T cell-mediated immunity and/or anti-tumor immunity.

"Analog," as used herein, refers to a compound (preferably a peptide) whose structure is related to that of a given compound (preferably a peptide) but differs in chemical and biological properties.

"Antigen presenting cell," as used herein, refers broadly to professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine.) Amino acid analogs refers to compounds that have the same basic chemical structure as a naturally occurring amino acid (i.e., a carbon that is bound to a hydrogen, a carboxyl group, an amino group), and an R group (e.g., homoserine, norleucine, methionine sulfoxide, methionine methyl sulfonium.) Analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Allergic disease," as used herein, refers broadly to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation.

"Autoimmune disease" as used herein, refers broadly to a disease or disorder arising from and directed against an individual's own tissues or a co-segregate or manifestation thereof or resulting condition therefrom.

"Cancer," as used herein, refers broadly to any neoplastic disease (whether invasive or metastatic) characterized by abnormal and uncontrolled cell division causing malignant growth or tumor (e.g., unregulated cell growth.)

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. "Silent variations" are one species of conservatively modified nucleic acid variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Costimulatory receptor," as used herein, refers broadly to receptors which transmit a costimulatory signal to an immune cell, e.g., CD28 or ICOS.

"Cytoplasmic domain," as used herein, refers broadly to the portion of a protein which extends into the cytoplasm of a cell.

"Derivative" or "peptide derivative," as used herein, contain a modification of one or more amino acid residues or a linker group or other covalently linked group. Non-limiting examples of derivatives include N-acyl derivatives of the amino terminal or of another free amino group, esters of the carboxyl terminal or of another free carboxyl or hydroxy group, amides of the carboxyl terminal or of another free carboxyl group produced by reaction with ammonia or with a suitable amine, glycosylated derivatives, hydroxylated derivatives, nucleotidylated derivatives, ADP-ribosylated derivatives, pegylated derivatives, phosphorylated derivatives, derivatives conjugated to lipophilic moieties, and derivatives conjugated to an antibody or other biological ligand. Also included among the chemical derivatives are those obtained by modification of the peptide bond —CO—NH—, for example by reduction to —CH$_2$—NH— or alkylation to —CO—N(alkyl)-. Preferred derivatisation include, but are not limited tom C-terminal amidation and N-terminal acetylation, which removes the negative charge of the C terminus or removes the positive charge at the N-terminus, respectively. Blocking of the C- or N-terminus, such as by C-terminal amidation or N-terminal acetylation, may improve proteolytic stability due to reduced susceptibility to exoproteolytic digestion.

Peptide derivatives having a C-terminal amide are represented with "NH$_2$" at the C-terminus.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Extracellular domain," as used herein refers broadly to the portion of a protein that extend from the surface of a cell.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to refer to a cell into which a nucleic acid molecule of the invention, such as a recombinant expression vector of the invention, has been introduced. Host cells may be prokaryotic cells (e.g., E. coli), or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, progeny may not, in fact, be identical to the parent cell, but are still included within the scope of the term as used herein.

"Immune response," as used herein, refers broadly to T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "down modulation" with reference to the immune response includes a diminution in any one or more immune responses, while the term "up modulation" with reference to the immune response includes an increase in any one or more immune responses. It will be understood that up modulation of one type of immune response may lead to a corresponding downmodulation in another type of immune response. For example, up modulation of the production of certain cytokines (e.g., IL-10) can lead to downmodulation of cellular immune responses.

"Inflammatory disease," as used herein, refers broadly to chronic or acute inflammatory diseases.

"Detectable label" as used herein, refers broadly to a composition detectable by spectroscopic, photochemical, biochemical, immunochemical, chemical, or other physical means.

"Mimetic" or "peptidomimetic," as used herein, refers to a fully or partially synthetic peptide that has the activity of a given peptide. Such a mimetic or peptidomimetic comprises one or more amino acid residues that is an artificial chemical mimetic of a corresponding naturally occurring amino acid, naturally occurring amino acid polymers and non-naturally occurring amino acid polymers.

Modifications of the VISTA and VISTA conjugate polypeptides described herein include, but are not limited to N-terminus modification, C-terminus modification, peptide bond modification (e.g., $CH_2$—NH, $CH_2$—S, $CH_2$—S=O, O=C—NH, $CH_2$—O, $CH_2$—$CH_2$, S=C—NH, CH=CH or CF=CH), backbone modifications, and residue modification, e.g., by the addition of carbohydrate residues to form glycoproteins, by the addition of chemical residues such as PEG and/or XTEN, etc. Methods for preparing peptidomimetic compounds are well known in the art. Martin, (2010).

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Sequence identity," as used herein, refers broadly to a degree of similarity between a nucleic acid sequence and a reference nucleic acid sequence or between a polypeptide sequence and a reference polypeptide sequence. Sequence identity (also synonymous with "homology") may be partial or complete. Complete sequence identity indicates that the nucleic acid or amino acid sequences are identical, i.e., 100% sequence identity. A partially homologous nucleic acid or amino acid sequence is one that is not identical to the reference nucleic acid or amino acid sequence. The degree of homology can be determined by sequence comparison, e.g., 60% identity, 70% identity, 80% identity, 90% identity, 95% identity, 97% identity, 98% identity, or 99% identity.

"Signs" of disease, as used herein, refers broadly to any abnormality indicative of disease, discoverable on examination of the patient; an objective indication of disease, in contrast to a symptom, which is a subjective indication of disease.

"Subject," as used herein, refers broadly to any animal that is in need of treatment either to alleviate a disease state or to prevent the occurrence or reoccurrence of a disease state. Also, "subject" as used herein, refers broadly to any animal that has risk factors, a history of disease, susceptibility, symptoms, and signs, was previously diagnosed, is at risk for, or is a member of a patient population for a disease. The subject may be a clinical patient such as a human or a veterinary patient such as a companion, domesticated, livestock, exotic, or zoo animal. The term "subject" may be used interchangeably with the term "patient."

"Symptoms" of disease as used herein, refers broadly to any morbid phenomenon or departure from the normal in structure, function, or sensation, experienced by the patient and indicative of disease.

"T cell," as used herein, refers broadly to CD4+ T cells and CD8+ T cells. The term T cell also includes both T helper 1 type T cells and T helper 2 type T cells.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., inflammation, pain).

"Transmembrane domain," as used herein, refers broadly to an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In an embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, et al. (1996) *Annu. Rev. Neurosci.* 19:235-263.

"Tumor," as used herein, refers broadly to at least one cell or cell mass in the form of a tissue neoformation, in particular in the form of a spontaneous, autonomous and irreversible excess growth, which is more or less disinhibited, of endogenous tissue, which growth is as a rule associated with the more or less pronounced loss of specific cell and tissue functions. This cell or cell mass is not effectively inhibited, in regard to its growth, by itself or by the regulatory mechanisms of the host organism, e.g., melanoma or carcinoma. Tumor antigens not only include antigens present in or on the malignant cells themselves, but also include antigens present on the stromal supporting tissue of tumors including endothelial cells and other blood vessel components.

"Vector," as used herein, refers broadly to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. The techniques and procedures are generally performed according to conventional methods well known in the art and as described in various general and more specific references that are cited and discussed throughout the present specification. See, e.g., Sambrook, et al. (2001) *Molec. Cloning: Lab. Manual* [3$^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein.

The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

VISTA and VISTA Antagonists

This application relates to a peptide antagonist that can recognize and suppress the inhibitory activity of VISTA. This peptide, designated herein as AP1049, was discovered through phage display and shown to exhibit superior bioactivity when compared to an anti-VISTA monoclonal antibody. Given its neutralizing activity, AP1049 can be used to, e.g., treat cancer and/or pathogenic, i.e., bacterial, fungal, parasite or viral infections and enhance anti-tumor immune responses and suppress tumor growth.

Accordingly, the present invention is a VISTA antagonistic peptide, as well as multimers, conjugates, analogs, derivatives and mimetics thereof and methods of using this peptide to inhibit or suppress the activity of VISTA. As used herein, the term "peptide" denotes an amino acid polymer that is composed of at least two amino acids covalently linked by an amide bond. Peptides of the present invention are desirably 10 to 20 residues in length, or more desirably 12 to residues in length. In certain embodiments, a VISTA antagonistic peptide is a 12 to 20 residue peptide containing the amino acid sequence of SEQ ID NO:1. In other embodiments of the present invention, the isolated VISTA antagonist comprises a peptide that is identical to the amino acid sequence of SEQ ID NO:1 (Ser-Ser-Ala-Cys-Asp-Trp-Ile-Lys-Arg-Ser-Cys-His), or which comprises a peptide having an amino acid sequence that differs from SEQ ID NO:1 by at most 1 amino acid residue or at most 2 amino acid residues, or an multimer, conjugate, analog, derivative or mimetic thereof. In yet other embodiments of the invention, the isolated VISTA antagonist consists of the amino acid sequence of SEQ ID NO:1 (Ser-Ser-Ala-Cys-Asp-Trp-Ile-Lys-Arg-Ser-Cys-His).

In certain embodiments of the present invention, cysteine residues at positions 4 and 11 of the VISTA antagonistic peptide (or their corresponding positions in a variant of the VISTA antagonist) form a disulfide bridge.

In accordance with the present invention, multimers, conjugates, analogs, derivatives and mimetics of the peptide of the invention are also provided.

An analog is a molecule that differs in chemical structure from a parent compound, for example a homolog (differing by an increment in the chemical structure, such as a difference one amino acid residue), a structure that differs by one or more functional groups, or a change in ionization. Structural analogs are often found using quantitative structure activity relationships (QSAR), with techniques such as those disclosed in Remington (*The Science and Practice of Pharmacology*, 19th Edition (1995), chapter 28).

Analogs can be prepared by modifying the amino acids sequence of SEQ ID NO:1. The simplest modifications involve the substitution of one or more amino acids for amino acids having similar physiochemical and/or structural properties. These so-called conservative substitutions are likely to have minimal impact on the activity and/or structure of the resultant peptide. Examples of conservative substitutions include substituting a serine with a threonine, substituting alanine with a serine or valine, substituting aspartic acid with glutamic acid, substituting tryptophan with a tyrosine, substituting isoleucine with leucine or valine, substituting arginine with lysine, and/or substituting histidine with arginine or lysine. Conservative substitutions generally maintain (a) the structure of the peptide backbone in the area of the substitution, for example, as a helical conformation, (b) the charge or hydrophobicity of the molecule at the target site, or (c) the bulk of the side chain.

Amino acid substitutions are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having non-polar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Additional amino acids that are classified in each of the above groups are known to those of ordinary skill in the art.

As used herein, a peptide derivative is a molecule which retains the primary amino acids of the peptide, however, the N-terminus, C-terminus, and/or one or more of the side chains of the amino acids therein have been chemically altered or derivatized. Such derivatized peptides include, for example, naturally occurring amino acid derivatives, for example, 4-hydroxyproline for proline, 5-hydroxylysine for lysine, homoserine for serine, ornithine for lysine, and the like. Other derivatives or modifications include, e.g., a label, such as fluorescein or tetramethylrhodamine; or one or more post-translational modifications such as acetylation, amidation, formylation, hydroxylation, methylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Brand, et al. (1996) *Am. J. Physiol. Cell. Physiol.* 270:C1362-C1369).

In addition, a peptide derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245: 1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or mimetic of the invention into the cell.

While a peptide of the invention can be derivatized with by one of the above indicated modifications, it is understood that a peptide of this invention may contain more than one of the above described modifications within the same peptide.

A mimetic or peptidomimetic refers to a synthetic chemical compound which has substantially the same structural and/or functional characteristics of a peptide of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit the activity of VISTA.

The phrase "substantially the same," when used in reference to a mimetic or peptidomimetic, means that the mimetic or peptidomimetic has one or more activities or functions of the referenced molecule, e.g., the ability to enhance T cell proliferation.

There are clear advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, a peptide of this invention has utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring VISTA activity.

Peptide mimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a peptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in *Chemistry and Biochemistry of Amino Acids, Peptides and Proteins*, 7:267-357, "Peptide and Backbone Modifications," Marcel Decker, N.Y.).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenyl-phenylalanine; and D- or L-2-indole(alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N—C—N—R') including, for example, 1-cyclohexyl-3(2-morpholinyl-(4-ethyl)carbodiimide or 1-ethyl-3 (4-azonia-4,4-dimetholpentyl)carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, a peptidomimetic of the present invention can also include one or more of the modifications described herein for derivatized peptides, e.g., a detectable label (such as an effector label or a radionuclide), a therapeutic agent (such as a chemotherapeutic agent), one or more post-translational modifications, or cell-penetrating sequence.

For example, the VISTA antagonists described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, β-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin, luciferase, and aequorin. Further exemplary radioactive materials include, but are not limited to, bismuth-213 ($^{213}$Bs), carbon-14 ($^{14}$C), carbon-11 ($^{11}$C), chlorine-(Cl$^{18}$), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-125 ($^{125}$I), iodine-123 ($^{124}$I), iodine-124 ($^{124}$I), iodine-131 ($^{131}$I), iridium-192 ($^{192}$Ir), iron-59 ($^{59}$Fe), krypton-81 ($^{81}$Kr), lead-212 ($^{212}$Pb), lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{89}$Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y).

Additionally, the VISTA antagonists provided herein may be modified to add a therapeutic agent including, but not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g., IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and Pseudomonas toxin may be conjugated to the VISTA antagonists to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419.

Furthermore, the VISTA antagonists described herein may be conjugated to a radionuclide that emits alpha or beta particles (e.g., radioimmunoconjuagtes). Such radioactive isotopes include but are not limited to beta-emitters such as phosphorus-32 ($^{32}$P), scandium-47 ($^{47}$Sc), copper-67 ($^{67}$Cu), gallium-67 ($^{67}$Ga), yttrium-88 ($^{88}$Y), yttrium-90 ($^{90}$Y), iodine-125 ($^{125}$I), iodine-131 ($^{131}$I), samarium-153 ($^{153}$Sm), lutetium-177 ($^{177}$Lu), rhenium-186 ($^{186}$Re), rhenium-188 ($^{188}$Re), and alpha-emitters such as astatine-211 (211At), lead-212 ($^{212}$Pb), bismuth-212 ($^{212}$Bi), bismuth-213 ($^{213}$Bi) or actinium-225 (225Ac).

Methods are known in the art for conjugating a VISTA antagonist described herein to a label, such as those methods described by Hunter, et al (1962) *Nature* 144: 945; David, et al. (1974) *Biochemistry* 13: 1014; Pain, et al. (1981) *J. Immunol. Meth.* 40: 219; and Nygren (1982) *Histochem and Cytochem,* 30: 407.

Additionally, the VISTA antagonists described herein may comprise another moiety, i.e., a "targeting moiety," that targets the antagonist peptide to a target site (such as a cancer cell, a tumor, a virally-infected cell, etc). The targeting moiety may be selected from an antibody or ligand that binds to an antigen, a receptor expressed by the target cell or an infectious agent.

The VISTA antagonist (as well as multimers, conjugates, analogs, derivatives and mimetics thereof) may also be directly or indirectly attached to an immunoglobulin polypeptide or a fragment thereof, e.g., a antibody constant region.

A "conjugate," as used herein, refers to a compound having at least one isolated VISTA antagonist peptide and one immunoglobulin polypeptide or a fragment thereof, e.g., antibody constant region, joined at the polypeptide level, with or without the use of a linker. A conjugate may be a fusion polypeptide produced as the result of joining at the nucleic acid level of genes encoding at least one natriuretic peptide and one antibody constant region, with or without a coding sequence for a peptide linker.

Such VISTA antagonist peptide-antibody conjugates may have a higher serum stability, e.g., at least 20%, preferably at least 30%, 50%, 80%, 100%, 200% or more, increase in the serum half-life when compared with the antagonist peptide without the antibody constant region under the same conditions. A human antibody, e.g., a human IgG, such as IgG1, IgG2, IgG3 or IgG4, is frequently used to derive a constant region or a fragment thereof for the purpose of making a natriuretic peptide conjugate of this invention.

As used herein, an "antibody (or immunoglobulin) constant region" refers to a polypeptide that corresponds to at least a portion of the constant region of an antibody heavy chain or light chain, such portion including at least one constant domain (e.g., the constant domain of CL or one of the constant domains of $C_H$). For example, an "antibody constant region" used for making the conjugates of this invention may be derived from an antibody heavy chain and include two out of three ($C_H2$ and $C_H3$ for IgA, IgD, and IgG) or three out of four ($C_H2$, CH3, and CH4, for IgE and IgM) constant domains; the first constant domain ($C_H1$) may be present in some cases but may be excluded in others. Such an antibody constant region can be obtained by a variety of means, e.g., by a recombinant method or synthetic method, or by purification subsequent to enzymatic digestion, for instance, pepsin or papain digestion of an intact antibody or an antibody heavy or light chain.

Further encompassed by this term as used in this application are polypeptides having a substantial sequence identity (for instance, at least 80%, 85%, 90%, 95% or more) to the corresponding amino acid sequence of an antibody heavy or light chain constant region or a portion thereof that contains at least one constant domain nearest to the C-terminus of the antibody chain, so long as the presence of such an "antibody constant region" in a VISTA antagonist peptide-antibody constant region conjugate renders the conjugate a higher serum stability.

Additionally, the peptide, multimer, conjugate, analog, derivative or mimetic may be modified to increase certain properties, e.g., biological half life. Various approaches are possible including, but not limited to, N-terminal modification/conjugation (e.g., lipidation or acetylation), C-terminal modification/conjugation (e.g., lipidation or acetylation), amino acid substitutions (i.e., substitution of natural amino acid with unnatural amino acids, such as D-conformation, N-methylation, tetra-substitution, beta-amino acids, etc.), peptide backbone modifications (e.g., chemical modification of peptide bonds, such as simple reductions or replacement of carbonyl or amide groups with esters, sulfides and alkyls), side chain modifications and/or cyclization (e.g., disulfide bond formation).

In one embodiment, the peptide may be pegylated to, e.g., increase the biological (e.g., serum) half life of the antibody. To pegylate a peptide, typically it is reacted with polyethylene glycol (PEG), such as a reactive ester or aldehyde derivative of PEG, under conditions in which one or more PEG groups become attached to the peptide. Preferably, the pegylation is carried out via an acylation reaction or an alkylation reaction with a reactive PEG molecule (or an analogous reactive water-soluble polymer.

Similarly, in another embodiment, a peptide, multimer, conjugate, analog, derivative or mimetic may be modified by conjugation of polysialic acid (PSA) to increase half-life.

Additionally, the peptide, multimer, conjugate, analog, derivative or mimetic may be modified, e.g., genetically fused or chemically conjugated, to comprise extended recombinant polypeptide (XTEN), through a process called XTENylation, to improve its half life. XTEN is a long, hydrophilic, and unstructured protein-based polymer of 864 amino acids. See, e.g., WO 2013/130683 which is herein expressly incorporated by reference in its entirety. When attached to a molecule of interest, greatly increases the effective size of the molecule, thereby prolonging its presence in serum by slowing kidney clearance in a manner analogous to that of PEG. In addition to slowing kidney clearance, attachment to XTEN can also inhibit receptor-mediated clearance by reducing the ligand's affinity for its receptor. XTEN coupling chemistries include, but are not limited to, Thiol-XTEN; Maleimide-XTEN; Alkyne-XTEN; and Iodoacetyl-XTEN.

Moreover, the peptide, multimer, conjugate, analog, derivative or mimetic may be modified with recombinant albumin, e.g., Novozymes Recombumin®, to improve half life. The peptide can be genetically fused or chemically conjugated to a recombinant albumin using standard protocols.

Furthermore, the peptide, multimer, conjugate, analog, derivative or mimetic may be modified by the addition and/or removal of specific amino acids to and/or from the peptide. For example, a number of specific amino acids may be added to the peptide, thereby strengthening or tightening its molecular structure to make it less susceptible to biological degradation and, thus, providing a longer life-span in the blood, using, e.g., Zealand Structure Induced Probe (SIP®) tail technology.

Yet another exemplary method for improving the stability and therapeutic potential of peptides, analogs, derivatives or mimetics is multimerization. For example, a multimer may comprise two or more copies, e.g., 2, 3, 4, 5, 6, or more, of the isolated VISTA antagonist or variant thereof. Multimers include both homomultimers and heteromultimers. Multimerization can result in increased peptide stability, higher binding strength (due to multiple valencies in the molecule), and/or improved pharmacokinetic properties.

Another exemplary approach for improving the stability and, thus, therapeutic potential of the VISTA antagonist peptides, multimers, conjugates, analogs, derivatives or mimetics disclosed herein is the addition of acetyl groups to the N and/or C terminus of the peptide. Acetylation may protect the peptide from exopeptidases, thereby extending the half-life of the peptide.

Production of VISTA Antagonists

The peptide multimer, conjugate, analog, derivative or mimetic can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995) *Therapeutic Peptides and Proteins, Formulation, Processing and Delivery Systems*, Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes*, Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic Acids Res.* 25:3440-3444; Frenkel (1995) *Free Radic. Biol. Med.* 19:373-380; and Blommers (1994) *Biochemistry* 33:7886-7896).

Alternatively, a peptide of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology Vol. 182*, Academic Press. In particular embodiments, the peptide, or analog, derivative or mimetic thereof is isolated and/or purified to homogeneity (e.g. greater than 90% purity).

It is contemplated that the peptide disclosed herein can be used as a lead compound for the design and synthesis of compounds with improved efficacy, clearance, half-lives, and the like.

One approach includes structure-activity relationship (SAR) analysis (e.g., NMR analysis) to determine specific binding interactions between the peptide and VISTA to facilitate the development of more efficacious agents. Agents identified in such SAR analysis or from agent libraries can then be screened for their ability to, e.g., decrease the activity of VISTA and/or enhance T cell proliferation.

Pharmaceutical Compositions

The VISTA antagonist peptide, multimer, conjugate, analog, derivative and mimetic thereof described herein can be provided in a pharmaceutical composition.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration may occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations may be found, for example, in Grennaro (2005) [Ed.] *Remington: The Science and Practice of Pharmacy* [21$^{st}$ Ed.]

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The VISTA antagonist peptide, multimer, conjugate, analog, derivative and mimetic thereof described herein may be formulated into pharmaceutical compositions of various dosage forms. To prepare the pharmaceutical compositions of the invention, at least one VISTA antagonist as the active ingredient may be intimately mixed with appropriate carriers and additives according to techniques well known to those skilled in the art of pharmaceutical formulations. See Grennaro (2005) [Ed.] *Remington: The Science and Practice of Pharmacy* [21$^{st}$ Ed.] For example, the antagonists described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, arachis oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, the VISTA antagonist peptides, multimers, conjugates, analogs, derivatives and mimetics thereof may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The VISTA and VISTA conjugate may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

A person of skill in the art would be able to determine an effective dosage and frequency of administration through routine experimentation, for example guided by the disclosure herein and the teachings in Goodman, et al. (2011) *Goodman & Gilman's The Pharmacological Basis of Therapeutics* [12$^{th}$ Ed.]; Howland, et al. (2005) *Lippincott's Illustrated Reviews: Pharmacology* [2$^{nd}$ Ed.]; and Golan, (2008) *Principles of Pharmacology: The Pathophysiologic Basis of Drug Therapy* [2$^{nd}$ Ed.] See, also, Grennaro (2005) [Ed.] *Remington: The Science and Practice of Pharmacy* [21$^{st}$ Ed.]

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., tumor, or systemic, wherein the composition is given to the patient and passes through the body widely, thereby reaching the site(s) of disease. Local administration (e.g., injection) may be accomplished by administration to the cell, tissue, organ, and/or organ system, which encompasses and/or is affected by the disease, and/or where the disease signs and/or symptoms are active or are likely to occur (e.g., tumor site). Administration can be topical with a local effect, composition is applied directly where its action is desired (e.g., tumor site).

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including one or more containers comprising pharmaceutical dosage units comprising an effective amount of one or more VISTA antagonists of the present invention. Kits may include instructions, directions, labels, marketing information, warnings, or information pamphlets.

The amount of VISTA antagonist in a therapeutic composition according to any embodiments of this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, and fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

As defined herein, a therapeutically effective amount of VISTA antagonist peptide, analog, derivative or mimetic thereof (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a peptide can include a single treatment or, preferably, can include a series of treatments.

In a preferred example, a subject is treated with peptide, analog, derivative or mimetic thereof in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

It will be appreciated that the pharmacological activity of the compositions may be monitored using standard pharmacological models that are known in the art. Furthermore, it will be appreciated that the compositions comprising a VISTA antagonist may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] *Remington: The Science and Practice of Pharmacy* [21$^{st}$ Ed.]

A peptide or analog, derivative or mimetic of this invention can be co-formulated with and/or coadministered with one or more additional therapeutic agents (e.g., an anti-cancer agent, an anti-viral agent, a cytokine and/or an immune agonist). Such combination therapies may require lower dosages of the peptide or analog, derivative or mimetic and/or the co-administered agents, thus avoiding possible toxicities or complications associated with the various monotherapies. There are a number of agents that may be advantageously combined with peptide or analog, derivative or mimetic of the invention and the selection of such agents will depend on the intended disease or condition to be treated. For example, the present invention includes combination therapies composed of a peptide or multimer, conjugate, analog, derivative or mimetic of the invention that is capable of inducing or promoting a response against a cancerous or pre-cancerous condition and at least one anti-cancer agent. Accordingly, in particular embodiments, the instant peptide or analog, derivative or mimetic is used as an adjuvant therapy in the treatment of cancer. As another example, the invention embraces combination therapies that include a peptide or analog, derivative or mimetic of the invention that is capable of inducing or promoting a therapeutic response against a viral infection and at least one anti-viral agent. Exemplary therapeutic agents that may be contained in the compositions comprising the VISTA antagonist peptide, multimer, conjugate, analog, derivative or mimetic include, e.g., CTLA-4-Ig, anti-PD-1, PD-L1 or PD-L2 fusion proteins and EGFR antagonists.

Anti-cancer agents include, but are not limited to, cytotoxic agents such as Vinca alkaloid, taxanes, and topoisomerase inhibitors; antisense nucleic acids such as augmerosen/G3139, LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2; anticancer nucleozymes such as angiozyme (Ribozyme Pharmaceuticals); tumor suppressor-encoding nucleic acids such as a p53, BRCA1, RB1, BRCA2, DPC4 (Smad4), MSH2, MLH1, and DCC; oncolytic viruses such as oncolytic adenoviruses and herpes viruses; anti-cancer immunogens such as a cancer antigen/tumor-associated antigen, e.g., an epithelial cell adhesion molecule (Ep-CAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines, tumor-derived heat shock proteins, and the like; anti-cancer cytokines, chemokines, or combination thereof; inhibitors of angiogenesis, neovascularization, and/or other vascularization; and/or any other conventional anticancer agent including fluoropyrimidiner carbamates, non-polyglutamatable thymidylate synthase inhibitors, nucleoside analogs, antifolates, topoisomerase inhibitors, polyamine analogs, mTOR inhibitors, alkylating agents, lectin inhibitors, vitamin D analogs, carbohydrate processing inhibitors, anti-metabolism folate antagonists, thumidylate synthase inhibitors, antimetabolites, ribonuclease reductase inhibitors, dioxolate nucleoside analogs, and chemically modified tetracyclines.

Anti-viral agents of use in the invention include, but are not limited to, protease inhibitors (e.g., acyclovir) in the context of HIV treatment or an anti-viral antibody (e.g., an anti-gp41 antibody in the context of HIV treatment; an anti-CD4 antibody in the context of the treatment of CMV, etc.). Numerous other types of anti-viral agents are known in the art.

Toxicity and therapeutic efficacy of the peptide or analog, derivative or mimetic can be determined by standard pharmaceutical procedures in cell cultures or experimental animals. The data obtained from the cell culture assays and animal studies can be used in formulating a range of dosage for use in humans. The dosage of such agents lies preferably within a range of circulating concentrations that include the $ED_{50}$ with little or no toxicity. The dosage may vary within this range depending upon the dosage form employed and the route of administration utilized. For any agent used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Use of VISTA Antagonists and Compositions Comprising the Same

The peptide or analog, derivative or mimetic of this invention finds use in inhibiting the activity of VISTA (i.e., PD-L3) thereby upregulating immune responses. Upregulation of immune responses can be in the form of enhancing an existing immune response or eliciting an initial immune response. For example, enhancing an immune response through inhibition of VISTA activity is useful in the prevention and/or treatment of infections with microbes, e.g., bacteria, viruses, or parasites, or in cases of immunosuppression and cancer.

Accordingly, the present invention includes prophylactic and therapeutic methods for the prevention and treatment of cancer and infectious disease. Terms such as "treat," "treating" and "treatment" herein refer to the delivery of an effective amount of a peptide or analog, derivative or mimetic of this invention with the purpose of easing, ameliorating, or eradicating (curing) such symptoms or disease states already developed. The terms "prevent," "preventing" and "prevention" refer to the delivery of an effective amount of a peptide or analog, derivative or mimetic of this invention with the purpose of preventing any symptoms or disease state to develop. Thus, these terms are meant to include prophylactic treatment.

Accordingly to one embodiment, the invention provides a method of treating or preventing cancer, inhibiting tumor invasion and/or cancer metastasis by administering to a subject in need thereof, such as a mammalian subject, preferably a human subject, an effective amount of an isolated VISTA antagonist disclosed herein or a composition containing said isolated VISTA antagonist. Optionally the subject has one or more precancerous lesions or is predisposed to cancer, e.g., as a result of genetic mutation, family history or exposure to a carcinogenic agent. In another embodiment the invention provides a method of treating cancer in subject, such as a mammalian subject, preferably a human subject, such as a human subject, who optionally has a detectable level of cancer cells. In accordance with these embodiments, the subject is administered a peptide or analog, derivative or mimetic of this invention in an amount sufficient to detectably reduce the development or progression of the cancer in the subject.

Cancers are generally composed of single or several clones of cells that are capable of partially independent growth in a host (e.g., a benign tumor) or fully independent growth in a host (malignant cancer). Cancer cells are cells that divide and reproduce abnormally with uncontrolled growth.

Cancer cells arise from host cells via neoplastic transformation (i.e., carcinogenesis). Terms such as "preneoplastic," "premalignant" and "precancerous" with respect to the description of cells and/or tissues herein refer to cells or tissues having a genetic and/or phenotypic profile that signifies a significant potential of becoming cancerous. Usually such cells can be characterized by one or more differences from their nearest counterparts that signal the onset of cancer progression or significant risk for the start of cancer progression. Such precancerous changes, if detectable, can usually be treated with excellent results.

In general, a precancerous state will be associated with the incidence of neoplasm(s) or preneoplastic lesion(s). Examples of known and likely preneoplastic tissues include ductal carcinoma in situ (DCIS) growths in breast cancer, cervical intra-epithelial neoplasia (CIN) in cervical cancer, adenomatous polyps of colon in colorectal cancers, atypical adenomatous hyperplasia in lung cancers, and actinic keratosis (AK) in skin cancers. Pre-neoplastic phenotypes and genotypes for various cancers, and methods for assessing the existence of a preneoplastic state in cells, have been characterized. See, e.g., Medina (2000) *J. Mammary Gland Biol. Neoplasia* 5(4):393-407; Krishnamurthy, et al. (2002) *Adv. Anat. Pathol.* 9(3):185-97; Ponten (2001) *Eur. J. Cancer* Suppl 8:S97-113; Niklinski, et al. (2001) *Eur. J. Cancer Prev.* 10(3):213-26; Walch, et al. *Pathobiology* (2000) 68(1): 9-17; Busch (1998) *Cancer Surv.* 32:149-79.

Gene expression profiles can increasingly be used to differentiate between normal, precancerous, and cancer cells. For example, familial adenomatous polyposis genes prompt close surveillance for colon cancer; mutated p53 tumor-suppressor gene flags cells that are likely to develop into aggressive cancers; osteopontin expression levels are elevated in premalignant cells, and increased telomerase activity also can be a marker of a precancerous condition (e.g., in cancers of the bladder and lung). In one aspect, the invention relates to the treatment of precancerous cells. In another aspect, the invention relates to the preparation of medicaments for treatment of precancerous cells.

In general, a peptide or analog, derivative or mimetic of this invention can be used to treat subjects suffering from any stage of cancer (and to prepare medicaments for reduction, delay, or other treatment of cancer). Effective treatment of cancer (and thus the reduction thereof) can be detected by any variety of suitable methods. Methods for detecting cancers and effective cancer treatment include clinical examination (symptoms can include swelling, palpable lumps, enlarged lymph nodes, bleeding, visible skin lesions, and weight loss); imaging (X-ray techniques, mammography, colonoscopy, computed tomography (CT and/or CAT) scanning, magnetic resonance imaging (MRI), etc.); immunodiagnostic assays (e.g., detection of CEA, AFP, CA125, etc.); antibody-mediated radioimaging; and analyzing cellular/tissue immunohistochemistry. Other examples of suitable techniques for assessing a cancerous state and effective cancer treatment include PCR and RT-PCR (e.g., of cancer cell associated genes or "markers"), biopsy, electron microscopy, positron emission tomography (PET), computed tomography, magnetic resonance imaging (MRI), karyotyping and other chromosomal analysis, immunoassay/immunocytochemical detection techniques (e.g., differential antibody recognition), histological and/or histopathologic assays (e.g., of cell membrane changes), cell kinetic studies and cell cycle analysis, ultrasound or other sonographic detection techniques, radiological detection techniques, flow cytometry, endoscopic visualization techniques, and physical examination techniques.

In general, delivering a peptide or analog, derivative or mimetic of this invention to a subject (either by direct administration or expression from a nucleic acid) can be used to reduce, treat, prevent, or otherwise ameliorate any aspect of cancer in a subject. In this respect, treatment of cancer can include, e.g., any detectable decrease in the rate of normal cells transforming to neoplastic cells (or any aspect thereof), the rate of proliferation of pre-neoplastic or neoplastic cells, the number of cells exhibiting a pre-neoplastic and/or neoplastic phenotype, the physical area of a cell media (e.g., a cell culture, tissue, or organ) containing pre-neoplastic and/or neoplastic cells, the probability that normal cells and/or preneoplastic cells will transform to neoplastic cells, the probability that cancer cells will progress to the next aspect of cancer progression (e.g., a reduction in metastatic potential), or any combination thereof. Such changes can be detected using any of the above-described techniques or suitable counterparts thereof known in the art, which typically are applied at a suitable time prior to the administration of a therapeutic regimen so as to assess its effectiveness. Times and conditions for assaying whether a reduction in cancer has occurred will depend on several factors including the type of cancer, type and amount of peptide, related composition, or combination composition being delivered to the host.

The methods of the invention can be used to treat a variety of cancers. Forms of cancer that may be treated by the delivery or administration of a peptide or analog, derivative or mimetic of this invention and combination therapies containing the same include squamous cell carcinoma, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, Burketts lymphoma, acute or chronic myelogenous leukemias, promyelocytic leukemia, fibrosarcoma, rhabdomyoscarcoma, melanoma, seminoma, teratocarcinoma, neuroblastoma, glioma, astrocytoma, neuroblastoma, glioma, schwannomas; fibrosarcoma, rhabdomyoscaroma, osteosarcoma, melanoma, xeroderma pigmentosum, keratoacanthoma, seminoma, thyroid follicular cancer, and teratocarcinoma. The compositions of this invention also can be useful in the treatment of other carcinomas of the bladder, breast, colon, kidney, liver, lung, ovary, prostate, pancreas, stomach, cervix, thyroid or skin. Compositions of this invention also may be useful in treatment of other hematopoietic tumors of lymphoid lineage, other hematopoietic tumors of myeloid lineage, other tumors of mesenchymal origin, other tumors of the central or peripheral nervous system, and/or other tumors of mesenchymal origin. Advantageously, the methods of the invention also may be useful in reducing cancer progression in prostate cancer cells, melanoma cells (e.g., cutaneous melanoma cells, ocular melanoma cells, and/or lymph node-associated melanoma cells), breast cancer cells, colon cancer cells, and lung cancer cells. The methods of the invention can be used to treat both tumorigenic and non-tumorigenic cancers (e.g., non-tumor-forming hematopoietic cancers). The methods of the invention are particularly useful in the treatment of epithelial cancers (e.g., carcinomas) and/or colorectal cancers, breast cancers, lung cancers, vaginal cancers, cervical cancers, and/or squamous cell carcinomas (e.g., of the head and neck). Additional potential targets include sarcomas and lymphomas. Additional advantageous targets include solid tumors and/or disseminated tumors (e.g., myeloid and lymphoid tumors, which can be acute or chronic).

The present invention also provides methods for enhancing anti-cancer or anti-tumor immunity, comprising administering to a subject in need thereof an effective amount of an isolated VISTA antagonist or a composition containing said isolated VISTA antagonist.

In addition to cancer treatment, the present invention also features a method of treating a pathogen infection, i.e., a bacterial, viral, parasitic or fungal infection, in a subject or host. This method involves administering or otherwise delivering an effective amount of a peptide or analog, derivative or mimetic of this invention so as to reduce the severity, spread, symptoms, or duration of such infection. Such pathogen infections include, but are not limited to diseases caused by bacteria, protozoa, fungi, parasites, or viruses.

In particular embodiments, a viral infection is treated. Any virus normally associated with the activity of effector lymphocytes can be treated by the method. For example, such a method can be used to treat infection by one or more viruses selected from hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus (CMV, e.g., HCMV), echinovirus, arbovirus, huntavirus, coxsackie virus, mumps virus, measles virus, rubella virus, polio virus, and/or human immunodeficiency virus type I or type 2 (HIV-1, HIV-2). The practice of such methods may result in a reduction in the titer of virus (viral load), reduction of the number of virally infected cells, etc.

In addition to pathogen infections, a peptide or analog, derivative or mimetic of this invention can be administered or otherwise delivered to a subject in association with the treatment of immunoproliferative diseases, immunodeficiency diseases, autoimmune diseases, inflammatory responses, and/or allergic responses. Moreover, the invention also provides methods for blocking, inhibiting or neutralizing VISTA-mediated T cell suppression and/or stimulating an immune response in a subject, comprising administering to the subject in need thereof an effective amount of an isolated VISTA antagonist or a composition containing said isolated VISTA antagonist. Such methods may be useful for treating a subject with a one or more of a bacterial, viral, parasitic and fungal infections and/or cancer.

EXAMPLES

The invention now being generally described, it will be more readily understood by reference to the following examples, which are included merely for purposes of illustration of certain aspects and embodiments of the present invention, and are not intended to limit the invention.

Example 1: Materials and Methods

Peptide Synthesis. AP1049 (SSACDWIKRSCH-amide, wherein Cys4-Cys11 form a disulfide bridge; SEQ ID NO:1 (Ser-Ser-Ala-Cys-Asp-Trp-Ile-Lys-Arg-Ser-Cys-His)) and scrambled negative control sequence (SSACKSWRDICH-amide, wherein Cys4-Cys11 form a disulfide bridge; SEQ ID NO:2) were prepared using standard Fmoc-based solid-phase peptide synthesis (SPPS). The peptides were purified via HPLC, and analyzed by mass spectrometric using the liquid chromatography-mass spectrometry (LC-MS) and matrix-assisted laser desorption/ionization (MALDI)

Peptide Discovery Using Phage Display. An M13 phage peptide library was provided by Dr. Brian Kay (U. Illinois-Chicago). The VISTA protein required for both the phage display biopanning experiments and the confirmatory ELISA binding experiments was prepared by conventional recombinant protein techniques.

T Cell Proliferation Assay. An VISTA-Ig fusion protein or control Ig fusion protein was co-absorbed to a cell-culture plate together with the polyclonal T cell receptor (TCR) stimuli (i.e., anti-CD3 antibody). To evaluate the activity of VISTA-specific peptides, peptides (VISTA specific and scrambled control) were added as a soluble reagent to the culture on day 0, and T cell proliferation and cytokine production were analyzed after 3-4 days.

T Cell Priming Assay. VISTA is known to suppress T cell priming when expressed on antigen-presenting cells (APCs). VISTA-expressing myeloid APCs ($Cd11b^{hi}$ $MHCII^+$ myeloid cells) were purified from mice spleen, FACS sorted, and irradiated (2500 rads). To test the activity of VISTA-specific peptides, transgenic T cells such as OT-II were stimulated ex vivo with VISTA-expressing APCs and cognate antigen chicken ovalbumin (15 ng/mL). VISTA-specific peptide or control scramble peptide was added to the cell culture. T cell proliferation and cytokine production was evaluated after 3-5 days of culture. As an additional specificity control, VISTA-negative parent cell line A20 or APCs purified from VISTA knockout mice were used.

Foxp3+CD4+ Regulatory T Cell (Treg) Suppression Assay. VISTA plays a role in the suppressive function of Foxp3+CD4+ regulatory T cells (Tregs), as VISTA-blocking monoclonal antibody partially reverses Treg suppressive activity in the in vitro Treg suppression assay. This assay includes antigen presenting cells, purified Foxp3+CD4+ Tregs, and Foxp3−CD4+ naïve T cells, which are stimulated by the polyclonal TCR stimuli. To examine the activity of VISTA-specific peptides, peptides (VISTA specific and scrambled control) were added to the Treg suppression assay on day 0. T cell proliferation and cytokine production were measured on day +3.

Model of Experimental Autoimmune Encephalomyelitis (EAE), a Murine Autoimmune Inflammatory Disease Model for Human Multiple Sclerosis. It has been shown that VISTA-blocking monoclonal antibody significantly accelerates disease onset, as well as exacerbates disease severity in a passive transfer EAE model. In this model, MOG-specific encephalitogenic CD4+ T cells are first primed in donor mice upon immunization with MOG peptide, and then purified and ex vivo expanded in the presence of MOG peptide and cytokines (IL23, TGFβ, IL6 and IL1b). Expanded encephalogenic CD4+ T cells are transferred into naïve recipients to induce disease. To evaluate the activity of VISTA-specific peptides, peptides (VISTA specific and scrambled control) are administered via intraperitoneal injections to mice either prophylactically (starting from day 2) or therapeutically (starting from day +7 during disease onset), and continuously every 2 days for the entire duration of the experiment. Disease severity is evaluated according to the established protocol.

Murine Tumor Models. It has been demonstrated that VISTA suppresses tumor-specific T cell responses. VISTA blockade via VISTA-specific monoclonal antibody significantly enhances anti-tumor immune responses and inhibits tumor progression in murine tumor models such as the B16 melanoma model. The activity of VISTA-specific peptides can be evaluated in vivo using this tumor model. Mice are inoculated on the flank with B16 tumor cells (15,000 cells) on day 0. Peptides (VISTA specific and scrambled control) are administered via intraperitoneal injections to mice either prophylactically (starting from day 2) or therapeutically (i.e., when tumors are palpable), and continuously every 2 days for the entire duration of the experiment. Tumor growth is measured every 2-3 days with a caliper.

Example 2: Enhancement of T Cell Proliferation $VISTA^+CD11b^+$ monocytes were enriched from naïve splenocytes using CD11b magnetic beads (Miltenyi). $VISTA^lCD11b^{hi}$ $MHCII^l$ myeloid APCs were FACS sorted, irradiated (2500 rads), and used as antigen-presenting cells to stimulate OT-II transgenic CD4⁻ T cells in the presence of OVA peptide. Control-Ig, monoclonal antibody specific for VISTA and PD-L1 (30 µg/mL), or VISTA-specific peptide (100 µg/mL) were added as indicated. Cell proliferation was measured by tritium incorporation during the last 8 hours of a 72-hour assay. This analysis indicated that T cell proliferation was enhanced in the presence of VISTA or PD-L1 neutralizing monoclonal antibodies, or the AP1049 peptide (FIG. 1). In fact, the AP1049 peptide stimulated T cell proliferation much better than either of the monoclonal antibodies, indicating that the peptide possesses strong antagonistic activity against VISTA.

Example 3: Enhancement of Anti-Tumor Immunity

Immunogenic bladder carcinoma tumors (MB49) were inoculated in female mice. AP1049 was tested for its ability to slow tumor growth and/or facilitate tumor regression. The readout for this assay was tumor growth.

MB49 tumors were inoculated in female mice (300k) via intradermal (i.d.) inoculation, which facilitates measurement of tumor size. Mice were treated with either PBS (control) or VISTA antagonist peptide (AP1049), via daily injections around tumor mass starting on day+1 and continuing for 2 weeks. Tumor size was measured by caliper every 2-3 days.

Using these methods slowed tumor growth and/or tumor regression in mice treated with AP1049 was obtained as compared with mice treated with control.

Figure 2:
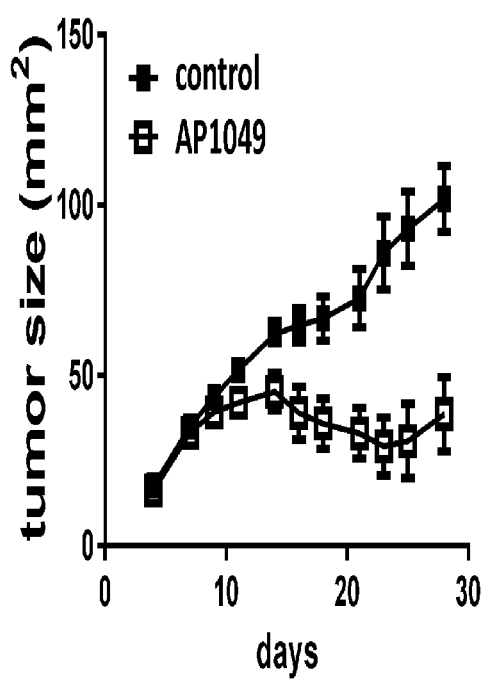
FIG. 2 shows that a VISTA antagonist peptide (SEQ ID NO:1) significantly enhances anti-tumor immunity. Female mice inoculated with MB49 tumors were treated with either PBS (control) or AP1049. Tumor size was measured by caliper every 2-3 days.

As shown in FIG. 2, AP1049 treatment reduced tumor growth in the MB49 tumor model, indicating that the peptide may bind to the critical/active site of VISTA and block the immune-suppressive function of VISTA.

thereof an effective amount of a VISTA antagonist comprising a peptide which is identical to the amino acid sequence of SEQ ID NO:1 (Ser-Ser-Ala-Cys-Asp-Trp-Ile-Lys-Arg-Ser-Cys-His), or a multimer, or a conjugate thereof.

4. The method of claim 1, which includes the administration of another therapeutic agent wherein the other therapeutic agent is an anti-cancer agent, an anti-viral or other anti-infectious agent, a cytokine or an immune agonist.

5. The method of claim 4, wherein the immune agonist or anti-cancer agent is selected from CTLA-4-1g, anti-PD-1, PD-L1 or PD-L2 fusion proteins, and EGFR antagonists.

6. The method of claim 1, wherein the VISTA antagonist is attached to an albumin or an immunoglobulin polypeptide or a fragment thereof and/or the VISTA antagonist is attached to a polyethylene glycol and/or is acetylated.

7. The method of claim 6, wherein said immunoglobulin polypeptide comprises a human IgG1, IgG2, IgG3 or IgG4 constant region or fragment thereof.

8. The method of claim 7, wherein said immunoglobulin polypeptide comprises a human IgG1 constant region or fragment thereof.

9. The method of claim 1, wherein the VISTA antagonist is attached to a moiety that targets said peptide to a target site.

10. The method of claim 2, wherein the VISTA antagonist is attached to a moiety that targets said peptide to a target site.

11. The method of claim 3, wherein the VISTA antagonist is attached to a moiety that targets said peptide to a target site.

12. The method of claim 9, wherein said moiety comprises an antibody or ligand that binds to an antigen, or receptor expressed by a target cell or an infectious agent.

What is claimed is:

1. A method for blocking, inhibiting or neutralizing VISTA-mediated T cell suppression, comprising administering to a subject in need thereof an effective amount of a VISTA antagonist comprising a peptide which is identical to the amino acid sequence of SEQ ID NO:1 (Ser-Ser-Ala-Cys-Asp-Trp-Ile-Lys-Arg-Ser-Cys-His), or a multimer, or a conjugate thereof.

2. A method for stimulating an immune response in a subject, comprising administering to the subject in need thereof an effective amount of a VISTA antagonist comprising a peptide which is identical to the amino acid sequence of SEQ ID NO:1 (Ser-Ser-Ala-Cys-Asp-Trp-Ile-Lys-Arg-Ser-Cys-His), or a multimer, or a conjugate thereof.

3. A method for enhancing anti-cancer or anti-tumor immunity, comprising administering to a subject in need 13. The method of claim 10, wherein said moiety comprises an antibody or ligand that binds to an antigen, or receptor expressed by a target cell or an infectious agent.

14. The method of claim 11, wherein said moiety comprises an antibody or ligand that binds to an antigen, or receptor expressed by a target cell or an infectious agent.

15. The method of claim 1, wherein said VISTA antagonist is expressed by a recombinant cell.

16. The method of claim 2, wherein said VISTA antagonist is expressed by a recombinant cell.

17. The method of claim 3, wherein said VISTA antagonist is expressed by a recombinant cell.

* * * * *